US009216201B2

(12) United States Patent
Iwasaki et al.

(10) Patent No.: US 9,216,201 B2
(45) Date of Patent: Dec. 22, 2015

(54) METHOD FOR REGENERATING HYALINE CARTILAGE

(71) Applicants: MOCHIDA PHARMACEUTICAL CO., LTD., Shinjuku-ku, Tokyo (JP); NATIONAL UNIVERSITY CORPORATION HOKKAIDO UNIVERSITY, Sapporo-shi, Hokkaido (JP)

(72) Inventors: Norimasa Iwasaki, Hokkaido (JP); Akio Minami, Hokkaido (JP); Yasuhiko Kasahara, Hokkaido (JP); Tatsuya Igarashi, Hokkaido (JP); Daisuke Kawamura, Hokkaido (JP); Fumiyoshi Kasahara, Tokyo (JP); Chihiro Miyajima, Tokyo (JP); Nobuo Ohzawa, Tokyo (JP); Mariko Imai, Tokyo (JP)

(73) Assignees: Mochida Pharmaceutical Co., Ltd., Tokyo (JP); National University Corporation Hokkaido University, Hokkaido (JP)

( * ) Notice: Subject to any disclaimer, the term of this patent is extended or adjusted under 35 U.S.C. 154(b) by 261 days.

(21) Appl. No.: 13/737,171

(22) Filed: Jan. 9, 2013

(65) Prior Publication Data
US 2013/0189231 A1 Jul. 25, 2013

Related U.S. Application Data

(62) Division of application No. 12/311,426, filed as application No. PCT/JP2008/052999 on Feb. 21, 2008, now Pat. No. 8,372,394.

(30) Foreign Application Priority Data

Feb. 21, 2007 (JP) .................................. 2007-041520
Oct. 24, 2007 (JP) .................................. 2007-277005

(51) Int. Cl.
*A61L 31/16* (2006.01)
*A61K 35/28* (2015.01)
*A61L 27/20* (2006.01)
*A61L 27/38* (2006.01)
*A61K 31/734* (2006.01)

(52) U.S. Cl.
CPC .............. *A61K 35/28* (2013.01); *A61K 31/734* (2013.01); *A61L 27/20* (2013.01); *A61L 27/3834* (2013.01); *A61L 27/3852* (2013.01); *A61L 2430/06* (2013.01)

(58) Field of Classification Search
None
See application file for complete search history.

(56) References Cited

U.S. PATENT DOCUMENTS

| 8,372,394 B2* | 2/2013 | Iwasaki et al. ............... 424/93.7 |
| 2004/0048772 A1 | 3/2004 | Nakagiri et al. |
| 2005/0164980 A1 | 7/2005 | Shimoboji |
| 2006/0241066 A1 | 10/2006 | Tomita et al. |

FOREIGN PATENT DOCUMENTS

| EP | 1 496 037 A1 | 1/2005 |
| JP | 7-504682 A | 5/1995 |
| JP | 10-101577 A | 4/1998 |
| JP | 2001-505809 A | 5/2001 |
| JP | 2001-517494 A | 10/2001 |
| JP | 2002-530440 A | 9/2002 |
| JP | 2007-075425 A | 3/2007 |
| WO | WO 94/00134 A1 | 1/1994 |
| WO | WO 98/25653 A2 | 6/1998 |
| WO | WO 99/15211 A1 | 4/1999 |
| WO | WO 00/29449 A1 | 5/2000 |
| WO | WO 02/055073 A1 | 7/2002 |
| WO | WO 03/099339 A1 | 12/2003 |
| WO | WO 2006/044342 A2 | 4/2006 |

OTHER PUBLICATIONS

Okamoto et al., "Trend of Clinical Application and Vision for the Future, Tissue Engineering for Bone and Cartilage Repair" Nippon Rinsho (Japanese Journal of Clinical Medicine), 2003, 61(3):432-438, with English translation, 6 pages.

Umezawa et al., "Clinical practice and Pathology of Organ Transplantation: Particular Theories Cell Transplantation and Organ Regeneration," Byiro to Rinsho (Pathology and Clinical Medicine), 2001, 19(6):641-647, with English translation, 8 pages.

Yuge, Rui, "Research and development of device for creating artificial zero gravity and application thereof to regeneration medicine," [Speech II], High Technology Information, 2003, 149:26-39, with partial English translation of indicated portions, 6 pages.

Fragonas et al., "Articular cartilage repair in rabbits by using suspensions of allogenic chondrocytes in alginate," Biomaterials, 2000, 21:795-801.

Hoshikawa et al., "Osteoarthritis and bioengineering," Igaku no Ayumi, 2004, 211(4):269-273., with partial English translation, 4 pages.

Igarashi et al., "Development of a novel cell implanation system for repair of osteochondral defects," The 26th Annual Meeting of Japanese Society for Transplantation and Tissue Engineering in Musculoskeletal System, Program and Excerpts, Oct. 12, 2007, p. 22, with English translation, 3 pages.

(Continued)

*Primary Examiner* — Hope Robinson
(74) *Attorney, Agent, or Firm* — Foley & Lardner LLP

(57) ABSTRACT

The present invention provides a composition for regenerating cartilage or treating a cartilage disease containing a monovalent metal salt of alginic acid for which the endotoxin level thereof has been lowered to an extent that does not substantially induce inflammation or fever. As a result, it is possible to provide a composition for regenerating cartilage that improves cartilage regenerative action and ease of application to a cartilage injury lesion, and a composition for treating a cartilage disease, which has the effects of protecting cartilage from mechanical irritation, inhibiting degenerative changes in cartilage caused by wear and inflammation, repairing a cartilage injury lesion, and inhibiting inflammation and pain of joint tissue.

19 Claims, 23 Drawing Sheets

(56) References Cited

OTHER PUBLICATIONS

Igarashi et al., "Nankotsu Saisei ni Muketa Kokasei Kojundo Tei-Endotoxin Alginic Acid Gel o Mochiita Shinki Ishoku System no Kaihatsu," J. Jpn. Orthop. Assoc., 2007, 81(8):S838, two pages, with English translation "Development of novel implantation system for cartilage regeneration using a curable high-purity low-endotoxin alginate gel," 3 pages.

Liu et al., "Osteochondral Defect Repair with Autologous Bone Marrow-Derived Mesenchymal Stem Cells in an Injectable In Situ, Cross-Linked Synthetic Extracellular Matrix," Tissue Engineering, 2006, 12(12):3405-3416.

Ma et al., "Chondrogenesis of human mesenchymal stem cells encapsulated in alginate beads," J. Biomed. Matre. Res., 2003, 64A(2):273-281.

Marijnissen et al., "Alginate as a chondrocyte-delivery substance in combination with a non-woven scaffold for cartilage tissue engineering," Biomaterials, 2002, 23(6):1511-1517.

Matsumine et al., "3. Hone Nankotsu no Saisei. Shufuku—Rinsho oyo eno Tenbo," Experimental Medicine, 2002, 20(17, extra issue):2569-2574, with partial English translation "3. Osteochondral regeneration and repair—Prospect for clinical application," 1 page.

Nakaya et al., "Repair of articular cartilage defect by autologous bone marrow mesenchymal cell transplantation," Kansetsu Geka, 2003, 22(10):1283-1286, with partial English translation, 2 pages.

Pelletier et al., "Amphiphilic derivatives of sodium alginate and hyaluronate for cartilage repair: Rheological properties," Journal of Biomedical Materials Research, 2000, 54(1):102-108.

Ponticiello et al., "Gelatin-based resorbable sponge as a carrier matrix for human mesenchymal stem cells in cartilage regeneration therapy," Journal of Biomedical Materials Research, 2000, 52(2):246-255.

\* cited by examiner

Fig. 4
(A) 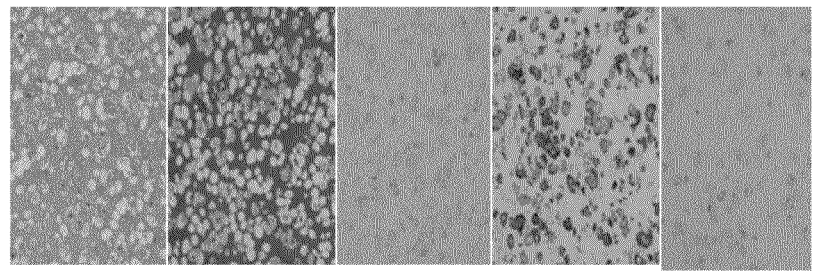
(B) 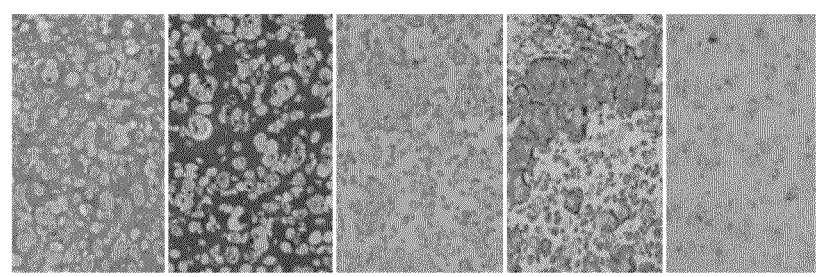
(C) 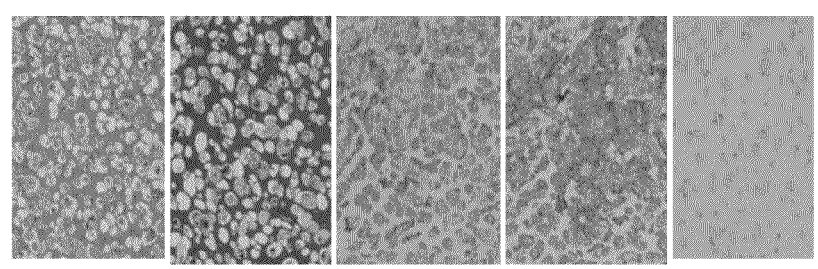
(D) 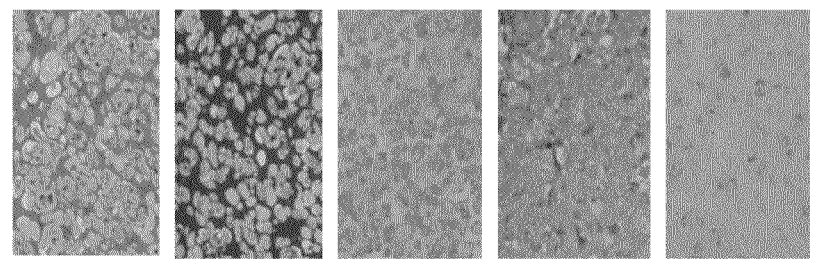

Fig. 5
(A)
(B)
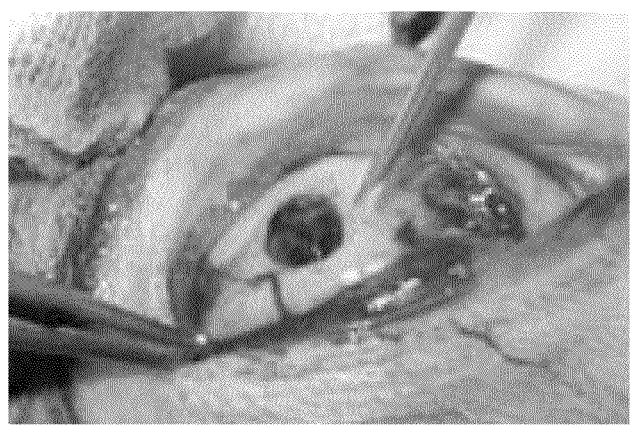
(C)
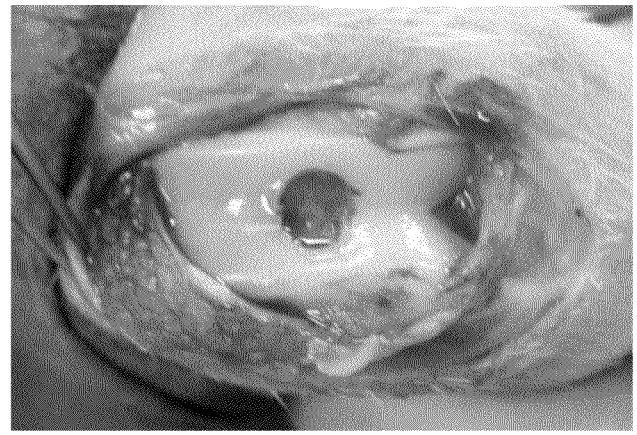

Fig. 6

| | | |
|---|---|---|
| Edge Integration (new tissue relative to native cartilage) | Full | 2 |
| | Partial | 1 |
| | None | 0 |
| Smoothness of the cartilage surface | Smooth | 2 |
| | Intermediate | 1 |
| | Rough | 0 |
| Cartilage surface, degree of filling | Flush | 2 |
| | Slight depression | 1 |
| | Depressed/overgrown | 0 |
| Color of cartilage, opacity or translucency of the neocartilage | Transparent | 2 |
| | Translucent | 1 |
| | Opaque | 0 |

Fig. 7

| | Characteristic | | Score |
|---|---|---|---|
| I. | Nature of predominant tissue | Hyaline cartilage | 4 |
| | | Mostly hyaline cartilage | 3 |
| | | Mixed hyaline and fibrocartilage | 2 |
| | | Mostly fibrocartilage | 1 |
| | | Some fibrocartilage, mostly nonchondrocytic cells | 0 |
| II. | Structural characteristics | | |
| | A. Surface regularity | Smooth and intact | 3 |
| | | Superficial horizontal lamination | 2 |
| | | Fissures | 1 |
| | | Severe disruption, including fibrillation | 0 |
| | B. Structural integrity, homogeneity | Normal | 2 |
| | | Slight disruption, including cysts | 1 |
| | | Severe disintegration, disruptions | 0 |
| | C. Thickness | 100% of normal adjacent cartilage | 2 |
| | | 50–100% of normal cartilage | 1 |
| | | 0–50% of normal cartilage | 0 |
| | D. Bonding to adjacent cartilage | Bonded at both ends or graft | 2 |
| | | Bonded at one end or partially at both ends | 1 |
| | | Not bonded | 0 |
| III. | Freedom from cellular changes of degeneration | | |
| | A. Hypocellularity | Normal cellularity | 2 |
| | | Slight hypocellularity | 1 |
| | | Moderate hypocellularity or hypercellularity | 0 |
| | B. Chondrocyte clustering | No clusters | 2 |
| | | <25% of the cells | 1 |
| | | 25–100% of the cells | 0 |
| IV. | Freedom from degenerative changes in adjacent cartilage | | |
| | | Normal cellularity, no clusters, normal staining | 3 |
| | | Normal cellularity, mild clusters, moderate staining | 2 |
| | | Mild or moderate hypo/hypercellularity, slight staining | 1 |
| | | Severe hypocellularity, poor or no staining | 0 |
| V. | Subchondral bone | | |
| | A. Reconstruction of subchondral bone | Normal | 3 |
| | | Reduced subchondral bone reconstruction | 2 |
| | | Minimal subchondral bone reconstruction | 1 |
| | | No subchondral bone reconstruction | 0 |
| | B. Inflammatory response in subchondral bone region | | |
| | | None/mild | 2 |
| | | Moderate | 1 |
| | | Severe | 0 |
| VI. | Safranin-O staining | Normal or near normal | 3 |
| | | Moderate | 2 |
| | | Slight | 1 |
| | | None | 0 |
| Total maximum score: | | Sections with safranin-O | 28 |
| | | Section with H&E | 25 |

Fig. 8
(A)
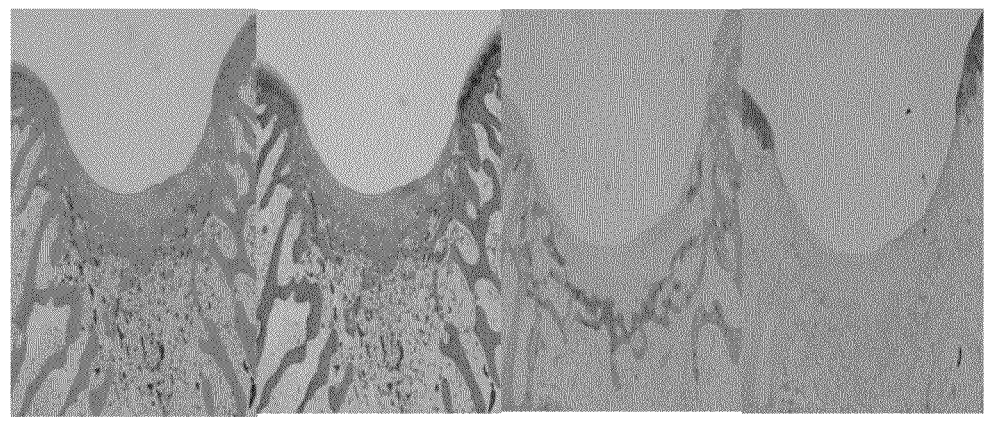
(B)
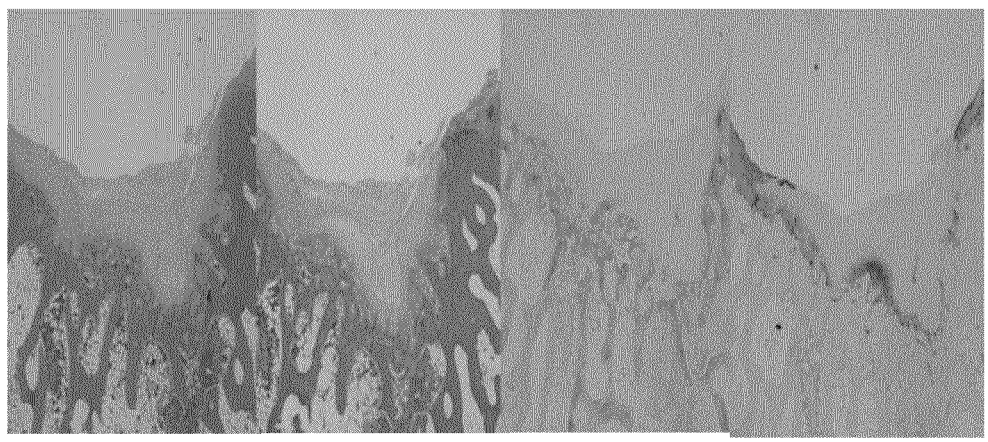

Fig. 9
(A)
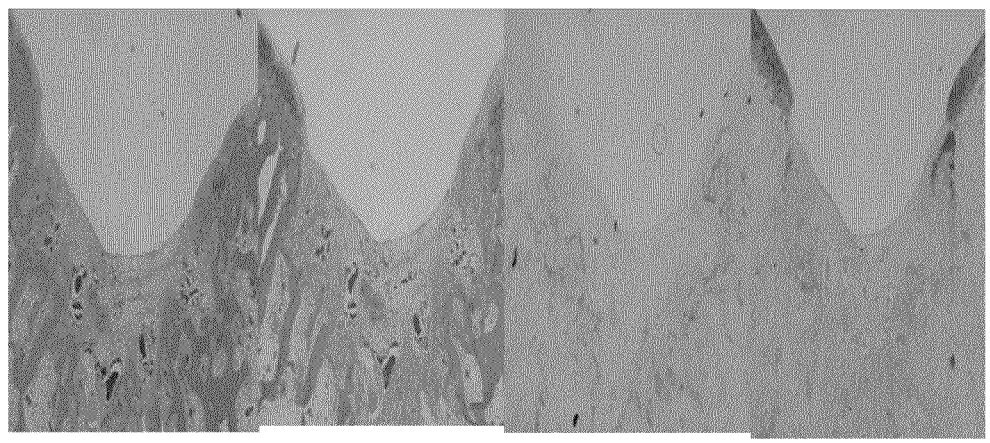
(B)
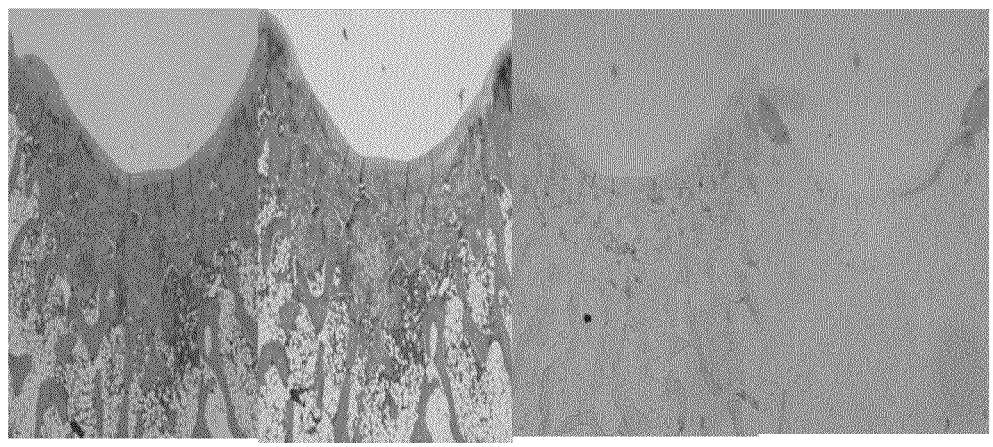

Fig. 10
(A)
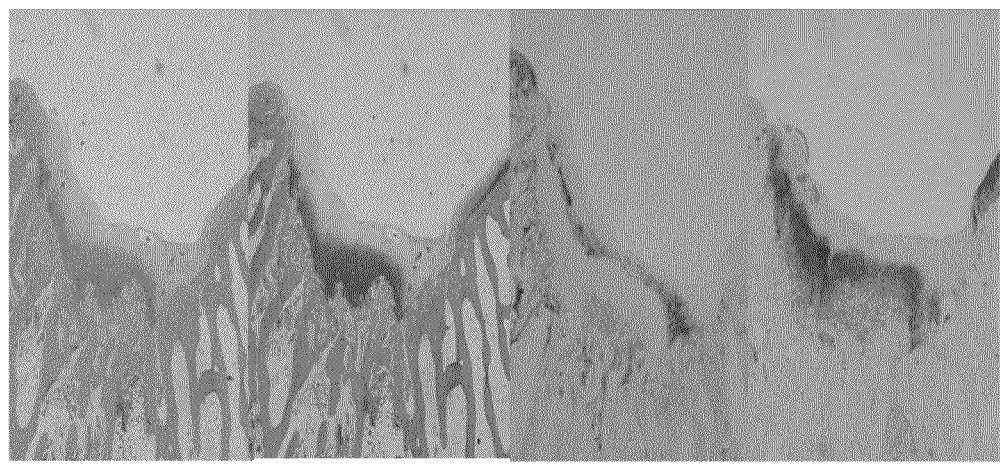
(B)
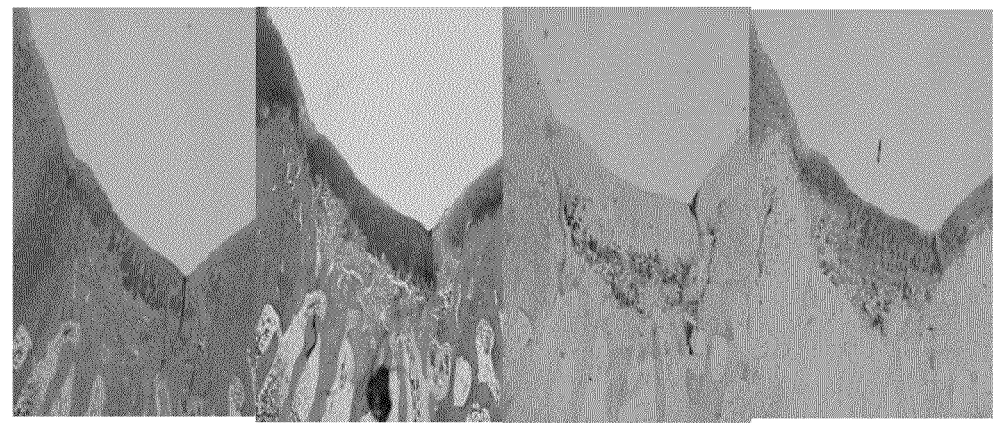

Fig. 11
(A)
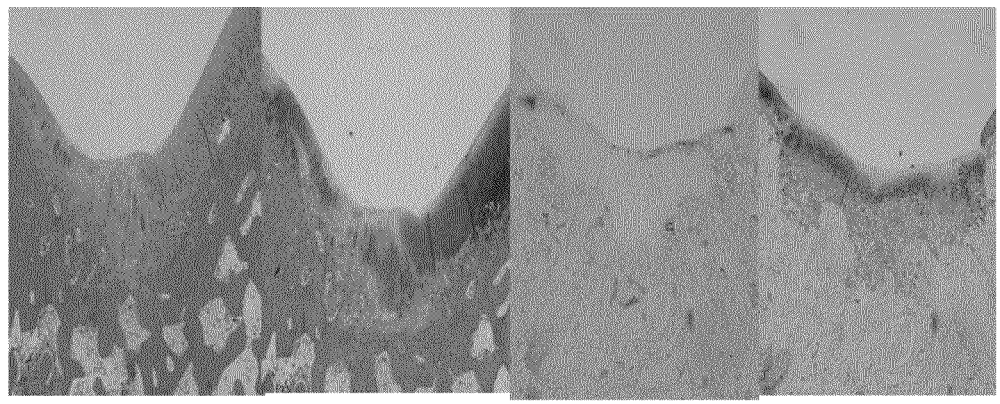
(B)
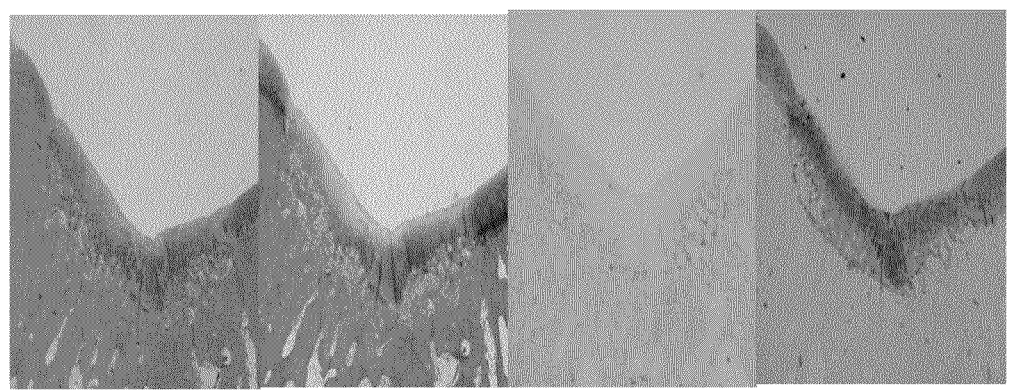

Fig. 12

| | 4w | | | | | 12w | | | | |
|---|---|---|---|---|---|---|---|---|---|---|
| | Control (empty) | Food grade alginate (no cell) | Food grade alginate + cells | pure alginate (no cell) | pure alginate + cells | Control (empty) | Food grade alginate (no cell) | Food grade alginate + cells | pure alginate (no cell) | pure alginate + cells |
| Macro | | | | | | | | | | |
| Edge Integration | 0.80 | 0.50 | 0.50 | 0.63 | 0.90 | 0.71 | 0.50 | 1.00 | 1.00 | 1.57 |
| Smoothness of the cartilage surface | 0.20 | 0.25 | 0.50 | 0.75 | 1.20 | 0.43 | 0.75 | 0.75 | 1.00 | 1.43 |
| Cartilage surface, degree of filling | 0.20 | 0.75 | 0.50 | 1.13 | 1.40 | 0.57 | 1.00 | 1.00 | 1.71 | 1.71 |
| Color of cartilage | 0.20 | 0.00 | 0.17 | 0.63 | 0.70 | 0.14 | 0.25 | 0.25 | 0.86 | 1.00 |
| total | 1.40 | 1.50 | 1.67 | 3.13 | 4.20 | 1.86 | 2.50 | 3.00 | 4.57 | 5.71 |
| Histological | | | | | | | | | | |
| Nature of predominant tissue | 0.40 | 0.75 | 0.50 | 0.75 | 1.50 | 0.14 | 0.75 | 0.50 | 1.57 | 1.29 |
| surface regularity | 0.00 | 0.25 | 0.33 | 1.00 | 1.50 | 0.29 | 0.50 | 0.75 | 1.14 | 2.00 |
| Structural integrity, homogeneity | 0.80 | 1.00 | 0.67 | 0.50 | 0.90 | 0.43 | 0.75 | 0.75 | 1.00 | 1.00 |
| Thickness | 0.60 | 1.00 | 1.17 | 1.00 | 1.70 | 0.57 | 1.00 | 1.25 | 1.57 | 1.86 |
| Bonding to adjacent cartilage | 0.80 | 0.25 | 0.67 | 1.00 | 1.30 | 0.71 | 0.50 | 1.25 | 1.43 | 1.71 |
| Hypocellularity | 0.00 | 0.25 | 0.33 | 0.38 | 0.80 | 0.00 | 0.50 | 0.25 | 0.57 | 0.43 |
| Chondrocyte clustering | 0.00 | 0.50 | 0.50 | 0.25 | 0.20 | 0.00 | 0.50 | 0.25 | 0.29 | 0.43 |
| degenerative changes in adjacent cartilag | 1.20 | 0.75 | 1.50 | 1.88 | 2.80 | 1.29 | 0.75 | 2.00 | 2.57 | 2.86 |
| Reconstruction of subchondral bone | 0.80 | 0.50 | 1.17 | 1.00 | 1.30 | 1.14 | 1.00 | 2.25 | 1.71 | 2.14 |
| Inflammatory response | 1.40 | 1.25 | 1.00 | 1.63 | 1.70 | 1.71 | 0.75 | 1.50 | 1.86 | 2.00 |
| Safranin-O staining | 0.40 | 1.00 | 1.00 | 0.75 | 1.30 | 0.29 | 0.75 | 1.00 | 1.29 | 1.00 |
| total | 6.40 | 7.50 | 8.83 | 10.13 | 15.00 | 6.57 | 7.75 | 11.75 | 15.00 | 17.00 |
| total score | 7.80 | 9.00 | 10.50 | 13.25 | 19.20 | 8.43 | 10.25 | 14.75 | 19.57 | 22.71 |

Fig. 14
(A)
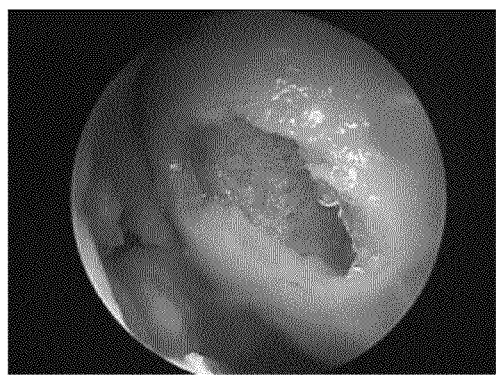
(B)
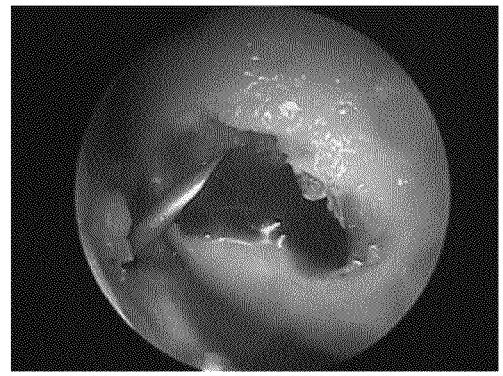
(C)
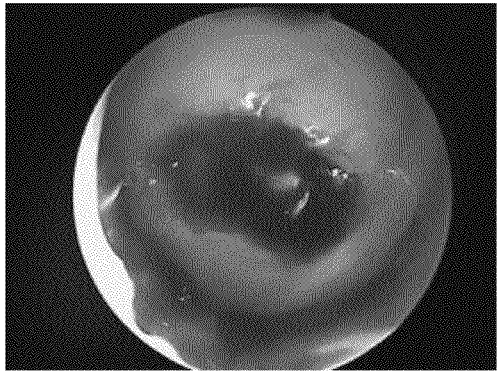
(D)
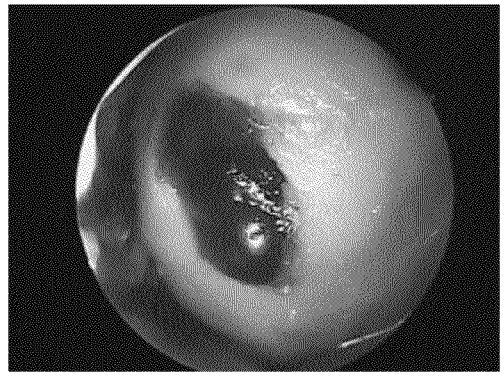

METHOD FOR REGENERATING HYALINE CARTILAGE

CROSS-REFERENCE TO RELATED APPLICATIONS

This application is a Divisional of U.S. application Ser. No. 12/311,426, which is the U.S. National Stage application of PCT/JP2008/052999, filed Mar. 30, 2009, which claims priority from Japanese applications JP 2007-041520, filed Feb. 21, 2007, and JP 2007-277005, filed Oct. 24, 2007.

The instant application contains a Sequence Listing which has been submitted in ASCII format via EFS-WEB and is hereby incorporated by reference in its entirety. Said ASCII copy, created on Jan. 8, 2013, is named sequence.txt and is 3 KB.

TECHNICAL FIELD

The present invention relates to a composition for cartilage regeneration or cartilage disease treatment, including veterinary applications.

BACKGROUND OF THE INVENTION

For example, articular cartilage is hyaline cartridge that is composed of a small number of cells, collagenous extracellular matrix, abundant proteoglycans and water. In the case of bone, since vascular and neural networks are present and bone has the ability to self-repair, even if a fracture has occurred, the fracture is frequently completely repaired. However, articular cartilage lacks vascular and neural networks. Consequently, it has virtually no potential for self-repair, and in the case of the formation of large cartilage defects in particular, the cartilage defect is not adequately repaired. Even at those portions that are repaired, fibrous cartilage is formed that has different mechanical properties than hyaline cartilage. Consequently, when a cartilage defect is formed, joint pain and loss of function are brought about that frequently progress to osteoarthritis. In addition, a cartilage defect can reach over a broad range as a result of symptoms progressing from the initial stages of osteoarthritis that began with wear of the surface of articular cartilage due to aging or excessive joint usage.

In this manner, since articular cartilage lacks an adequate self-repair ability, surgical procedures are required to treat cartilage injuries, examples of which include mosaicplasty, microfracture, drilling, abrasion and debridement. Among these, microfracture, drilling and abrasion are referred to as marrow stimulation techniques, and promote bleeding from bone marrow to induce bone marrow-derived cartilage precursor cells in anticipation of their differentiation into cartilage. However, these techniques have limitations with respect to cartilage defects covering a wide area, and cartilage regenerated by these methods is in the form of fibrous cartilage having different mechanical properties than hyaline cartilage.

Peterson et al. and Grande et al. tested an autologous chondrocyte implantation (ACI) technique in rabbit partial thickness articular cartilage in 1984. ACI is a technique involving the harvesting and culturing of tissue from a patient's own normal cartilage, implanting the cultured cells at an affected area while suspended in a medium, and covering the cartilage defect with the periosteum to prevent leakage of the cells. ACI was first applied clinically in 1994 and has currently been in practice for more than 15 years. Several successful outcomes have been reported. However, recent clinical studies have reported that ACI does not yield significantly superior results when compared with other techniques for repair of articular cartilage defects.

There are two major reasons for these unfavorable results obtained with ACI. The first is the technical difficulty associated with fixing the cells and scaffold to the cartilage defect and covering the defect with a periosteal flap. The ACI technique requires a wide arthrotomic exposure of the joint for suturing the periosteal flap to cover the cell suspension. Moreover, several complications associated with the periosteal flap have been reported, including periosteal hypertrophy, defect formation and intra-articular adhesion. The other reason involves limitations on the use of chondrocytes. Chondrocytes rapidly lose their differential phenotype in monolayer cultures, transforming into fibroblasts. Another problem is that although ACI requires cartilage to be harvested from a non-weight-bearing site of the joint, donor sites remain problematic since chondrocytes are harvested there from.

On the other hand, attempts are also progressing on the use of natural polymers such as collagen, chitosan, agarose and alginic acid in regenerative therapy of articular cartilage. In particular, alginic acid is a polysaccharide extracted from brown algae such as *Ecklonia, Eisenia* and *Laminaria* that has the property of crosslinking following the addition of calcium or other divalent metal ions, and attempts have been made to apply alginic acid to injured sites by utilizing this property to embed cells such as chondrocytes, growth factors and so on in a gel thereof (see, for example, References 1, 2, 3, 4 and 5).

For example, Reference 1 discloses an alginate gel comprising a mixture of a soluble alginate and an insoluble alginate/gel, while References 2, 3 and 4 disclose the use of alginate beads. In Reference 2, alginic acid can be used as a carrier that does not impart any disadvantageous effects on an injured site, although alginic acid itself is discussed as not having any therapeutic effects. In addition, Reference 4 discloses that chondrocytes embedded in alginate beads were not observed to fuse to host tissue after transplanting to a rabbit cartilage defect. In addition, although alginate beads are required to be applied by being pressed into a defect, since it is necessary to produce beads that match the size of the defect, their use in the actual clinical setting is technically difficult. Reference 5 discloses a graft in which chondrocytes are suspended in sodium alginate and injected into a rabbit cartilage defect followed by curing the surface with $CaCl_2$ solution, wherein although normal cartilage tissue is formed, fibrous cartilage is formed in the case of applying only alginic acid to the cartilage defect without containing cells.

In addition, research is progressing on the use of collagen sponge and the like as a cell scaffold as an example of attempts to use mesenchymal stem cells for cartilage regenerative therapy. Although methods involving transplantation of mesenchymal stem cells following in vitro differentiation to chondrocytes, and methods involving transplantation of mesenchymal stem cells without differentiating have been considered, there is still continuing debate over which utilization method is optimal (Reference 6).

Since cartilage defects in osteoarthritis (OA) occur over a wide range and in regions subjected to loads, their repair by transplant or regenerative therapy is considered to be difficult. Those cartilage defects eligible for cartilage regeneration by cell transplant as described above are limited to partial cartilage defects caused mainly by sporting activities or trauma. Treatment of osteoarthritis focuses primarily on the removal of pain and inflammation at the affected area, and is commonly treated overseas with administration of non-steroid anti-inflammatory drugs. However, since renal function may be depressed in elderly patients, continuous oral administration of non-steroid anti-inflammatory drugs may be difficult from the viewpoint of safety. Products incorporating hyaluronic acid, which is a component of cartilage synovial fluid, improve the lubricating function of joints by being administered into a joint, and since these products also having analgesic action, they are widely used as joint function improving agents for osteoarthritis. However, since there is ultimately no other choice than to replace the joint with an artificial joint in severe cases of osteoarthritis in which joint damage has progressed, there is a desire for the development of a novel therapeutic drug.

REFERENCES

1. International Publication WO 2006/044342
2. Cay M. Mierisch et al., "Transforming Growth Factor β in Calcium Alginate Beads for the Treatment of Articular Cartilage Defects in the Rabbit", The Journal of Arthroscopic and Related Surgery, Vol. 18, No. 8 (October), 2002: pp. 892-900
3. David R. Diduch et al., "Marrow Stromal Cells Embedded in Alginate for Repair of Osteochondral Defects", The Journal of Arthroscopic and Related Surgery, Vol. 16, No. 6 (September), 2000: pp. 571-577
4. David R. Diduch et al., "Chondrocyte Transplantation into Articular Cartilage Defects with Use of Calcium Alginate: The Fate of the Cells", J Bone Joint Surg. Am. 85: 2003, pp. 1757-1767
5. E. Fragonas et al., "Articular Cartilage Repair in Rabbits by Using Suspensions of Allogenic Chondrocytes in Alginate", Biomaterials, Vol. 21, 2000: pp. 795-801
6. Life Science Report No. 4, 2005 (Editor: Intellectual Property Department, Tokyo Medical and Dental University, Publisher: Maruzen Co., Ltd.), pp. 235-243, Cooperating editor: Ichiro Sekiya

DISCLOSURE OF THE INVENTION

Problems to be Solved by the Invention

When considering actual clinical applications for regenerative therapy of cartilage defects in this manner, there has been no regenerative therapy capable of withstanding practical use in terms of such problems as cytotoxicity, bioaffinity, ease of application and therapeutic effects. Namely, there has been a need for the development of a composition for cartilage regeneration and treatment of cartilage diseases, and a treatment method using the same, having superior practicality by overcoming problems in the field of cartilage regenerative therapy by being capable of effectively promoting cartilage regeneration without requiring an excessive surgical procedure in the manner of ACI, having a simple procedure and without placing an excessive burden on the body in terms of harvesting chondrocytes, periosteum and the like, being capable of being used over a wide range of various forms of cartilage injuries regardless of the application conditions, reducing the detrimental effects of crosslinking agents and the like applied to cartilage injuries, and having superior bioaffinity. In particular, there has yet to be a composition capable of regenerating hyaline cartilage using polymer alone without embedding cells.

Although osteoarthritis is a degenerative disease in which articular cartilage is worn down due to aging and excessive joint use, in addition to the mechanical cause of wear, local inflammatory responses, such as the production of inflammatory cytokines by synovial cells and chondrocytes and the induction of algesic substances and proteases by inflammatory cytokines, are also said to be involved in joint destruction. Namely, accompanying wear of articular cartilage (mechanical damage), an inflammatory response is induced within joint tissue, self-destructive cartilage damage progresses due to this inflammatory response and mechanical damage further progresses due to decreased joint function, thereby resulting in a vicious cycle that further exacerbates the disease. Thus, therapeutic drugs for osteoarthritis are required to provide comprehensive effects, including effects that protect cartilage from wear, effects that inhibit degenerative changes in cartilage caused by wear and inflammation, effects that repair cartilage injury lesion, and effects that suppress inflammation and pain. If a drug capable of inhibiting inflammation and suppressing pain in joints was able to be obtained, it could be applied to the treatment of frozen shoulder and suppression of joint pain in chronic rheumatoid arthritis. Hyaluronic acid is inherently a major component of synovial fluid, and replenishing this improves joint function. At present, there are no drugs known to have comprehensive therapeutic effects on cartilage tissue other than hyaluronic acid. Hyaluronic acid preparations are produced by extracting from animal tissue or fermenting, and novel materials are sought that can be produced more easily and offer a higher level of safety. In addition, although hyaluronic acid preparations require five consecutive weekly administrations initially followed by repeated administrations thereafter, a novel composition is sought that has a longer duration and higher therapeutic effects in order to reduce the number of injections into the knee joint.

Means for Solving the Problems

The inventors of the present invention conducted extensive studies to solve the above-mentioned problems. As a result, it was found that by applying to a cartilage injury lesion a composition containing a monovalent metal salt of alginic acid for which the endotoxin level thereof has been lowered to an extent that does not substantially induce fever or inflammation, having the viscosity of 400 to 20000 mPa·s and having fluidity, cartilage regeneration can be promoted by a simple technique without requiring an excessive surgical procedure.

When this composition was applied to an articular cartilage defect and a $CaCl_2$ solution was applied to the surface thereof, the composition did not move from the applied site. It was thus surprisingly found that the composition can be applied even at sites subjected to a load under extremely harsh movement conditions in the manner of articular cartilage. As a result of making the viscosity of the composition of the present invention to be about 2000 mPa·s or more, the composition can be applied even if the injured surface is facing downward.

The composition of the present invention allowed the obtaining of extremely superior cartilage regeneration in the case of embedding bone marrow mesenchymal stem cells or stromal cells therein. In addition, even in the case of not embedding these cells, the composition of the present invention was found to allow the obtaining of satisfactory hyaline cartilage regeneration by hyaline chondrocytes, thereby leading to completion of the present invention.

In addition, cartilage degenerative changes were found to be inhibited and cartilage protective effects were found to be obtained by applying to a cartilage injury lesion in an osteoarthritis model a composition containing a monovalent metal salt of alginic acid for which the endotoxin level thereof has been lowered to an extent that does not substantially induce fever or inflammation. Moreover, this composition was also found to have effects that suppress pain in an experimental arthritis pain model, thereby leading to completion of the present invention.

This is the first instance in which a substance other than hyaluronic acid, which is a major component of synovial fluid, has been demonstrated to have compound effects on cartilage tissue in this manner. It was surprising to find that alginic acid, which is a polymer originating in algae and is not inherently present in animals, has effects such as these.

Namely, the present invention provides the following composition for cartilage regeneration that is applied to a cartilage injury lesion.

(1-1) A composition, which is used for cartilage regeneration and which is cured at an affected area by applying to a cartilage injury lesion, containing a low endotoxin monovalent metal salt of alginic acid, having a viscosity of 400 mPa·s to 20000 mPa·s, and having fluidity.

(1-2) The composition described in (1-1) above, wherein the monovalent metal salt of algnic acid is sodium alginate.

(1-3) The composition described in (1-2) above, wherein the sodium alginate is sodium alginate having a weight average molecular weight of 500,000 or more as determined by gel filtration chromatography.

(1-4) The composition described in any of (1-1) to (1-3) above, wherein application to the cartilage injury lesion is either a) application to a cartilage defect, or b) application to holes following formation of one or more of the holes in a cartilage injury lesion or a cartilage defect.

(1-5) The composition described in any of (1-1) to (1-4) above, not containing cells for cartilage tissue regeneration.

(1-6) The composition described in any of (1-1) to (1-4) above, wherein cells are embedded for cartilage tissue regeneration.

(1-7) The composition described in (1-6) above, wherein prior to applying to a cartilage injury lesion, the composition containing a monovalent metal salt of alginic acid having cells embedded therein is embedded with cells cultured in vitro in one or more states selected from the group consisting of a) a state in which the number of cells is $1 \times 10^6$ cells/mL or more, b) a state in which hyaline-like cartilage tissue is detected by Safranin-O staining or H-E staining, c) a state in which type II collagen is detected by anti-collagen II antibody or genetic analysis, d) a state in which aglycan is detected by anti-aglycan antibody or genetic analysis, and e) a state in which the extracellular matrix (collagen, hyaluronic acid, proteoglycan) is secreted.

(1-8) The composition described in (1-6) or (1-7) above, wherein the cells for cartilage tissue regeneration include bone marrow mesenchymal stem cells.

(1-9) The composition described in any of (1-1) to (1-8) above, wherein the composition is adhered to an injured site for at least 5 seconds in the case of applying to a cartilage injury lesion in the state in which an opening in the cartilage defect or an opening of the holes formed in a cartilage injury lesion or cartilage defect is inclined or facing downward.

(1-10) The composition described in any of (1-1) to (1-9) above, wherein application to a cartilage injury lesion is possible with a 16G needle.

(1-11) The composition described in any of (1-1) to (1-10) above, wherein the composition is applied to a cartilage injury lesion, and a crosslinking agent is applied to the surface of the composition.

(1-12) The composition described in (1-11) above, wherein the crosslinking agent is a $CaCl_2$ solution.

(1-13) The composition described in any of (1-1) to (1-12) above, wherein the cartilage injury lesion is injured articular cartilage.

(1-14) The composition described in any of (1-1) to (1-13) above, wherein the cartilage regeneration is for the purpose of regenerating hyaline cartilage.

In addition, the present invention provides a composition allowing the obtaining of therapeutic effects by injecting into a joint of a patient having a cartilage disease.

(2-1) A composition, which is used for treatment of a cartilage disease and which is injected into a joint, containing as an active ingredient thereof a low endotoxin monovalent metal salt of alginic acid.

(2-2) A composition, which is used for inhibition of cartilage degenerative changes and which is injected into a joint, containing as an active ingredient thereof a low endotoxin monovalent metal salt of alginic acid.

(2-3) A composition, which is used for cartilage protection and which is injected into a joint, containing as an active ingredient thereof a low endotoxin monovalent metal salt of alginic acid.

(2-4) A composition, which is used for cartilage repair and which is injected into a joint, containing as an active ingredient thereof a low endotoxin monovalent metal salt of alginic acid.

(2-5) A composition, which is used for suppression of joint pain and which is injected into a joint, containing as an active ingredient thereof a low endotoxin monovalent metal salt of alginic acid.

(2-6) A composition, which is used for inhibition of joint inflammation and which is injected into a joint, containing as an active ingredient thereof a low endotoxin monovalent metal salt of alginic acid.

(2-7) A composition, which is used for improvement of joint function and which is injected into a joint, containing as an active ingredient thereof a low endotoxin monovalent metal salt of alginic acid.

(2-8) A composition, which is used for treatment of osteoarthritis and which is injected into a joint, containing as an active ingredient thereof a low endotoxin monovalent metal salt of alginic acid.

(2-9) A composition, which is used for treatment of frozen shoulder and which is injected into a joint, containing as an active ingredient thereof a low endotoxin monovalent metal salt of alginic acid.

(2-10) A composition, which is used for suppression of joint pain associated with rheumatoid arthritis and which is injected into a joint, containing as an active ingredient thereof a low endotoxin monovalent metal salt of alginic acid.

(2-11) A composition for intra-articular injection having the effect of alleviating, improving or curing symptoms associated with cartilage disease, which contains as an active ingredient thereof a low endotoxin monovalent metal salt of alginic acid.

(2-12) The composition described in (2-11) above, wherein the effect of alleviating, improving or curing symptoms associated with cartilage disease is at least one effect selected from the group consisting of inhibition of cartilage degenerative changes, protection of cartilage, repair of cartilage, suppression of joint pain, inhibition of joint inflammation and improvement of joint function.

(2-13) The composition described in any of (2-1) to (2-12) above, wherein the monovalent metal salt of alginic acid is sodium alginate.

(2-14) The composition described in (2-13) above, wherein the sodium alginate is sodium alginate having a weight average molecular weight of 500,000 or more as determined by gel filtration chromatography.
(2-15) A composition, which is used for treatment of cartilage disease and which is injected into a joint, containing as an active ingredient thereof a low endotoxin sodium alginate having a weight average molecular weight of 500,000 or more as determined by gel filtration chromatography.

Moreover, the present invention also provides the following treatment method for a cartilage injury lesion and a composition used in that treatment method.
(3-1) A method of treating a cartilage injury lesion comprising: applying to a cartilage injury lesion a composition containing a low endotoxin monovalent metal salt of alginic acid, having a viscosity of 400 mPa·s to 20000 mPa·s, and having fluidity.
(3-2) The method described in (3-1) above, wherein the composition containing a monovalent metal salt of alginic acid is applied to a cartilage injury lesion, and a crosslinking agent is applied to the surface of the composition to cure the composition.
(3-3) The method described in (3-1) or (3-2) above, wherein cells for cartilage tissue regeneration are embedded in the composition containing a monovalent metal salt of alginic acid, and the composition is applied to a cartilage injury lesion.
(3-4) The method described in any one of (3-1) to (3-3) above, wherein cells for cartilage tissue regeneration are embedded in the composition containing a monovalent metal salt of alginic acid, and the composition is applied to a cartilage injury lesion after culturing in vitro in one or more states selected from the group consisting of a) a state in which the number of cells is $1 \times 10^6$ cells/mL or more, b) a state in which hyaline-like cartilage tissue is detected by Safranin-O staining or H-E staining, c) a state in which type II collagen is detected by anti-collagen II antibody or genetic analysis, d) a state in which aglycan is detected by anti-aglycan antibody or genetic analysis, and e) a state in which the extracellular matrix (collagen, hyaluronic acid, proteoglycan) is secreted.
(3-5) The method described in any one of (3-2) to (3-4) above, wherein the crosslinking agent is a $CaCl_2$ solution.
(3-6) The method described in any one of (3-1) to (3-5) above, wherein the application to a cartilage injury lesion is either a) application to a cartilage defect, or b) formation of one or more holes in the cartilage injury lesion or a cartilage defect and application to the formed holes.
(3-7) A composition used in the method described in any one of (3-1) to (3-6) above, containing a low endotoxin monovalent metal salt of alginic acid, having a viscosity of 400 mPa·s to 20000 mPa·s, and having fluidity.
(3-8) The composition described in (3-7) above, wherein the composition containing a monovalent metal salt of alginic acid contains cells for cartilage tissue regeneration.
(3-9) The composition described in (3-7) or (3-8) above, wherein the monovalent metal salt of alginic acid is sodium alginate.
(3-10) A composition for treating a cartilage injury lesion, containing a monovalent metal salt of alginic acid for which the endotoxin level thereof has been lowered to an extent that does not substantially induce inflammation or fever, having a viscosity of 400 mPa·s to 20000 mPa·s and having fluidity, wherein the composition is arthroscopically used by applying so as to fill sufficiently the void volume of an affected area which is an application site of a cartilage injury lesion which has been irrigated and dried in advance, a $CaCl_2$ solution is applied to the surface of the applied composition followed by removing the $CaCl_2$ solution remaining on the surface of the applied composition, and the composition is cured at the affected area.

Moreover, the present invention provides a treatment method for cartilage disease and symptoms associated therewith.
(4-1) A method of treating a cartilage disease comprising: injecting into a joint a composition containing as an active ingredient thereof a low endotoxin monovalent metal salt of alginic acid.
(4-2) A method of inhibiting cartilage degenerative changes comprising: injecting into a joint a composition containing as an active ingredient thereof a low endotoxin monovalent metal salt of alginic acid.
(4-3) A method of protecting cartilage comprising: injecting into a joint a composition containing as an active ingredient thereof a low endotoxin monovalent metal salt of alginic acid.
(4-4) A method of repairing cartilage comprising: injecting into a joint a composition containing as an active ingredient thereof a low endotoxin monovalent metal salt of alginic acid.
(4-5) A method of suppressing joint pain comprising: injecting into a joint a composition containing as an active ingredient thereof a low endotoxin monovalent metal salt of alginic acid.
(4-6) A method of inhibiting joint inflammation comprising: injecting into a joint a composition containing as an active ingredient thereof a low endotoxin monovalent metal salt of alginic acid.
(4-7) A method of improving joint function comprising: injecting into a joint a composition containing as an active ingredient thereof a low endotoxin monovalent metal salt of alginic acid.
(4-8) A method of treating osteoarthritis comprising: injecting into a joint a composition containing as an active ingredient thereof a low endotoxin monovalent metal salt of alginic acid.
(4-9) A method of treating frozen shoulder comprising: injecting into a joint a composition containing as an active ingredient thereof a low endotoxin monovalent metal salt of alginic acid.
(4-10) A method of suppressing joint pain associated with rheumatoid arthritis comprising: injecting into a joint a composition containing as an active ingredient thereof a low endotoxin monovalent metal salt of alginic acid.
(4-11) The method described in any of (4-1) to (4-10) above, wherein the monovalent metal salt of alginic acid is sodium alginate.
(4-12) The method described in (4-11) above, wherein the sodium alginate is sodium alginate having a weight average molecular weight of 500,000 or more as determined by gel filtration chromatography.
(4-13) A method for treating a cartilage disease comprising: injecting into a joint a composition containing as an active ingredient thereof a low endotoxin sodium alginate having a weight average molecular weight of 500,000 or more as determined by gel filtration chromatography.

Effects of the Invention

Since the composition for regenerating cartilage of the present invention can be injected into a cartilage injury lesion without requiring an excessive surgical procedure, the procedure is simple. Cartilage regeneration, and particularly hyaline cartilage regeneration, can be effectively promoted without placing an excessive burden on the body in terms of harvesting chondrocytes, periosteum and the like.

The composition for regenerating cartilage of the present invention has gel curability as a result of being contacted with Ca ions at the affected area. The composition can be retained at the affected area by curing the surface thereof as a result of taking advantage of this property. In the case of embedding cells for cartilage tissue regeneration in the composition of the present invention, the cells are easily dispersed in the cured gel. Thus, the composition can be used for various forms of cartilage injuries, and is able to accommodate various application conditions.

The composition for treating a cartilage disease of the present invention is able to demonstrate therapeutic effects on a wide-ranging cartilage injury lesion by injecting into a joint in a liquid state. The composition demonstrates at least one effect selected from the group consisting of repair of cartilage at a cartilage injury lesion as observed in, for example, aging, trauma, osteoarthritis, disc injury, meniscus injury or osteochondritis dissecans, inhibition of cartilage degenerative changes, and protection of cartilage.

In addition, the composition for treating a cartilage disease of the present invention has the effect of inhibiting joint inflammation and suppressing pain associated with inflammation. The composition demonstrates analgesic action by inhibiting joint inflammatory responses in, for example, osteoarthritis, frozen shoulder and rheumatoid arthritis.

The composition for treating a cartilage disease of the present invention is able to inhibit the progression of cartilage disease and alleviate or cure symptoms by demonstrating reparative, protective and degeneration inhibitory effects on mechanical injuries to cartilage, while also inhibiting inflammatory responses and pain in joint tissue. In particular, the composition is useful for treating osteoarthritis, treating frozen shoulder and alleviating joint pain associated with rheumatoid arthritis.

BRIEF DESCRIPTION OF THE DRAWINGS

FIG. 4 shows photographs of the results of staining during in vitro culturing of Example 6. (A) Purified sodium alginate—21 days of culturing; (B) purified sodium alginate—28 days of culturing; (C) food grade sodium alginate—21 days of culturing; (D) food grade sodium alginate—28 days of culturing. Staining was carried out with, moving from left to right, H-E stain, Safranin-O stain, anti-type I, anti-type II and anti-type X anti-collagen antibodies.

FIG. 5 shows photographs depicting images obtained during a procedure in a rabbit cartilage repair model of Example 7.

FIG. 6 is a chart showing the criteria for scoring overall observations in a rabbit cartilage repair model of Example 7.

FIG. 7 is a chart showing the criteria for scoring the results of staining in a rabbit cartilage repair model of Example 7.

FIG. 8 shows photographs of tissue staining of a control group A) (empty) in a rabbit cartilage repair model of Example 7. FIG. 8A shows the results after 4 weeks while FIG. 8B shows the results after 12 weeks. The results are shown for, moving from left to right, H-E staining, Safranin-O staining and type I collagen and type II collagen immunostaining.

FIG. 9 shows photographs of tissue staining of a food grade alginate+cells group C) in a rabbit cartilage repair model of Example 7. FIG. 9A shows the results after 4 weeks while FIG. 9B shows the results after 12 weeks. The staining methods are the same as those of FIG. 8.

FIG. 10 shows photographs of tissue staining of a purified alginate (no cells) group D) in a rabbit cartilage repair model of Example 7. FIG. 10A shows the results after 4 weeks while FIG. 10B shows the results after 12 weeks. The staining methods are the same as those of FIG. 8.

FIG. 11 shows photographs of tissue staining of a purified alginate+cells group E) in a rabbit cartilage repair model of Example 7. FIG. 11A shows the results after 4 weeks while FIG. 11B shows the results after 12 weeks. The staining methods are the same as those of FIG. 8.

FIG. 12 shows the results of scoring overall observations and staining in a rabbit cartilage repair model of Example 7.

FIG. 14 shows photographs obtained during an experiment on a cadaver model of Example 8.

SEQUENCE LISTING FREE TEXT

Figure 1:
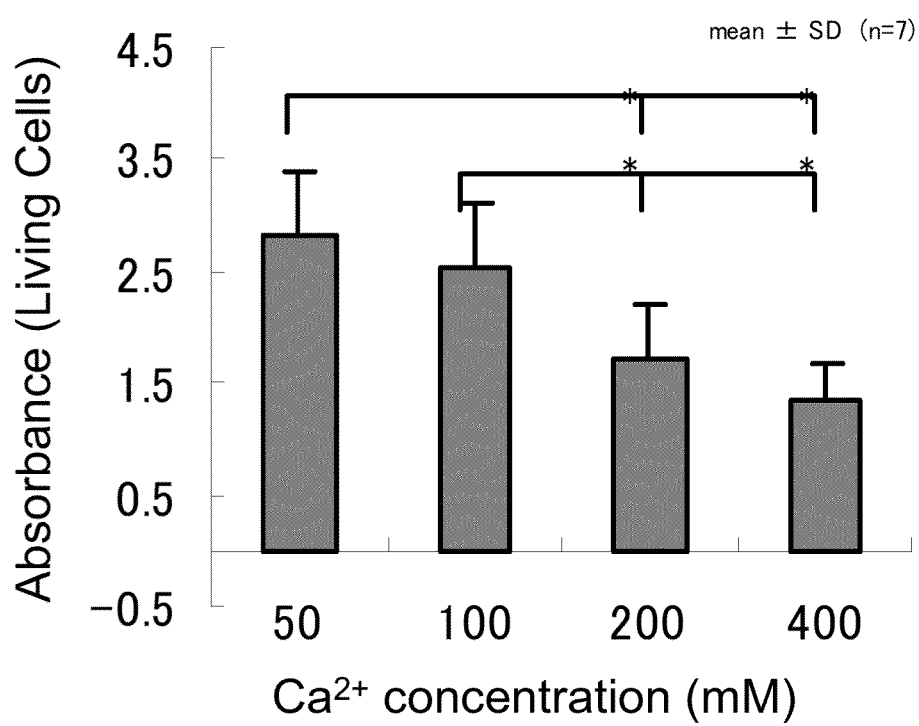
FIG. 1 is a graph showing the survival rates of cells versus the concentration of various $CaCl_2$ solutions (Example 4).

SEQ ID NO:1: Synthetic DNA
SEQ ID NO:2: Synthetic DNA
SEQ ID NO:3: Synthetic DNA
SEQ ID NO:4: Synthetic DNA
SEQ ID NO:5: Synthetic DNA
SEQ ID NO:6: Synthetic DNA
SEQ ID NO:7: Synthetic DNA
SEQ ID NO:8: Synthetic DNA
SEQ ID NO:9: Synthetic DNA
SEQ ID NO:10: Synthetic DNA

BEST MODE FOR CARRYING OUT THE INVENTION

Although the following provides a detailed explanation of the present invention, the following embodiments are intended to be exemplary for explaining the present invention, and the present invention can be carried out in various forms without deviating from the purport thereof.

1. Introduction

"Cartilage" is found in joints; thoracic wall; intervertebral discs; meniscus; tubular structure such as throat, respiratory tract and ears and so on, and is classified into three types consisting of hyaline cartilage, elastic cartilage and fibrous cartilage. For example, articular cartilage is classified as hyaline cartilage, is composed of chondrocytes, collagenous extracellular matrix, proteoglycan and water, and is free of vascular intervention. Hyaline cartilage is rich in type II collagen, and is stained by type II collagen antibodies. It is also characterized by being stained red by safranin-O stain used to stain proteoglycan. A "cartilage injury" refers to a state in which the cartilage has been damaged due to aging, trauma or other factors, and includes a state in which cartilage function has decreased, such as a decrease in the characteristic viscoelasticity of cartilage (which enables cartilage to slowly compress when subjected to a load and then slowly return to its original state when the load is removed) thereby bringing about impairment of the ability of the cartilage to support a load while maintaining mobility. Cartilage injury is observed in diseases such as osteoarthritis and rheumatoid arthritis. The present invention relates to curable composition for regenerating cartilage that can be applied to such a cartilage injury lesion. A "cartilage defect" refers to a cartilage injury lesion in which a portion of the cartilage is missing, and indicates a void in cartilage tissue and the surrounding tissue that forms the void. The composition of the present invention is preferably used for the treatment of a "cartilage defect".

More specifically, the present invention is a composition for regenerating cartilage that is applied to a cartilage injury lesion, contains a monovalent metal salt of alginic acid for which the endotoxin level thereof has been lowered to an extent that does not substantially induce fever or inflammation, and has the viscosity of 400 to 20000 mPa·s.

Consequently, since the composition of the present invention is able to effectively promote cartilage regeneration at an affected area, demonstrate satisfactory adherence to the cartilage injury lesion and can be applied with a syringe and the like, it is easily applied to a cartilage injury lesion.

In the present invention, "cartilage regeneration" or "cartilage tissue regeneration" refers to restoring the function of a cartilage injury lesion for which cartilage function has been impaired or lost. In the present invention, restoration of function does not necessarily require that function be completely restored, rather that function be restored to a greater degree than the state of the cartilage injury lesion prior to application of the present composition. In the case of assigning a value of 100% to the state of normal cartilage prior to injury and assigning a value of 0% to the state of cartilage injury prior to application of the present composition, cartilage function is preferably restored to 30% or more thereof, more preferably to 50% or more thereof, even more preferably to 80% or more thereof, and particularly preferably to a state nearly equivalent to that prior to injury. The proportion of cartilage other than hyaline cartilage, such as fibrous cartilage, in the regenerated cartilage is preferably low. In addition, "treatment of a cartilage injury lesion" or "treatment of a cartilage defect" refers to alleviating or curing symptoms thereof by regenerating cartilage in cartilage injury lesions or cartilage defects observed in aging, trauma, osteoarthritis, disc injury or meniscus injury, oseteochondrosis dissecans and the like.

In addition, "application to a cartilage injury lesion" refers to use of a composition for regenerating cartilage and the like by contacting with a cartilage injury lesion, and preferably the use of the composition of the present invention by injecting into a cartilage defect to fill in that cartilage defect. Alternatively, the composition of the present invention may be used by further forming one or more comparatively small holes in a cartilage injury lesion, and preferably a cartilage defect, and injecting the composition of the present invention into the holes to fill in the holes. The application to the cartilage injury lesion is preferably performed such that the void volume of an affected area is filled sufficiently. The affected area is preferably subjected to required pretreatment and irrigated as necessary prior to application of the present composition. Irrigation of the affected area refers to using physiological saline, for example, to remove blood components and other unnecessary tissue and the like at the site where the composition of the present invention is to be applied. Following irrigation, the affected area is preferably dried by, for example, wiping off any remaining unnecessary fluid components and the like followed by applying the composition of the present invention.

In the present invention, "cartilage disease" refers to a disease that occurs due to cartilage, cartilage tissue and/or joint tissue (such as the synovial membrane, articular capsule or subchondral bone) having been injured by mechanical irritation or inflammatory response. "Cartilage disease treatment" refers to alleviating, improving and/or curing various symptoms of tissue that has been injured by mechanical irritation or inflammatory response. For example, in cases of osteoarthritis, there is compound occurrence of symptoms such as articular cartilage wear, degeneration of cartilage tissue, inflammation of the synovial membrane or pain associated with inflammation. On the other hand, in cases of frozen shoulder, symptoms primarily consist of inflammation of the synovial membrane and articular capsule as well as pain associated therewith, while cartilage wear and degeneration may not be observed. Although the mechanism of occurrence of rheumatoid arthritis is not fully understood, synovial tissue and cartilage tissue are thought to be destroyed by inflammatory cytokines resulting from an autoimmune response. In this manner, cartilage disease is a disease that presents with compound symptoms, and drugs for the treatment thereof are required to have compound effects, including protection of cartilage from wear, inhibition of degenerative changes in cartilage due to wear or inflammation, repair of cartilage injury lesions and inhibition of inflammation and pain. The "composition containing a low endotoxin monovalent metal salt of alginic acid" of the present invention has the effects of protecting cartilage from mechanical irritation, inhibiting degenerative changes in cartilage caused by wear or inflammation, repairing cartilage injury lesions and inhibiting inflammation and pain of joint tissue. As a result, the composition is able to inhibit the progress of cartilage disease, and alleviate, improve and/or cure symptoms. In particular, the composition is useful for treating osteoarthritis, treating frozen shoulder and alleviating joint pain associated with rheumatoid arthritis.

In addition, "injecting into a joint" refers to injection of a liquid composition having fluidity into, for example, an articular cavity, synovial bursa or peritenon. In the case of using to treat osteoarthritis, the composition is preferably injected into an articular cavity. Furthermore, although osteoarthritis can occur in various joints of the body, including those of the knees, shoulders, hips, lower back, ankles, wrists and fingers, the composition of the present invention can be applied to any of these joints.

2. Monovalent Metal Salt of Alginic Acid

The "monovalent metal salt of alginic acid" contained in the composition for regenerating cartilage or treating a cartilage disease of the present invention is a water-soluble salt formed by ion exchange between a hydrogen atom of carboxylic acid at position 6 of alginic acid and a monovalent metal ion such as $Na^+$ or $K^+$. Although specific examples of monovalent metal salts of alginic acid include sodium alginate and potassium alginate, sodium alginate acquirable as a commercially available product is particularly preferable. A solution of a monovalent metal salt of alginic acid forms a gel when mixed with a crosslinking agent.

The "alginic acid" used in the present invention is a biodegradable, high molecular weight polysaccharide that is a polymer obtained by linearly polymerizing two types of uronic acids in the form of D-mannuronic acid (M) and L-glucuronic acid (G). More specifically, the alginic acid is a block copolymer in which a homopolymer fraction of D-mannuronic acid (MM fraction), homopolymer fraction of L-glucuronic acid (GG fraction) and fraction in which D-mannuronic acid and L-glucuronic acid are randomly arranged (MG fraction) are linked arbitrarily. The composite ratio of the D-mannuronic acid to the L-glucuronic acid of the alginic acid (M/G ratio) mainly varies according to the type of algae or other organism serving as the origin thereof, is affected by the habitat and season of that organism, and extends over a wide range from a high G type having an M/G ratio of about 0.4 to a high M type having an M/G ratio of about 5.

A monovalent metal salt of alginic acid is a polysaccharide, and although it is difficult to accurately determine molecular weight, it generally has a weight average molecular weight of 10,000 to 10,000,000 and preferably 50,000 to 3,000,000. Since the effect of regenerating cartilage at cartilage injury lesions, and particularly the effect of regenerating hyaline cartilage, becomes inferior if the molecular weight is excessively low, the monovalent metal salt of alginic acid used in the present invention preferably has a weight average molecular weight of 500,000 or more. In particular, sodium alginate having a weight average molecular weight of 500,000 or more has the unexpected effect of regenerating hyaline cartilage even in the state of not containing embedded cells, and is suitable for use as a composition for cartilage regeneration. In addition, since this cartilage regeneration effect also advantageously contributes to repair of cartilage injury lesions in cartilage disease, it is also suitable for use as a composition for treating a cartilage disease. In actuality, superior therapeutic effects were observed for high molecular weight alginic acid as compared with low molecular weight alginic acid in a rabbit OA model. Sodium alginate having a weight average molecular weight of 1,000,000 and 1,700,000 as determined by gel filtration chromatography demonstrated superior cartilage degenerative change inhibitory effects, cartilage protective effects and cartilage repair effects as compared with sodium alginate having a molecular weight of 410,000. In the case of calculating the molecular weight of a polysaccharide by gel filtration chromatography, there is normally the potential for measurement error of 10 to 20%. For example, a molecular weight of 400,000 can fluctuate within the range of 320,000 to 480,000, a molecular weight of 500,000 can fluctuate within the range of 400,000 to 600,000, and a molecular weight of 1,000,000 can fluctuate within the range of 800,000 to 1,200,000. Thus, the preferable weight average molecular weight range of a monovalent metal salt of alginic acid for which effects on cartilage are particularly superior is at least 500,000 or more, more preferably 650,000 or more, and even more preferably 800,000 or more. In addition to production being difficult, since problems occur such as viscosity when preparing an aqueous solution being excessively high or solubility decreasing if the molecular weight is excessively high, the weight average molecular weight is preferably 5,000,000 or less and more preferably 3,000,000 or less.

Since high molecular weight substances derived from a natural origin typically do not have a single molecular weight, but rather consist of an aggregate of molecules having various molecular weights, molecular weight is measured in the form of a molecular weight distribution having a certain range. A typical measurement technique is gel filtration chromatography. Typical examples of information obtained from molecular weight distribution as determined by gel filtration chromatography include weight average molecular weight (Mw), number average molecular weight (Mn) and variance ratio (Mw/Mn).

Weight average molecular weight emphasizes the contribution of average molecular weight of polymers having a large molecular weight, and is represented with the following formula:

$$Mw = \Sigma(WiMi)/W = \Sigma(HiMi)/\Sigma(Hi)$$

Number average molecular weight is calculated by dividing the total weight of polymers by the total number of polymers.

$$Mn = W/\Sigma Ni = \Sigma(MiNi)/\Sigma Ni = \Sigma(Hi)/\Sigma(Hi/Mi)$$

Here, W represents the total weight of all polymers, Wi represents the weight of the ith polymer, Mi represents molecular weight at an ith elution time, Ni represents the number of molecular weights Mi, and Hi represents the height at the ith elution time.

Since cartilage regeneration effects (and particularly hyaline cartilage regeneration effects) at cartilage injury lesions, cartilage repair effects, effects inhibiting cartilage degenerative changes and/or cartilage protective effects in the treatment of cartilage disease are considered to be largely contributed to by molecular species having large molecular weights, weight average molecular weight may be used as an indicator of molecular weight.

Differences in values according to the measurement method are known to occur in the measurement of molecular weights of high molecular weight substances derived from a natural origin (example of hyaluronic acid: Chikako Yomota et al., Bull. Natl. Health Sci., Vol. 117, pp. 135-139 (1999), Chikako Yomota et al., Bull. Natl. Health Sci., Vol. 121, pp. 30-33 (2003)). Methods for measuring the molecular weight of alginate described in the literature include a method in which molecular weight is calculated from intrinsic viscosity, and a method in which molecular weight is calculated by Size Exclusion Chromatography with Multiple Angle Laser Light Scattering Detection (SEC-MALLS) (ASTM F2064-00 (2006), published by ASTM International). Furthermore, it is also described in the literature that in the measurement of molecular weight by size exclusion chromatography (gel filtration chromatography), calculation from a calibration curve using pullulan for the standard substance is insufficient, and it is recommended that measurement of molecular weight be used in combination with multiple angle laser light scattering detector (MALLS) (namely, measurement by SEC-MALLS). In addition, there are also examples of the use of molecular weights determined by SEC-MALLS being used as catalog specifications of alginates (FMC Biopolymer Inc., PRONOVA™ Sodium Alginates Catalog).

The inventors of the present invention found there to be differences in the therapeutic effects of sodium alginate having different molecular weights in an OA model, and measured the molecular weights of these alginates by gel filtration chromatography and SEC-MALLS. As a result, molecular weights determined by gel filtration chromatography were determined to demonstrate a higher correlation with viscosity and therapeutic effects of the alginates. Namely, it was newly found that rather than the generally recommended SEC-MALLS method, molecular weight determined by gel filtration chromatography was found to be suitable as a parameter for specifying the preferable molecular weight range of alginates used in a composition for cartilage regeneration or treatment of cartilage disease. Thus, in the case of specifying the molecular weight of an alginate in the present specification, that molecular weight is the weight average molecular weight as calculated by gel filtration chromatography unless specifically stated otherwise.

The preferable conditions for gel filtration chromatography as indicated in the examples. A typical condition consists of the use of a calibration curve using pullulan for the standard substance. Pullulan having a molecular weight of at least 1,600,000, 788,000, 404,000, 212,000 and 112,000 is preferably used for the pullulan used for the standard substance. In addition, the eluate (200 mM sodium nitrate solution), column conditions and the like can also be specified. Column conditions preferably consist of using polymethacrylate resin-based filler and using at least one column having a molecular weight cutoff of 10,000,000 or more. A typical example of a column is the TSKgel GMPWx1 (diameter: 7.8 mm×300 mm) (Tosoh Corp.).

Although a monovalent metal salt of alginic acid has a large molecular weight and high viscosity when initially isolated from brown algae, molecular weight decreases and viscosity lowers during the course of undergoing heat-drying, freeze-drying, purification and the like. Thus, monovalent metal salts of algninic acid having different molecular weights can be produced by suitably controlling the temperature in each step of production. Monovalent metal salts of alginic acid having a high molecular weight are obtained by controlling the temperature in each of step of production to be somewhat low, while monovalent metal salts of alginic acid having a low molecular weight are obtained by controlling the temperature in each step of production to be somewhat high. In addition, monovalent metal salts of alginic acid having different molecular weights can also be produced by a technique such as suitably selecting the brown algae used for the raw material, or fractionating according to molecular weight in the production process. Moreover, a monovalent metal salt of alginic acid having a target molecular weight can also be obtained by mixing a monovalent metal salt of alginic acid produced according to various production processes with a different lot of monovalent metal salt of alginic acid having a different molecular weight or viscosity after having measured the molecular weight or viscosity thereof.

Although the alginic acid used in the present invention may be of a natural origin or synthetic, it is preferably derived from a natural origin. Examples of naturally-occurring alginic acids include those extracted from brown algae. Although brown algae containing alginic acid are prominently found along seacoasts throughout the world, algae that can actually be used as raw materials of alginic acid are limited, with typical examples thereof including *Lessonia* species found in South America, *Macrocystis* species found in North America, *Laminaria* and *Ascophyllum* species found in Europe, and *Durvillea* species found in Australia. Examples of brown algae serving as raw materials of alginic acid include *Lessonia* species, *Macrocystis* species, *Laminaria* species, *Ascophyllum* species, *Durvillea* species, *Eisenia* species and *Ecklonia* species.

3. Endotoxin Reduction Treatment

The monovalent metal salt of alginic acid contained in the composition for cartilage regeneration or treatment of a cartilage disease of the present invention is a low endotoxin monovalent metal salt of alginic acid. Low endotoxin refers to that in which the endotoxin level thereof has been substantially lowered to an extent that does not induce inflammation or fever. Namely, the monovalent metal salt of alginic acid has been subjected to endotoxin reduction treatment. It was surprisingly found that by subjecting to this endotoxin reduction treatment, in addition to being able to enhance the cartilage regenerative action of the composition when applied to a cartilage injury lesion, the regeneration of subchondral bone can be promoted and mechanical strength of the affected area can be enhanced. Namely, by using low endotoxin alginic acid in the composition of the present invention, a composition can be obtained having high bioaffinity, and not inducing degeneration and inflammatory responses in surrounding cartilage.

Endotoxin reduction treatment can be carried out by a known method or a method complying therewith. For example, this treatment can be carried out by the method of Suga et al. involving purification of sodium hyaluronate (see, for example, Japanese Patent Application Laid-open No. H9-324001), the method of Yoshida et al. involving purification of β1,3-glucan (see, for example, Japanese Patent Application Laid-open No. H8-269102), the method of William et al. involving purification of a biopolymer such as alginate or gellan gum (see, for example, Published Japanese Translation No. 2002-530440 of PCT International Publication), the method of James et al. involving purification of polysaccharide (see, for example, International Publication No. 93/13136 pamphlet), the method of Lewis et al. (see, for example, U.S. Pat. No. 5,589,591), the method of Hermanfranck et al. involving purification of alginate (see, for example, Appl. Microbiol. Biotechnol. (1994), 40:638-643) or a method complying therewith. The endotoxin reduction treatment of the present invention is not limited thereto, but rather can be carried out by a known method such as cleaning, purification using filtration with filter (endotoxin removing filter or electrification filter), ultrafiltration or a column (such as an endotoxin adsorption affinity column, gel filtration column or ion exchange column), adsorption to a hydrophobic substance, resin or activated carbon and the like, organic solvent treatment (such as extraction with an organic solvent or precipitation or deposition by addition of organic solvent), surfactant treatment (see, for example, Japanese Patent Application Laid-open No. 2005-036036) or a suitable combination thereof. A known method such as centrifugal separation may be suitably combined with these treatment steps. Endotoxin reduction treatment is preferably suitably selected according to the type of alginic acid.

Endotoxin level can be confirmed by a known method, and can be measured using a known method such as a method using a limulus reagent (LAL) or method using an Endospecy (registered trademark) ES-24S set (Seikagaku Corp.). Although there are no particular limitations on the endotoxin treatment method of the alginic acid contained in the composition of the present invention, the endotoxin content of the monovalent metal salt of alginic acid in the case of measuring endotoxin using a limulus reagent (LAL) is preferably 500 endotoxin units (EU)/g or less, more preferably 100 EU/g or less, even more preferably 50 EU/g or less and particularly preferably 30 EU/g or less as a result thereof. Sodium alginate that has undergone endotoxin reduction treatment can be acquired as a commercially available products such as Sea Matrix (sterilized) (Kimica Corp., Mochida International Ltd.) and Pronova™ UP LUG (FMC).

4. Preparation of Solution of Monovalent Metal Salt of Alginic Acid

The composition for regenerating cartilage or treating a cartilage disease may be prepared by using a solution of a monovalent metal salt of alginic acid. The solution of a monovalent metal salt of alginic acid can be prepared by a known method or method complying therewith. Namely, the monovalent metal salt of alginic acid used in the present invention can be produced by a known method such as an acid method or calcium method using the previously described brown algae. More specifically, after extracting from these brown algae using an alkaline aqueous solution such as aqueous sodium carbonate solution, for example, alginic acid be obtained by adding an acid (such as hydrochloric acid or sulfuric acid), and a salt of alginic acid can be obtained by ion exchange of the alginic acid. Endotoxin reduction treatment is then carried out as previously described. There are no particular limitations on the solvent of the alginic acid salt provided it is a solvent that can be applied in vivo, and examples of such solvents include purified water, distilled water, ion exchange water, Milli-Q water, physiological saline and phosphate-buffered saline (PBS). These are preferably sterilized and preferably subjected to endotoxin reduction treatment. For example, Milli-Q water can be used after sterilizing by filtration. The composition of regenerating cartilage or treating a cartilage disease of the present invention can also be obtained by, for example, mixing a monovalent metal salt of alginic acid into a medium containing cells without dissolving the monovalent metal salt of alginic acid in the above-mentioned solvent. In addition, the procedure for obtaining the composition of the present invention is preferably carried out in an environment having low levels of endotoxins and bacteria. For example, the procedure is preferably carried out on a clean bench using sterilized apparatuses, and the apparatuses used may be treated with a commercially available endotoxin removal agent.

In the case of producing a composition as described above using a monovalent metal salt of alginic acid that has been purified to a preferable endotoxin level, the endotoxin content of the composition is normally 500 EU/g or less, more preferably 300 EU/g or less and particularly preferably 150 EU/g or less.

5. Viscosity of Composition for Regenerating Cartilage or Treating a Cartilage Disease Although there are no particular limitations on the viscosity of the composition for regenerating cartilage of the present invention provided the effects of the present invention are obtained, it is preferably 400 to 20000 mPa·s. The composition of the present invention can be adjusted to a suitable viscosity by using, for example, the above-mentioned solvent. If viscosity is within this range, adherence to a cartilage injury lesion is favorable and the composition can be injected into an articular cavity or cartilage injury lesion with a syringe and the like. In addition, if the viscosity of the composition for regenerating cartilage is about 2000 mPa·s or more, adherence to a cartilage injury lesion is further improved, and if the viscosity is about 5000 mPa·s or more in particular, even if the opening of a cartilage defect is facing downward such as in the case of arthroscopically manipulating a cartilage injury on the surface of a human femoral joint, for example, the composition of the present invention can be contacted with the surface of the cartilage injury lesion by injecting the composition of the present invention into the cartilage defect and allowing to adhere thereto for at least one minute in the absence of fixation. The surface of the composition can be fixated as necessary during the time it is adhering. Adherence to the cartilage injury lesion further improves as viscosity increases, and in the case of a viscosity of 10000 mPa·s, for example, the composition can be adhered without fixation for a longer period of time in comparison with a viscosity of 5000 mPa·s. Thus, in the case the composition of the present invention is applied to a cartilage injury lesion in the state in which an opening of a cartilage defect or an opening of a hole formed in a cartilage injury lesion or cartilage defect is inclined or facing downward, the composition of the present invention adheres to the cartilage injury lesion for at least 5 seconds, preferably for at least 10 seconds, more preferably for at least 30 seconds and particularly preferably for at least 1 minute without using a fixation means. As a result of adjusting the viscosity thereof, the composition of the present invention can secure enough time until a fixation means is applied to the surface of the composition. Here, "adherence to a cartilage injury lesion" refers to the composition of the present invention being retained in the cartilage injury lesion without coming out there from. In this manner, as a result of adjusting the viscosity thereof, the composition of the present invention offers the advantage of allowing treatment to be performed by a simple procedure in the form of injection even if the affected area is positioned such that it is difficult to perform treatment by a surgeon such as when the affected area is facing downward.

On the other hand, the composition of the present invention is injected easier with a syringe and the like when the viscosity thereof is about 20000 mPa·s or less. Although the composition can be injected with a syringe and the like even if, for example, the viscosity thereof is about 20000 mPa·s, in cases when injection is difficult due to excessively high viscosity, the composition of the present invention may be applied to the surface of a cartilage injury lesion using another means. From the viewpoint of ease of manipulating the syringe, the viscosity of the composition of the present invention is preferably 20000 mPa·s or less, and more preferably 15000 mPa·s or less. Thus, the viscosity of the composition of the present invention applied to a cartilage injury lesion in the state in which an opening of a cartilage defect or an opening of a hole formed in a cartilage injury lesion or cartilage defect is inclined or facing downward is preferably about 2000 mPa·s or more from the viewpoint of adherence, preferably about 20000 mPa·s or less from the viewpoint of handling ease of the composition, and preferably 3000 to 15000 mPa·s, more preferably 4000 to 10000 mPa·s, and particularly preferably 5000 to 6000 mPa·s.

If the viscosity of the composition of the present invention is about 400 mPa·s or more, the composition is able to adequately demonstrate the effects of the present invention by being applied to a cartilage injury lesion. For example, in the case of being able to work the present invention in the state in which the side containing an opening of a cartilage defect is facing upward, the composition of the present invention can be injected into the cartilage injury lesion to contact the composition of the present invention with the surface of the cartilage injury lesion followed by fixating the surface of the composition. Injection with a syringe and the like can be carried out easily due to the low viscosity of the composition. In the case the viscosity of the composition is about 5000 mPa·s, for example, the composition can be applied to the entire cartilage injury lesion by forming one or more extremely small holes in the cartilage injury lesion such as in the case there is residual cartilage at the site of the cartilage injury lesion.

Although there are no particular limitations on viscosity in the case of injecting the composition for treating a cartilage disease of the present invention into a joint provided therapeutic effects on cartilage disease are obtained, the viscosity is preferably 100 to 20000 mPa·s. The viscosity is preferably 200 to 15000 mPa·s, more preferably 400 to 10000 mPa·s, and particularly preferably 1000 to 6000 mPa·s. The use of a suitable viscosity makes it possible to demonstrate the effect of compensating for cushioning function of synovial fluid, thereby making it possible to demonstrate the effect of treating a cartilage disease in a state of being dispersed in synovial fluid.

The viscosity of the composition for regenerating cartilage or treating a cartilage disease can be adjusted by, for example, controlling the concentration of alginic acid in the solution of a monovalent metal salt of alginic acid or controlling the molecular weight of the alginic acid.

The viscosity of the solution of the monovalent metal salt of alginic acid increases when the concentration of alginic acid in the solution is high and decreases when the concentration of alginic acid in the solution is low. Although unable to be stated unequivocally as a result of being affected by molecular weight, the preferable concentration of alginic acid in the solution of the monovalent metal ion of alginic acid is roughly 1 to 5% w/v, more preferably 1.5 to 3% w/v and particularly preferably 2 to 2.5% w/v.

The monovalent metal salt of alginic acid initially has a high molecular weight and increased viscosity when extracted from brown algae even though the concentration is constant, the molecular weight decreases during the course of heat drying, freeze drying, purification and the like, eventually resulting in the viscosity being somewhat low. Viscosity constantly varies even for alginic acid extracted from the same brown algae. In addition, measured values of viscosity also vary according to the measuring instrument and measurement conditions. Thus, a solution of a monovalent metal salt of alginic acid having superior adherence to a cartilage injury lesion and for which the endotoxin level thereof has been lowered is included within the scope of the present invention.

A monovalent metal salt of alginic acid having a high molecular weight can be selected to obtain a composition having superior adherence to an affected area and high viscosity from a solution of a monovalent metal salt of alginic acid having a low concentration.

Since the viscosity of the solution of a monovalent metal salt of alginic acid is affected by the M/G ratio, an alginic acid can be suitably selected that has an M/G ratio more preferable for viscosity of the solution and the like. The M/G ratio of alginic acid used in the present invention is about 0.4 to 4.0, preferably about 0.8 to 3.0 and more preferably about 1.0 to 1.6.

As previously described, since the M/G ratio is determined primarily by the type of algae, the type of brown algae used for the raw material has an effect on the viscosity of the solution of the monovalent metal salt of alginic acid. The alginic acid used in the present invention is preferably derived from brown algae of the genii *Lessonia, Macrocystis, Laminaria, Ascophyllum* and *Durvillea*, more preferably derived from brown algae of the genii *Lessonia*, and particularly preferably brown algae of *Lessonia nigrescens*.

In addition, the viscosity of the composition can be adjusted by, for example, the amount of embedded cells (refer to the description below) present in the solution of the monovalent metal salt of alginic acid. In the case the composition of the present invention has embedded cells, the viscosity of the composition of the present invention is preferably adjusted based on the viscosity of the composition after the cells have been embedded. However, in the case of using with embedded cells in the actual clinical setting, it is difficult to deploy a step for adjusting viscosity after the cells have been embedded. Thus, in the case the composition of the present invention has embedded cells, the viscosity of the composition prior to embedding the cells may be taken to be the viscosity of the composition of the present invention.

One aspect of the composition of the present invention is a composition for regenerating cartilage by applying to a cartilage injury lesion in which bone marrow mesenchymal stem cells and/or bone marrow mesenchymal stromal cells are embedded in a composition containing a monovalent metal salt of alginic acid for which the endotoxin level thereof has been lowered to an extent that does not substantially induce fever or inflammation, having the viscosity of 400 to 20000 mPa·s, and having fluidity.

6. Embedded Cells

The composition for regenerating cartilage or treating a cartilage disease of the present invention can embed cells for regenerating cartilage tissue in a composition containing a monovalent metal salt of alginic acid, and preferably can embed cells for regenerating cartilage tissue in a solution of a monovalent metal salt of alginic acid. The term "embed" as used in the present invention refers to suspending cells for regenerating cartilage tissue in a composition containing a monovalent metal salt of alginic acid, and preferably suspending cells for generating cartilage tissue in a solution of a monovalent metal salt of alginic acid. As a result, cartilage regeneration can be more effectively promoted and the strength of cartilage to which the composition of the present invention has been applied can be further enhanced. Preferably, the cells are dispersed in the composition of the present invention. Although examples of such cells include stem cells and stromal cells, and there are no particular limitations on the origin thereof, examples of which include bone marrow, adipocytes and umbilical cord blood. These cells are preferably bone marrow mesenchymal stem cells or bone marrow mesenchymal stromal cells. Other examples include cartilage precursor cells, chondrocytes, synoviocytes, erythropoietic stem cells and ES cells. One or more of these cells can be embedded. Since "stem cells" in particular have self-regeneration and multiple differentiation abilities, using these stem cells to regenerate cartilage allows the regeneration of histologically superior cartilage having superior mechanical strength. Although stem cells include embryonic stem cells and bone marrow mesenchymal stem cells, since bone marrow mesenchymal stem cells allow the use of adult autologous cells, they are acquired easily and suitable for use for cartilage regeneration. In addition, since bone marrow mesenchymal stem cells can differentiate into both bone and cartilage, in cases in which, for example, an injury extends to bone as well as cartilage, these cells are able to regenerate bone at the site of the bone and cartilage at the site of the cartilage. By suspending bone marrow mesenchymal stem cells in a solution of a monovalent metal salt of alginic acid and injecting into a joint, the suspension can be used to treat cartilage disease. Thus, although the cells used in the present invention preferably consist of a high proportion of bone marrow mesenchymal stem cells, since it is difficult to isolate these cells completely, bone marrow mesenchymal stem cells are contained among the cells for regenerating cartilage tissue of the present invention preferably at 30% or more, more preferably at 50% or more, even more preferably at 70% or more and particularly preferably at 90% or more. One aspect of the composition of the present invention is a composition in which bone marrow mesenchymal stem cells and/or bone marrow mesenchymal stromal cells are used for regenerating cartilage or treating a cartilage disease.

Although the embedded cells may be heterologous cells or autologous cells, autologous cells are preferably harvested and used from the viewpoint of preventing rejection reactions in particular. The harvested cells are preferably used after proliferating by cell culturing. At this time, the cells may first be embedded in a solution of a monovalent metal salt of alginic acid and then cultured while in that state, or the cells may be embedded in a solution of a monovalent metal salt of alginic acid after culturing the cells in a culture medium.

The cells can be cultured according to an ordinary method, and the cells may be cultured while embedded in a solution of a monovalent metal salt of alginic acid or they may be cultured without embedding in a solution of a monovalent metal salt of alginic acid. A medium that enables the culturing of cells embedded in a solution of a monovalent metal salt of alginic acid as well as cells not embedded therein to be carried out efficiently is preferable for the culture medium, and the culture medium can be suitably selected by a person with ordinary skill in the art from known media.

Examples of media that can be used include DMEM medium (Virology, Vol. 8, 396 (1959)), MEM medium (Science, Vol. 122, 501 (1952)), RPMI1640 medium (The Journal of the American Medical Association, Vol. 199, 519 (1967)) and F12, and serum, amino acids, glucose or antibiotics and the like can be added as necessary. The pH is preferably about 6 to 8. Culturing is normally carried out at about 30 to 40° C. for 5 to 120 hours and preferably for 5 to 100 hours. In addition, the media can be replaced, aerated or stirred as necessary.

In one aspect of the present invention, the composition contains a solution of a monovalent metal salt of alginic acid mixed with cells for regenerating cartilage tissue, and particularly bone marrow mesenchymal stem cells or bone marrow mesenchymal stromal cells, and does not contain growth factor such as TGF-β. Furthermore cell differentiation does not necessarily have to be induced in vitro. In this case, if marrow fluid is harvested from the anterior margin of the ilium of a patient with a cartilage injury, for example, bone marrow mesenchymal stem cells are immediately removed from the bone marrow fluid and the number of cells obtained there from is a certain number of cells or more, the cells can be applied to the patient directly in the form of the composition of the present invention. Since there is no bother of having to culture and differentiate the harvested cells in vitro, the procedure is extremely advantageous for the surgeon, costs can be reduced, and the burden on the patient can be diminished.

In addition, bone marrow mesenchymal stem cells have superior practicality in terms of enabling allogenic cells to be applied without incident due to the low immunogenicity thereof.

On the other hand, a solution of a monovalent metal salt of alginic acid embedded with the cells described above can be used as a composition in which the embedded cells are cultured in vitro prior to applying a cartilage injury lesion in any state selected from the group consisting of a) a state in which the number of cells is $1 \times 10^6$ cells/mL or more, b) a state in which hyaline-like cartilage tissue is detected by Safranin-O staining or H-E staining, c) a state in which type II collagen is detected by anti-collagen II antibody or genetic analysis, d) a state in which aglycan is detected by anti-aglycan antibody or genetic analysis, and e) a state in which the extracellular matrix (collagen, hyaluronic acid, proteoglycan) is secreted. This state can be suitably selected according to the state of the injury lesion and the status of the patient.

Although there are no particular limitations on the amount of cells embedded, it may be, for example, $1.0 \times 10^6$ to $3.0 \times 10^7$ cells/ml, and preferably $2.0 \times 10^7$ to $3.0 \times 10^7$ cells/ml. Cartilage regeneration can be more effectively promoted by using this number of cells.

On the other hand, it is preferable to use a composition not containing cells to facilitate the surgical procedure as well as reduce the risk of infection by viruses and the like attributable to the body or the culturing process without placing an excessive burden on the body through such procedures as harvesting chondrocytes, periosteum or bone marrow. A preferable example of such a composition is a composition for regenerating cartilage having a viscosity of 400 to 20000 mPa·s and having fluidity for curing at an affected area by applying to a cartilage injury lesion, comprising a cell-free composition containing low endotoxin sodium alginate having a weight average molecular weight as determined by gel filtration chromatography of 500,000 or more. In addition, the composition for treating a cartilage disease of the present invention is a composition having for an active ingredient thereof a low endotoxin monovalent metal salt of alginic acid, and is based on the finding that the alginic acid itself has a therapeutic effect on cartilage disease. An example of a preferable therapeutic composition is a composition for treating a cartilage disease that is injected into a joint, comprising a cell-free composition containing as an active ingredient thereof low endotoxin sodium alginate having a weight average molecular weight as determined by gel filtration chromatography of 500,000 or more, and is able to demonstrate therapeutic effects that are superior to hyaluronic acid preparations used in the prior art.

7. Gelation of the Composition Surface

In the present invention, a composition containing a solution of a monovalent metal salt of alginic acid may be applied to a cartilage injury lesion, and a crosslinking agent may be applied to the surface of the composition. Gelling the surface of the composition to solidify the surface makes it possible to effectively prevent leakage of the composition from the cartilage injury lesion.

There are no particular limitations on the crosslinking agent provided it is able to solidify a surface of a solution of a monovalent metal salt of alginic acid by crosslinking that solution, and examples include divalent or more metal ion compounds such as $Ca^{2+}$, $Mg^{2+}$, $Ba^{2+}$ or $Sr^{2+}$, and crosslinking reagents having 2 to 4 amino groups in a molecule thereof.

Specific examples of divalent or more metal ion compounds include $CaCl_2$, $MgCl_2$, $CaSO_4$ and $BaCl_2$, while specific examples of crosslinking reagents having 2 to 4 amino groups in a molecule thereof include diaminoalkanes optionally having a lysyl group (—COCH($NH_2$)—($CH_2$)$_4$—$NH_2$) on a nitrogen atom, namely derivatives which form lysylamino groups as a result of a diaminoalkane and amino group thereof being substituted with a lysyl group. Although specific examples thereof include diaminoethane, diaminopropane and N-(lysyl)-diaminoethane, $CaCl_2$ solution is particularly preferable for reasons such as ease of acquisition and gel strength.

There are no particular limitations on the method used to add a divalent or more metal ion to the surface of the composition, and example of such a method consists of applying a solution of a divalent or more metal ion to the surface of the composition with a syringe or sprayer. The crosslinking agent may be applied to the surface of the composition of the present invention either after or simultaneous to the application of the composition of the present invention to a cartilage defect.

The amount of crosslinking agent applied is preferably suitably adjusted according to the size of the defect where the composition of the present invention is applied. The crosslinking agent gradually penetrates to the inside from the surface of the composition to which it is applied after which crosslinking progresses. The amount of the crosslinking agent applied is adjusted so as not to be in excess to prevent the crosslinking agent from having an excessively strong effect on the site where the composition of the present invention contacts a cartilage injury lesion. There are no particular limitations on the amount of divalent or more metal ion applied provided it is able to solidify the surface of the composition containing a monovalent metal salt of alginic acid. However, in the case of adding a 100 mM $CaCl_2$ solution, for example, the amount added is preferably about 0.3 to 0.6 ml in the case of a defect having a diameter of about 5 mm and a depth of about 2 mm, and the dosage may also be determined in proportion to the surface area of the affected part. For example, the amount added is preferably about 1 to 12 ml and more preferably about 2 to 10 ml in the case of a defect having a width (10 mm×20 mm) and depth of about 5 mm. The amount added can be suitably adjusted while viewing the status of the cartilage injury lesion. The crosslinking agent can be applied by, for example, continuously and slowly applying to the surface of the composition containing a monovalent metal salt of alginic acid for several to ten or more seconds.

In addition, by containing in the composition of the present invention a crosslinking agent by which gelation is promoted by environmental changes such as a time difference, temperature difference or contact with calcium ion within the body, a composition can be obtained that maintains a liquid state prior to administration and gels spontaneously following administration into the body. Examples of such crosslinking agents include calcium gluconate, $CaSO_4$ and calcium alginate.

Here, in the case calcium is contained in the crosslinking agent, a higher calcium concentration is known to result in rapid gelation and the formation of a harder gel. However, since calcium is cytotoxic, if the concentration thereof is excessively high, there is the risk of having a detrimental effect on the cartilage regenerative action of the composition for regenerating cartilage or treating a cartilage disease of the present invention. Therefore, in the case of using a $CaCl_2$ solution to solidify the surface of a composition containing a monovalent metal salt of alginic acid, for example, the calcium concentration is preferably 25 to 200 mM and more preferably 50 to 100 mM.

Here, alginate beads are produced by, for example, dropping a sodium alginate solution into a $CaCl_2$ solution followed by gelation. Alginate beads embedded with cells are known to be used for regenerating cartilage (see, for example, References 2 and 3). However, although it is necessary for alginate beads to be applied by pressing into a cartilage defect, since it necessary to produce beads that match the size of the defect, their use in an actual clinical setting is technically difficult. In addition, in the case of using a $CaCl_2$ solution as a crosslinking agent, since Ca ions on the surface of the beads contact the surface of the cartilage injury lesion, there is also the problem of cytotoxicity caused by the calcium. In contrast, since the composition of the present invention is in the form of a solution, it can be easily applied to a defect of any shape, the entire cartilage injury lesion is able to be covered with the composition, and adherence to the cartilage defect is satisfactory. Since the calcium concentration at the site where the composition contacts the surface of the cartilage injury lesion can be maintained at a low level, there are also few problems with respect to calcium cytotoxicity. Since the effect of the crosslinking agent on the surface of the cartilage injury lesion contacted by the composition of the present invention is small, the composition of the present invention is able to be easily contacted with cells and tissue at sites of cartilage injury in the body. Once about four weeks have elapsed since being applied to a cartilage injury lesion, the composition of the present invention fuses with tissue to a degree to which it is indistinguishable at the applied site, thus demonstrating high bioaffinity.

When applying the composition of the present invention to a cartilage injury lesion, if applied by first mixing with a crosslinking agent so as to gel the entire composition with the crosslinking agent, or by dressing a crosslinking agent to the surface of the composition, the composition of the present invention can be cured at the affected area and localized thereat in the state of being adhered to the cartilage injury lesion where applied. As a result, when cells and the like have been embedded, components such as the cells can be localized at the affected area. In addition, as a result of adhering the composition of the present invention to a cartilage injury lesion, the cartilage regeneration effects of the composition of the present invention, and particularly hyaline cartilage regeneration effects, can be demonstrated more potently.

8. Formulation and Application of a Composition for Regenerating Cartilage or Treating a Cartilage Disease Containing a Monovalent Metal Salt of Alginic Acid The composition for regenerating cartilage or treating a cartilage disease of the present invention is applied to a cartilage injury lesion of a human or non-human mammal such as a cow, monkey, bird, cat, mouse, rat, guinea pig, hamster, pig, dog, rabbit, sheep or horse, and is used to promote cartilage regeneration or treat cartilage disease by injecting into a joint.

The form of the composition for regenerating cartilage or treating a cartilage disease of the present invention is preferably a fluid liquid, namely a solution. In the present invention, the phrase "having fluidity" refers to the having of a property that causes the form thereof to change to an amorphous form, and does not require that the form constantly have the property of flowing in the manner of a liquid, for example. For example, the composition preferably has fluidity such that it is able to be sealed in a syringe and the like and injected to an affected area. The composition of the present invention in the form of a solution can be easily applied to a cartilage injury lesion or into a joint with a syringe, gel pipette or special-purpose syringe. In addition, it is compatible with any shape of cartilage injury lesion or defect, and is able to fill or contact the entire cartilage defect.

The composition for regenerating cartilage of the present invention demonstrates superior cartilage regenerative action at, for example, a cartilage defect of hyaline cartilage in the form of articular cartilage. In addition, the composition for treating a cartilage disease of the present invention demonstrates therapeutic effects on a cartilage disease such as osteoarthritis by having cartilage repair effects, effects that inhibit cartilage degenerative changes, cartilage protective effects, effects that inhibit inflammation of joint tissue and/or effects that suppress pain attributable to inflammation of joint tissue.

One aspect of the composition for regenerating cartilage of the present invention is a composition for regenerating hyaline cartilage. An object of a composition for regenerating hyaline cartilage is to regenerate cartilage having a high ratio of hyaline cartilage as compared with fibrous cartilage, and is intended to regenerate cartilage tissue rich in type II collagen and proteoglycan.

In addition, one aspect of the composition for treating a cartilage disease of the present invention is a composition for treating osteoarthritis. In the case a cartilage injury extends over a wide area of articular cartilage in the manner of osteoarthritis, or when desiring to treat a type of cartilage injury frequently observed in a comparatively early stage of osteoarthritis such that smoothness of the cartilage surface is disturbed and degenerative changes have begun even though well-defined cartilage defects have not yet occurred, the composition of the present invention is preferably applied by injecting into an articular cavity and allowing to disperse throughout the synovial fluid. Contact of a monovalent metal salt of alginic acid with a cartilage injury lesion promotes repair of the joint at the cartilage injury lesion, inhibits degenerative changes caused by inflammation and wear, and protects the cartilage. In addition, as a result of the active ingredient in the form of a monovalent metal salt of alginic acid being dispersed throughout the synovial fluid, inflammatory responses of surrounding tissue, including synovial tissue, are inhibited and effects that suppress pain are demonstrated. At the same time, the presence of a monovalent metal salt of alginic acid within synovial fluid fulfills the role of compensating for the function of synovial fluid by serving as a cushion and lubricant.

Another aspect of the composition for treating a cartilage disease of the present invention is a composition for treating frozen shoulder (periarthritis humeroscapularis). Frozen shoulder presents primarily with inflammation of the synovial membrane and articular capsule coupled with pain associated therewith, and cartilage wear and degeneration may not be observed. Since a monovalent metal salt of alginic acid demonstrates the effects of inhibiting inflammatory responses of surrounding tissue, including synovial tissue and suppressing pain, frozen should can be treated by administering the composition of the present invention into the shoulder articular cavity, subacromial bursa or biceps muscle tendon sheath.

Another aspect of the composition for treating a cartilage disease of the present invention is a composition for suppressing joint pain. Joint pain is frequently a problem in rheumatoid arthritis in addition to osteoarthritis, frozen shoulder and the like as previously described. A preferable aspect of the present invention is a composition for treating joint pain associated with rheumatoid arthritis, and is particularly preferably a composition for suppressing knee joint pain associated with chronic rheumatoid arthritis. Although the mechanism of occurrence of rheumatoid arthritis is not yet fully understood, synovial tissue and cartilage tissue are thought to be destroyed by inflammatory cytokines resulting from an autoimmune response. Since a monovalent metal salt of alginic acid demonstrates effects that inhibit inflammatory responses of surrounding tissue, including synovial tissue and suppress pain, the composition of the present invention is able to inhibit inflammatory responses and suppress pain associated therewith by administering into a joint suffering from rheumatoid arthritis. On the other hand, it is also necessary to suppress an autoimmune response in order to fundamentally treat rheumatoid arthritis, and whether or not a monovalent metal salt of alginic acid has immunosuppressive action at an area affected by rheumatoid arthritis has yet to be determined.

Another aspect of the composition for treating a cartilage disease of the present invention is a composition for alleviating, improving and/or curing various symptoms associated with a cartilage disease. In a cartilage disease, cartilage, cartilage tissue and/or joint tissue (such as synovial membrane, articular capsule or subchondral bone) are injured by mechanical irritation or inflammatory response, and compound symptoms occur such as degenerative changes in cartilage tissue, inflammation of the synovial membrane and other joint tissue and joint pain attributable to inflammation due to wear and mechanical irritation of articular cartilage along with inflammatory responses. Since the composition of the present invention contains as an active ingredient thereof a low endotoxin monovalent metal salt of alginic acid, it has the multiple effects of protecting cartilage from mechanical irritation, inhibiting degenerative changes in cartilage caused by wear and inflammation, repairing cartilage injury lesions, and suppressing inflammation of joint tissue and pain. As a result, the composition of the present invention is able to inhibit the progress of a cartilage disease, and alleviate, improve and/or cure symptoms. In addition, the composition for treating a cartilage disease of the present invention has the effect of improving joint function through alleviation, improvement and/or curing symptoms thereof. Improvement of joint function refers to improving joint range of movement, improving movement carried out during the course of daily life and the like.

When applying the composition for regenerating cartilage of the present invention in the form of filling into a cartilage defect, since it is difficult to apply the composition with a syringe if the viscosity is high, a pressurized or motorized syringe may be used. The composition may also be applied to a cartilage defect with, for example, a spatula or rod without having to use a syringe and the like. In the case of injecting with a syringe, a 16 to 18G needle, for example, is used preferably. In the case of applying the composition for treating a cartilage disease of the present invention by injecting into a joint, an 18 to 27G needle is used preferably.

The applied amount of the composition for regenerating cartilage of the present invention is determined according to the size of the hole(s) formed in the cartilage injury lesion or cartilage defect where it is applied, and although there are no particular limitations thereon, in the case of injecting directly into a cartilage defect, for example, the applied amount is preferably 0.05 to 10 ml and more preferably 0.1 to 2 ml. Application to a cartilage injury lesion preferably consists of injecting so as to adequately fill the void volume of the affected area. In the case of applying the composition for treating a cartilage disease of the present invention by injecting into a joint, the dose is suitably determined according to amount of synovial fluid of the joint into which the composition is to be injected, and although there are no particular limitations thereon, in the case of administering to a human knee joint or shoulder joint, the dose is normally 1 to 5 mL and more preferably 2 to 3 mL. In addition, the administration method may consist of, for example, administering in five consecutive administrations at one week intervals, followed by continuous administrations every 2 to 4 weeks. Although there are no particular limitations on the dose, the dose can be suitably adjusted according to the symptoms and effects. For example, an administration method may be adopted in which administration is suitably continued once every two weeks or once every month. Since alginic acid is inherently not present in the body, animals do not have an enzyme capable of specifically breaking down alginic acid. Although alginic acid is normally gradually decomposed by hydrolysis in an animal body, since its decomposition in the body is slow in comparison with polymers such as hyaluronic acid, it can be expected to sustain long-term effects in the case of being administered into a joint.

The composition for regenerating cartilage or treating a cartilage disease of the present invention contains as an active ingredient thereof a low endotoxin monovalent metal salt of alginic acid. The inventors of the present invention found for the first time that alginic acid itself demonstrates regenerative and therapeutic effects on cartilage tissue and joint tissue in the case of administering alginic acid into a joint of the body. The containing of alginic acid as an active ingredient means that alginic acid is contained in an amount that enables it to demonstrate regenerative and therapeutic effects on cartilage tissue and joint tissue when applied to an affected area, and that amount is preferably at least 0.1% w/v or more of the entire composition, more preferably 0.5% w/v or more, and particularly preferably 1 to 3% w/v.

The composition for regenerating cartilage or treating a cartilage disease of the present invention can also contain components ordinarily used in pharmaceuticals, such as other pharmaceutically active ingredients and commonly used stabilizers, emulsifiers, osmotic pressure adjusters, buffers, isotonic agents, preservatives, pain relievers or colorants as necessary.

Furthermore, in one aspect of the present invention, the composition of the present invention does not contain a component demonstrating pharmacological action on cartilage or joint tissue other than a low endotoxin monovalent metal salt of alginic acid. A composition containing as an active ingredient thereof only a low endotoxin monovalent metal salt of alginic acid is also able to demonstrate adequate effects for regenerating cartilage or treating a cartilage disease.

In addition, the composition for regenerating cartilage or treating a cartilage disease of the present invention can also contain a factor that promotes cell growth, examples of which include BMP, FGF, VEGF, HGF, TGF-13, IGF-1, PDGF, CDMP, CSF, EPO, IL and IF. These factors may be produced by a recombination technique, or may be purified from a protein composition.

Furthermore, in one aspect of the present invention, the composition of the present invention does not contain these growth factors. Even in the case of not containing growth factor, however, cartilage regeneration is adequately satisfactory, and safety is higher than in the case of aggressively promoting cell growth.

9. Treatment Method

Moreover, the present invention provides a method of treating a cartilage injury lesion and a method of treating a cartilage disease that uses the composition of regenerating cartilage or treating a cartilage disease of the present invention as described above.

"Treatment of a cartilage injury lesion" or "treatment of a cartilage disease" is as previously explained in section 1 entitled "Introduction".

There are no particular limitations on the method for applying the composition for regenerating cartilage of the present invention to a cartilage injury lesion, and the composition may be applied by, for example, injecting directly into a cartilage defect with a syringe, gel pipette or special-purpose filler and the like either arthroscopically or endoscopically. Alternatively, the composition may be injected directly into a cartilage defect with a syringe, gel pipette or special-purpose filler and the like after exposing the affected area by a known surgical technique such as arthrotomy using a medial parapatellar approach.

In addition, concomitant drugs including antibiotics such as streptomycin, penicillin, tobramycin, amikacin, gentamicin, neomycin or amphotericin B or anti-inflammatory drugs such as aspirin, non-steroid anti-inflammatory drugs (NSAIDs) or acetaminophen may also be administered before, simultaneous to or after application of the composition of the present invention to a cartilage injury lesion. These drugs may also be used by mixing into the composition of the present invention.

In addition, one or more holes may be formed in a cartilage injury lesion and the composition of the present invention may be injected into the formed hole(s). Moreover, the composition may also be used in the same manner by forming one or more holes in a cartilage defect.

For example, in the case of a technique involving exposure of an affected area by a surgical procedure, a plurality of defects (full-thickness defects) having a comparatively small diameter of, for example, about 1.5 mm and extending to the subchondral bone may be formed using a power drill or steel wire and the like in a cartilage defect where residual cartilage is present prior injecting the composition of the present invention, followed by injection of the composition therein. As a result of forming full-thickness defects, bleeding occurs from the bone marrow enabling cartilage precursor cells in the bone marrow to migrate to the cartilage defect. Cartilage regeneration is promoted by the effects of the migrated cartilage precursor cells and the composition of the present invention, thereby making it possible to improve the function of the entire cartilage.

Alternatively, partial defects having a comparative small diameter of, for example, about 1.5 mm but not extending to the subchondral bone may be formed in a cartilage defect where residual cartilage is present followed by application of the composition of the present invention thereto. In the case of forming partial defects, there is no bleeding of bone marrow into the defect and no infiltration of cartilage precursor cells in the bone marrow. In this case as well, the effects of the composition of the present invention are demonstrated by applying the composition to small-diameter holes, regeneration of cartilage is satisfactory, and the function of the entire cartilage can be improved. These techniques are effective in cases in which residual cartilage is present in the cartilage defect.

10. Kit for Regenerating Cartilage of Treating a Cartilage Disease

Moreover, the present invention provides a kit for regenerating cartilage or treating a cartilage disease. This kit includes the composition for regenerating cartilage or treating a cartilage disease of the present invention as described above, a crosslinking agent, syringe, gel pipette, special-purpose filler, instructions and the like. A preferable specific example of a kit is that in which a monovalent metal salt of alginic acid is sealed in one compartment of a syringe composed of two integrally formed compartments divided by a partition, and a solution in the form of physiological saline or a solution containing a crosslinking agent in the form of calcium ion such as CaCl$_2$ is sealed in the other compartment, and is composed such that the partition between the compartments can be penetrated easily at the time of use to enable the contents of both compartments to be used by mixing and dissolving at the time of use. Another example of a kit is that a monovalent metal salt solution of alginic acid is sealed in a pre-filled syringe allowing it to be administered directly at the time of use without requiring a preparation procedure. Another example is a kit in which an alginic acid solution and a crosslinking agent are sealed in separate syringes and packaged together in a single pack. The "composition for regenerating cartilage or treating a cartilage disease", "crosslinking agent" and "syringe" are as previously explained. Furthermore, cells may be embedded in the composition containing a monovalent metal salt of alginic acid as previously described. Moreover, the kit can also contain concomitant drugs including antibiotics such as streptomycin, penicillin, tobramycin, amikacin, gentamicin, neomycin or amphotericin B or anti-inflammatory drugs such as aspirin, non-steroid anti-inflammatory drugs (NSAIDs) or acetaminophen.

The use of this kit enables cartilage regenerative therapy and cartilage disease therapy to be carried out smoothly.

Furthermore, all publications cited in the present specification, such as prior art documents, laid-open patent applications, patent publications and other patent documents, are incorporated in their entirety in the present specification as references. In addition, the present specification incorporates the contents of the specifications of Japanese Patent Application No. 2007-41520 and Japanese Patent Application No. 2007-277005, which serve as the basis for claiming of priority of the present application.

Although the following provides a detailed explanation of the present invention through examples thereof, the present invention is not limited to these examples.

EXAMPLE 1

Preparation of Sodium Alginate Solution

In the present example, two types of sodium alginate were used consisting of purified sodium alginate (Kimica Corp., Mochida International Ltd., Sea Matrix (sterilized), Serial No. B5Y01) and non-purified, food grade sodium alginate (also referred to as commercial grade sodium alginate, Wako Pure Chemical Industries, Ltd., Sodium Alginate 500, 199-09961). The purified sodium alginate was sterilized and freeze-dried. The food grade sodium alginate was sterilized by filtering with a filter having a pore diameter of 0.22 μm.

When endotoxin levels were measured using a commercially available LAL assay kit (Limulus Color KY Test Wako, Japan), the endotoxin level of the purified sodium alginate was 5.76 EU (endotoxin units)/g and that of the food grade sodium alginate was 75950 EU/g, thus indicating that the endotoxin level of the purified sodium alginate was far lower than that of the food grade sodium alginate. Namely, the purified sodium alginate had been subjected to endotoxin reduction treatment. In addition, the heavy metal content of the purified sodium alginate was 20 ppm or less, the lead sulfate content was 0.98% or less, and the arsenic content was 2 ppm or less.

In addition, 1% w/v and 2% w/v concentrations of sodium alginate solutions were prepared from each sodium alginate using filtration sterilized Milli-Q water. The viscosity of each concentration of sodium alginate solution at 20° C. was then measured using a rotational viscometer (cone-and-plate type, TVE-20LT, Toki Sangyo Co., Ltd., Japan). The rotating speeds were 1 rpm when measuring the 1% sodium alginate solutions and 0.5 rpm when measuring the 2% sodium alginate solutions, and the measuring ranges consisted of M when measuring the 1% sodium alginate solutions and 5M when measuring the 2% sodium alginate solutions. The results are shown in Table 1.

TABLE 1

| Alginic acid | Concentration (%) | Viscosity (mPa·s) | | | | |
|---|---|---|---|---|---|---|
| | | 1st measurement | 2nd measurement | 3rd measurement | Average | Standard deviation |
| Food grade | 1 | 533.5 | 537.0 | 531.5 | 534.0 | 2.27 |
| Food grade | 2 | 5377.0 | 5336.0 | 5325.0 | 5346.0 | 22.38 |
| Purified | 1 | 435.4 | 434.1 | 429.3 | 432.9 | 2.62 |
| Purified | 2 | 5359.0 | 5496.0 | 5488.0 | 5447.7 | 62.78 |

As shown in Table 1, the viscosity of the purified sodium alginate was about 430 mPa·s for the 1% w/v solution and about 5400 mPa·s for the 2% w/v solution. The viscosity of the food grade sodium alginate was about 530 mPa·s for the 1% w/v solution and about 5300 mPa·s for the 2% w/v solution. On the basis of the results for both groups, the viscosity of each solution of the purified sodium alginate and food grade sodium alginate used in the present example was found to be about 400 to 600 mPa·s at a concentration of 1% w/v and about 5000 to 6000 mPa·s at a concentration of 2% w/v.

The physical properties were confirmed for purified and food grade sodium alginate solutions having concentrations of 1, 2 or 3% w/v. When several drops of each concentration of the sodium alginate solutions were applied from below to an inverted plastic dish, although the majority of the 1% w/v sodium alginate solutions (viscosity: approx. 400 to 600 mPa·s) dropped from the dish in a few seconds due to gravity, some of the sodium alginate remained adhered to the bottom of the dish. On the basis of this result, if a composition containing a monovalent metal salt of alginic acid has a viscosity of about 400 to 600 mPa·s or more, the effects of the present invention were suggested to be obtained since the composition has adhesiveness and the property of remaining at the affected area. In contrast, the sodium alginate solutions having a concentration of 2% w/v (viscosity: approx. 5000 to 6000 mPa·s) did not run down from the dish and remained adhered to the dish for at least about one minute. Even after some of the solutions had dropped from the dish, a large amount of the sodium alginate remained adhered thereto. Sodium alginate solutions having a concentration of 3% w/v remained adhered to the dish even longer than the 2% w/v solutions.

On the other hand, with respect to the handling ease of the composition, the 3% w/v sodium alginate solutions required some time to dissolve in Milli-Q water and although were somewhat difficult to fill into the pipette and syringe, the pipette and syringe were able to be operated. The 1% and 2% w/v sodium alginate solutions were easy to handle.

Here, since the sodium alginate used here was thought to be similar to the sodium alginate solution having a concentration of 1% and viscosity of 570 mPa·s used in Experiment 10, the viscosity of the 3% w/v sodium alginate solutions were determined to be about 20000 mPa·s. Thus, the viscosity of the composition containing a monovalent metal salt of alginic acid was suggested to preferably be about 20000 mPa·s or less with respect to ease of handling when using a pipette or syringe.

On the basis of the above results, when the viscosity of the sodium alginate solutions was made to be 5000 to 6000 mPa·s, preparation and manipulation were the easiest and this viscosity was indicated as being suitable for use as a composition for regenerating cartilage or treating a cartilage disease. In the clinical setting, there are many cases in which the cartilage injury lesion is facing downward or to the side, such as in the case of arthroscopically manipulating a cartilage injury lesion on the surface of a femoral joint, for example. As a result of adjusting the viscosity of the composition of the present invention, the composition was indicated as being able to be used over a wide range of various forms of cartilage injuries even with respect to cartilage injuries involving a difficult procedure in this manner. Furthermore, the concentration may be adjusted to about 2% w/v using Milli-Q water in order to obtain a viscosity of 5000 to 6000 mPa·s in the case of the purified sodium alginate solution used in the present example.

EXAMPLE 2

Production of Transplant Cells

Bone marrow mesenchymal stromal cells (BMSC) were isolated and cultured to obtain transplant cells. BMSC include erythropoietic cells and the like in addition to bone marrow mesenchymal stem cells. 10 mL of bone marrow were harvested from the tibia of four-month-old Japanese white rabbits followed by washing twice with Ca—Mg-free PBS (Gibco BRL Lab.) and suspending in DMEM-High Glucose (DMED-HG, Sigma Chemical, St. Louis, Mo.). Blood clots were removed with a cell strainer having a pore diameter of 70 μm (Falcon Co., Ltd.). The cells were then incubated while humidifying at 37° C. and 5% $CO_2$ in a 100 mm culture dish containing a culture medium consisting of DMEM-HG, 10% fetal bovine serum (FBS, Gibco, Life Technology, Grand Island, N.Y.) and 1% antibiotics (Penicillin-Streptomycin-Fungizone 100× concentrated, Cambrex Biosciences, Walkersville, Md.). The culture medium was replaced every three days and non-adherent cells were removed. After monolayer culturing the adherent cells for 10 to 14 days, the cells were removed with trypsin-EDTA (10 mM, Sigma, UK) and counted followed by subculturing every three days.

EXAMPLE 3

Production of Alginate Beads

The cells obtained in Example 2 were suspended at $2.5 \times 10^7$ cells/ml in a sodium alginate solution adjusted to a concentration of 2% w/v with filtration-sterilized Milli-Q water. The suspension was gelled by dropping into $CaCl_2$ solution with a pipette, and after washing for two times the microcapsules that formed 10 minutes later with Ca—Mg-free PBS, the microcapsules were washed once with DMED-HG. The resulting beads contained $1 \times 10^6$ cells per 40 μl per bead.

The cells were harvested from the alginate beads by washing three times with PBS and incubating at 37° and 5% $CO_2$ in 50 mM EDTA (Gibco BRL Laboratories) followed by centrifuging for 5 minutes at 1500 g 10 minutes later to harvest the cells.

EXAMPLE 4

Calcium Toxicity on Cells in Alginate Beads

Method

The survival rates of cells encapsulated in alginic acid by dropping in $CaCl_2$ solution were measured using the Cell Counting Kit 8 (CCK-8, Dojindo Laboratories, Tokyo, Japan). The cells obtained in Example 2 were suspended at $2.5 \times 10^7$ cells/ml in a sodium alginate solution adjusted to a concentration of 2% w/v and dropped in 50, 100, 200 and 400 mM concentrations of $CaCl_2$ solution according to the procedure of Example 3 and immersed for 15 minutes to obtain beads containing $1 \times 10^6$ cells per 40 μl per bead. After washing the alginate beads twice with PBS, the cells in the beads were harvested using the method described in Example 3 and then suspended in DMED-HG. The cells of each group were seeded in a 96-well plate and incubated for 1 hour followed by the addition of 20 μl of CCK-8 solution to each well and incubating for an additional 4 hours. The cell survival rates were obtained by measuring absorbance at 450 nm using a microplate reader (Bio-Rad Japan Life Science Research, Tokyo, Japan).

Results

The survival rates of the cells at each concentration of $CaCl_2$ solution are shown in FIG. 1.

The cell survival rates in the alginate beads decreased calcium concentration-dependently, and decreased significantly starting at a concentration of 200 mM. Thus, $CaCl_2$ was demonstrated to have cytotoxicity. In addition, it was found to be appropriate to make the concentration of calcium chloride that contacts the sodium alginate to be about 100 mM to minimize the effects on the cells and allow the sodium alginate to gel as quickly and as firmly as possible.

EXAMPLE 5

Comparison of Survival Rates of Cells in Alginate Beads

Method

The survival rates of cells in alginate beads were compared for purified sodium alginate subjected to endotoxin reduction treatment and food grade sodium alginate not subjected to endotoxin reduction treatment. Each of the alginate beads were produced by suspending the cells obtained in Example 2 in 2% w/v sodium alginate solution according to the procedure of Example 3 followed by dropping in 100 mM $CaCl_2$ solution. Each bead was made to contain $1 \times 10^6$ cells per 40 μl per bead. The two types of alginic acid capsules were cultured for 0, 1, 2, 3, 7 or 14 days in DMED-HG containing 10% FBS and 1% antibiotic. The cells were harvested from each capsule according to the method described in Example 3, and the numbers of viable cells were counted using the CCK-8 kit.

Results

Figure 2:
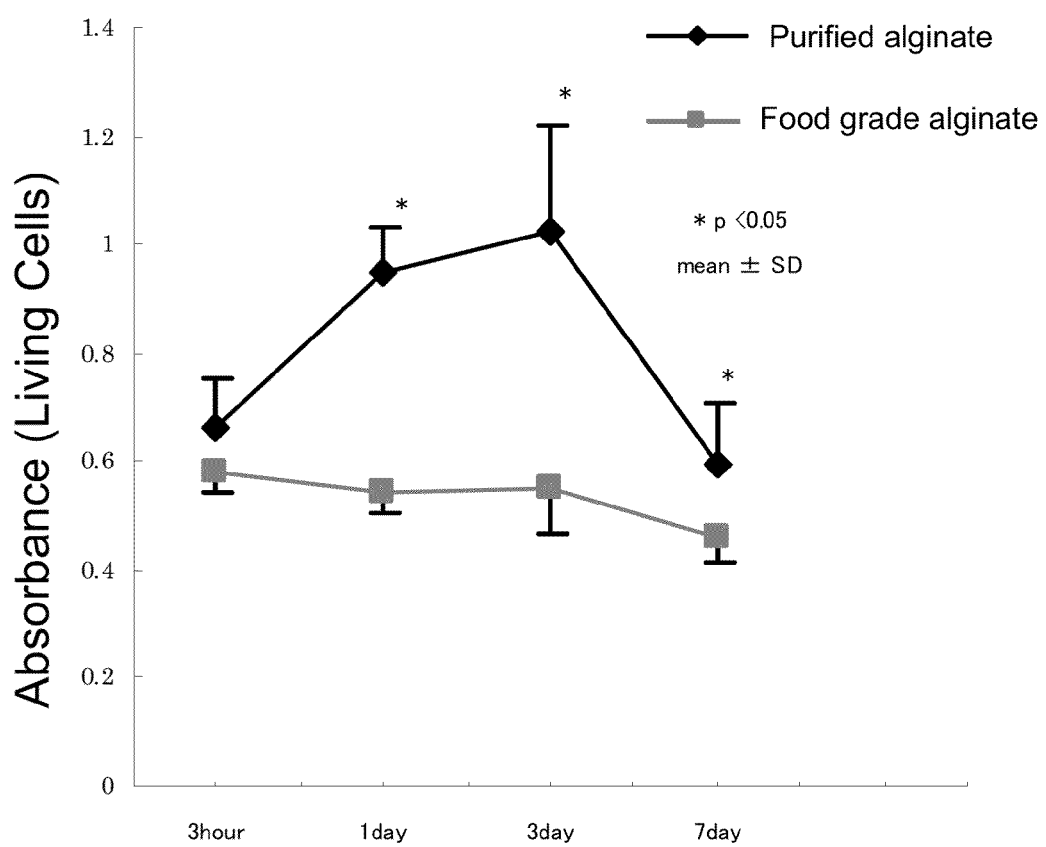
FIG. 2 is a graph showing the comparative effects of purified and food grade alginate beads on the survival rates of cells in the beads (Example 5).

The results are shown in FIG. 2. The number of remaining viable cells was significantly higher when using the purified sodium alginate solution subjected to endotoxin reduction treatment as compared with the use of food grade sodium alginate solution not subjected to endotoxin reduction treatment on days 1, 3 and 7. Sodium alginate solution subjected to endotoxin reduction treatment was confirmed to offer the advantage of, for example, having less toxicity on the cells early in the procedure (within 7 days) in particular as compared with not undergoing endotoxin reduction treatment.

EXAMPLE 6

Culturing in Alginate Beads in Vitro

Method
(Culturing)

Beads containing $1 \times 10^6$ cells per 40 µl per bead similar to those in Example 5 were produced according to Example 3 for purified sodium alginate and food grade sodium alginate, respectively. Individual beads were placed in each well of 24-well culture dishes and cultured in 1 ml of the standard culture medium described below. Namely, the standard culture medium used consisted of DMEM-HG containing 100 µg/ml of sodium pyruvate (ICN Biochemicals, Aurora, Ohio), 40 µg/ml of proline (ICN Biochemicals, Aurora, Ohio), 50 µg/ml of ascorbic acid 2-phosphate (Wako, Osaka, Japan), $1 \times 10^{-7}$ M dexamethasone (ICN Biochemicals, Aurora, Ohio), 1% ITS Plus Mix (Sigma-Aldrich, St. Louis, Mo.), 1% antibiotics and 10 ng/ml of recombinant human transforming growth factor β3 (R&D System, Minneapolis, Minn.) dissolved in 4 mM HCl containing 1 mg/ml of bovine serum albumin. The culture dishes were incubated at 37° C. and the medium was replaced every three days.

(RNA Real-Time RT-PCR Analysis)

After culturing for 14 days, total RNA was removed from homogenized cells and gene expression of type I, II and X collagen, aggrecan and Sox 9 was analyzed. All the experiments were performed by conventional methods.

Namely, RNA yield was determined by measuring absorbances at 260 and 280 nm. Next, cDNA was synthesized from 0.05 µg of RNA using the ImProm-II™ Reverse Transcription System (Promega, Madison, Wis.) in accordance with the manual. At this time, the binding product of the total RNA and a random primer was denatured for 5 minutes at 70° C. followed immediately by chilling for 5 minutes in ice water and carrying out reverse transcription for 60 minutes at 42° C. using ImProm-II™ reverse transcriptase. Next, the resulting cDNA was diluted with PCR-grade water (Roche Diagnostics, Indianapolis, Ind.) to adjust the concentration to less than 40 ng/µl. PCR was then carried out at a reaction volume of 20 µl and monitored using the DNA Engine Opticon™ 2 continuous fluorescence detection system (Bio-Rad Laboratories, Hercules, Calif.). Signals were detected with the SYBR Green qPCR Kit (Finzyme, Espoo, Finland) using gene-specific primers designed by DNASIS (Hitachi Software Engineering, Tokyo, Japan).

More specifically, the primers used are as indicated below.

```
Rabbit Type I Collagen:
                                        (SEQ ID NO: 1)
(5'-3') TAAGAGCTCCAAGGCCAAGA
and
                                        (SEQ ID NO: 2)
(3'-5') TGTACCTACTCCTTTGACCG Rabbit Type II Collagen:
                                        (SEQ ID NO: 3)
(5'-3') AGAGACCTGAACTGGGCAGA
and
                                        (SEQ ID NO: 4)
(3'-5') ACCACGATATGAGGCACAGTTT Rabbit Type X Collagen:
                                        (SEQ ID NO: 5)
(5'-3') GCCAGGACCTCCAGGACTAT
and
                                        (SEQ ID NO: 6)
(3'-5') CTTTGGACCTGTTGTCCCT Rabbit Aggrecan:
                                        (SEQ ID NO: 7)
(5'-3') GAGGTCGTGGTGAAAGGTGT
and
                                        (SEQ ID NO: 8)
(3'-5') TGACAGTCCATGGGGTAGGT Rabbit Sox 9:
                                        (SEQ ID NO: 9)
(5'-3') AAGGGCTACGACTGGACGCT
and
                                        (SEQ ID NO: 10)
(3'-5') GTGCAGTTCGCCGGGT
```

Following an initial denaturation step for 10 minutes at 95° C., the cDNA products were amplified by 40 cycles of PCR. Each cycle consisted of a denaturation step for 10 seconds at 94° C., an annealing step for 20 seconds at 58° C. and an elongation step for 30 seconds at 72° C. The data was analyzed using Opticon Monitor™ software (Bio-Rad Laboratories, Hercules, Calif.). The value obtained for each sample when fluorescence intensity reached 0.03 was determined to be the Ct (cycle threshold) value. This value was selected by confirming that all curves were in the exponential amplification phase within this range. The relative expression level of each gene was calculated using the modified comparative Ct method from the Ct values of each target gene and the reference gene (GAPDH).

(Staining)

The beads were washed with PBS after 21 and 28 days of culturing, and after fixing for 24 hours with 10% phosphate-buffered paraformaldehyde, the beads were embedded in paraffin. The beads were cut into 5 µm sections from the center of the beads followed by carrying out H-E staining and Safranin-O staining in accordance with ordinary methods. In addition, formation of types I, II and X collagen was confirmed with anti-type I, anti-type II (Fuji Pharm. Lab., Toyama, Japan) and anti-type X (Sigma, St. Louis, Mo.) anti-collagen antibodies.

Results

Figure 3:
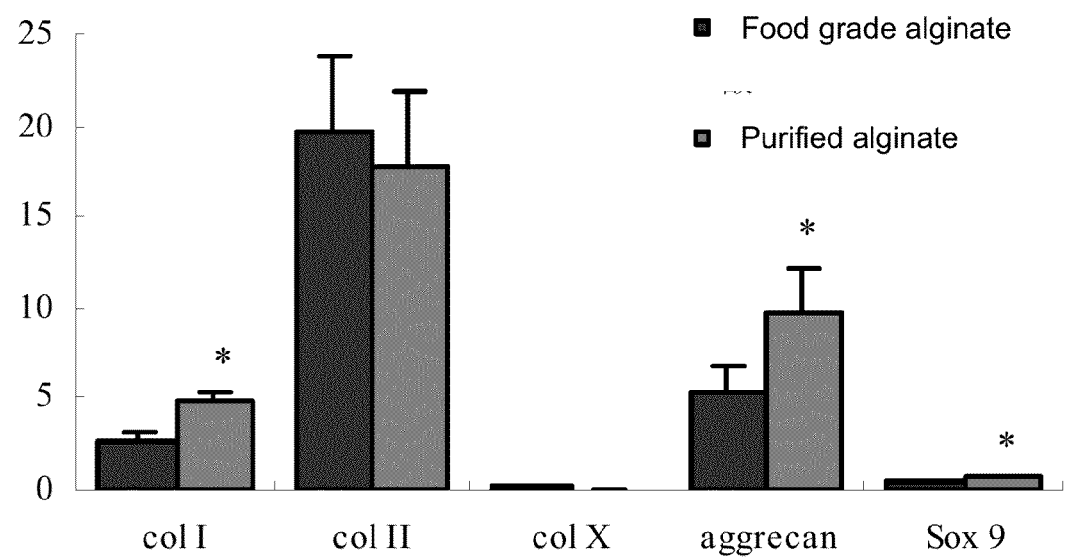
FIG. 3 is a graph showing the results of RT-PCR analyses during in vitro culturing of Example 6.

The results of RNA real-time RT-PCR analysis are shown in FIG. 3. In addition, the results of staining are shown in FIG. 4. FIG. 4A and FIG. 4B show the results when using purified sodium alginate, while FIG. 4C and FIG. 4D show the results when using food grade sodium alginate. In addition, FIG. 4A and FIG. 4C show the results for 21 days of culturing, while FIG. 4B and FIG. 4D show the results for 28 days of culturing. In addition, FIG. 4A to FIG. 4D respectively show, from left to right, the results for staining with H-E stain, Safranin-O stain, and anti-type I, anti-type II and anti-type X anti-collagen antibodies.

With reference to the results of RT-PCR (FIG. 3), increases were observed in type II collagen, aggrecan and Sox 9, which indicate differentiation of cells into cartilage, when using either purified sodium alginate or food grade sodium alginate.

A comparison of the two types revealed that culturing with the purified sodium alginate yielded significantly higher levels of aggrecan and Sox 9.

In addition, with reference to the staining results (FIG. 4), an extracellular matrix was produced that was stained with Safranin-O and type II collagen immunostaining, which indicates cartilage differentiation, for both types of alginate beads, and cartilage differentiation was observed.

EXAMPLE 7

Rabbit Cartilage Repair Model

Method
(Procedure)

Forty female Japanese white rabbits (body weights: 2.6 to 2.9 kg) were anesthetized with isoflurane in $O_2$ gas and intravenous injection of pentobarbital (0.05 mg/kg) followed by intramuscular injection of antibiotic (Penicillin G, Meiji-Seika, Japan) and shaving of the legs. A 2 cm anteromedial incision was made in the skin and the trochlear groove was accessed using a medial parapatellar approach. Osteochondral defects (diameter: 5 mm, depth: 2 mm) were created in the femoral trochlea using a power drill (Rexon, Japan). The knees were then irrigated with physiological saline, the absence of bleeding into the defects was confirmed and the defects were allowed to dry.

In the present example, the experiment was conducted by dividing the animals into five groups.
A) Control Group (empty)
B) Food grade alginate group (no cells)
C) Food grade alginate+cells ($2.5 \times 10^7$/mL) group
D) Purified alginate group (no cells)
E) Purified alginate+cells ($2.5 \times 10^7$/mL) group The defects were left untreated in the control group A). In addition, 2% w/v food grade sodium alginate solution was applied to the defects in the food grade alginate group B) (no cells). 2% w/v purified sodium alginate solution was applied to the defects in the purified alginate group D) (no cells). Moreover, the cells obtained in Example 2 were suspended in 2% w/v food grade sodium alginate solution or 2% w/v purified sodium alginate solution and applied to the articular cartilage defects in the food grade alginate+cells group C) and the purified alginate+cells group E), respectively. Rabbit autologous cells prepared according to the method described in Example 2 were used for the cells at this time.

The reason for making the concentration of the sodium alginate solutions 2% w/v is that the viscosity can be adjusted to a level of 5000 to 6000 mPa·s suitable for the procedure based on the results of Example 1.

The rabbits were immobilized with the defects facing upward, and the composition of the present invention was applied to the defects using a gel pipette.

Since the viscosity of the sodium alginate solution was suitable in groups B) through E), the sodium alginate solutions did not flow out of the defects despite conditions facilitating flow due to synovial fluid. Subsequently, approximately 0.5 ml of 100 mM $CaCl_2$ solution was slowly and continuously applied over the course of 10 seconds to the surface of the graft using a 27G syringe. The surface layer of the graft gelled immediately and the cells did not leave the affected area. The $CaCl_2$ solution was washed with physiological saline. Further immobilization was not required and the affected area was sutured following the procedure. The rabbits were able to move freely.

The subject rabbits were sacrificed by intravenous injection of an excessive dose of pentobarbital at 4 weeks or 12 weeks after the procedure. The distal ends of the femurs were excised with a power saw. FIG. 5 shows photographs taken at the time of the procedure.

(Overall Observations)

The overall appearance was observed macroscopically and scored. Overall appearance was scored according to the criteria of FIG. 6 with reference to the method of Gabriele, G. et al. (Biomaterial, 21 (2000), 2561-2574).

(Staining)

Subsequently, the specimens were fixed with paraformaldehyde, decalcified and embedded in paraffin. Sections located 5 μm from the center of the defect were stained with Safranin-O, H-E stain and immunostained with anti-type I collagen and anti-type II collagen. The scoring system described in FIG. 7 was used to evaluate the newly formed cartilaginous tissue and the tissue was evaluated microscopically. Independent blinded observers performed the scoring.

(Measurement of Mechanical Strength)

The mechanical strength of the affected area was measured using an indentation test. The specimens were firmly clamped with the femuropatellar joint facing upward, and the test was carried out at room temperature. The indentator was automatically moved toward the center of the regenerated cartilage and the displacement (mm) was recorded relative to the load (N). The thickness of the regenerated tissue was measured from histological sections. Young's modulus was then obtained from the linear region of the load-displacement curves.

Results

The results of staining are shown in FIG. 8 to FIG. 11.

As a result of H-E staining, Safranin-O staining and anti-type II collagen immunostaining, the most prominent formation of hyaline cartilage and type II collagen in comparison with the other groups was confirmed in the purified alginate+cells group E) (FIG. 11) at an early stage 4 weeks after the procedure. Roughly 80% of the cartilage was observed to be regenerated at 12 weeks after the procedure. The formation of subchondral bone was extremely favorable based on the results of H-E staining Safranin-O staining revealed the formation of proteoglycan, and the formation of an extracellular matrix was also able to be confirmed. On the other hand, there was hardly any formation of fibrous cartilage observed based on the results of H-E staining and anti-type I collagen immunostaining.

The purified alginate (no cells) group D) (FIG. 10) demonstrated favorable formation of hyaline cartilage, type II collagen and subchondral bone as compared with the food grade alginate+cells group C) (FIG. 9). In group D), in which cells were not embedded, cartilage regeneration was surprisingly found to have been obtained by hyaline chondrocytes. In addition, it also unexpectedly found that group D) in which cells were not embedded demonstrated a superior ability to regenerate cartilage injury as compared with group C) in which cells were embedded.

On the other hand, there was hardly any neogenesis of cartilage and type II collagen observed in control group A) (FIG. 8) in which the defects were left untreated.

The evaluation results obtained by macroscopically scoring the overall appearance (Macro) and the evaluation results obtained by scoring observations based on the staining described above (Histological) are shown in FIG. 12.

The total scores obtained by combining the Macro and Histological scores in week 12 consisted of 22.71 for the purified alginate+cells group E), 19.57 for the purified alginate (no cells) group D), 14.75 for the food grade alginate+cells group C), 10.25 for the food grade alginate (no cells) group B), and 8.43 for the control group A) (empty). Thus, the purified alginate+cells group E) demonstrated the highest score followed by the purified alginate (no cells) group D) and the food grade alginate+cells group C) in that order. It was completely unexpected that group D) in which cells were not embedded yielded a higher total score, and thereby demonstrating superior ability to regenerate cartilage in cartilage injuries, as compared with group C) in which cells were embedded.

The scoring results for both macroscopic evaluation of overall appearance (Macro total) and evaluation by staining (Histological total) were the highest in the purified alginate+cells group E) in the same manner as described above, and the next highest score was observed in the purified alginate (no cells) group D).

In looking at the Macro evaluation parameters, groups D) and E), in which purified alginate was used, were superior for all the parameters of edge integration (new tissue relative to native cartilage), smoothness of cartilage surface, cartilage surface, degree of filling, and color of cartilage, opacity or translucency of the neocartilage as compared with groups B) and C) in which food grade alginate was used.

In looking at the Histological evaluation parameters, groups D) and E), in which purified alginate was used, demonstrated higher scores than groups B) and C), in which food grade alginate was used, for the parameters of nature of predominant tissue, surface regularity, structural integrity and homogeneity, thickness, bonding to adjacent cartilage, degenerative changes in adjacent cartilage and inflammatory response.

On the basis of these findings, the composition of the present invention as represented by groups D) and E) demonstrated extremely favorable formation of chondrocytes and cartilage tissue in a cartilage injury, including the formation of hyaline cartilage, type II collagen and subchondral bone. There was hardly any formation of fibrous cartilage observed.

Bonding of the regenerated tissue to host tissue was also favorable, there was little degeneration or inflammation in adjacent cartilage, and bioaffinity was determined to be high.

Thus, the composition of the present invention was confirmed to effectively promote cartilage regeneration in cartilage injury lesion.

Figure 13:
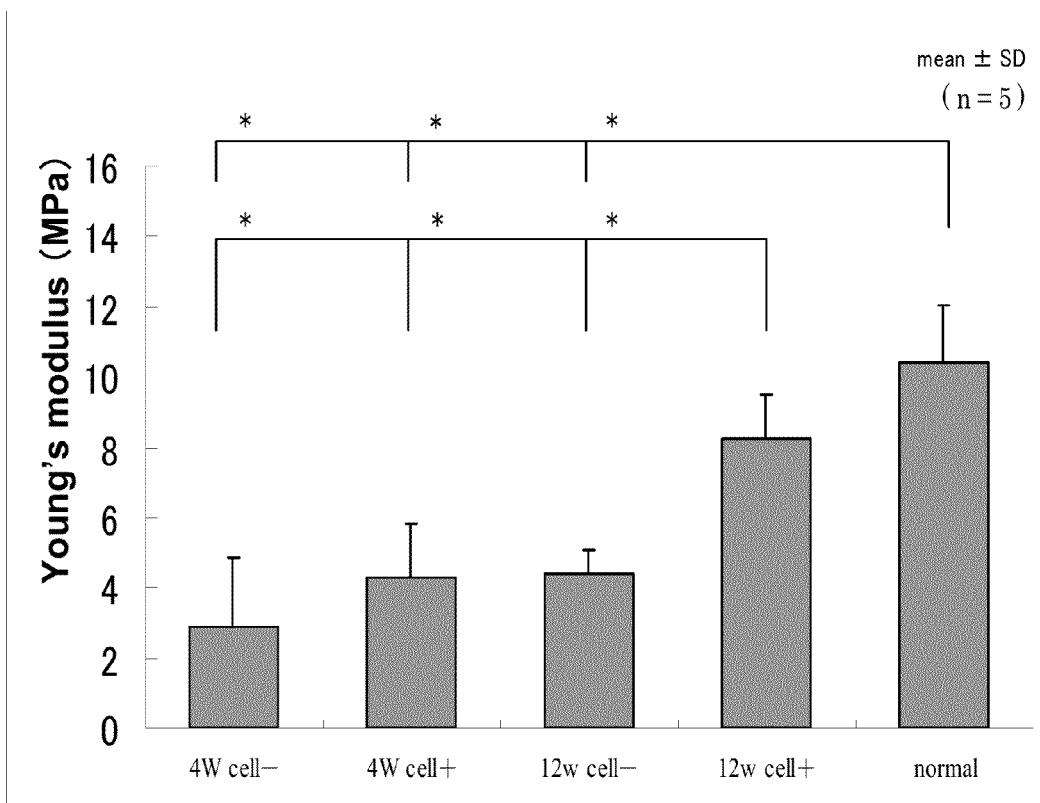
FIG. 13 is a graph showing the results of measuring mechanical strength for a purified alginate groups D) and E) in a rabbit cartilage repair model of Example 7.

The results of measuring mechanical strength for the purified alginate groups D) and E) are shown in FIG. 13.

As a result of measuring mechanical strength for the purified alginate groups, the mechanical strength in the purified alginate+cells group E) was a Young's modulus of 8 versus a Young's modulus of 10 in normal cartilage tissue, thus indicating that strength had recovered to nearly a normal, injury-free state. This finding also supported the claim that the composition of the present invention embedded with cells has superior mechanical strength, and is favorable with respect to regeneration of strong hyaline cartilage and the formation of subchondral bone.

EXAMPLE 8

Male Cadaver Model Having Undergone Appropriate Treatment

Method

A human male cadaver having undergone appropriate treatment was fixed with formalin. There was no instability or deformity of the knee at room temperature. The lateral condoyle of the femur was exposed using a medial parapatellar approach. The articular cartilage was smooth and there was no degeneration or deterioration observed. A full-thickness cartilage defect measuring 10 mm×20 mm in width and 5 mm in depth was produced at the maximum weight-bearing section of the medial condoyle using several types of punches and then sutured. An arthroscope was inserted at a 30° angle from the anterolateral side. All surgical instruments were inserted from the anterolateral side. After applying physiological saline to the affected area, liquid remaining in the joint was drained followed by wiping with a dry cotton swab. 2% w/v purified sodium alginate solution (no cells) colored with trypan blue and having a viscosity of 5000 to 6000 mPa·s was slowly injected into the cartilage defect with a syringe with an 18G needle. Although the affected area was facing downward at the time of the procedure, the composition of the present invention did not run out of the injury lesion and remained therein. 10 ml of 100 mM $CaCl_2$ solution was applied to the affected area to gel the surface. The knee joint was adequately washed by refluxing with physiological saline and the affected area was filled with 20 ml of physiological saline to prevent drying.

Following the procedure, the knee was manually extended and flexed over a range of 0 to 120° 200 times each at six hour intervals. The affected area was evaluated 24 hours after the procedure.

Results

Photographs depicting this experiment are shown in FIG. 14. FIG. 14A is a photograph showing the creation of the cartilage defect. In addition, FIG. 14B shows the colored sodium alginate solution transplanted into the cartilage defect. FIG. 14C shows the surface of the sodium alginate being gelled (cured) by application of $CaCl_2$ solution. Finally, FIG. 14D shows the results of observing movement of the joint 24 hours after surgery.

This experiment was conducted to confirm whether the composition of the present invention can be transplanted in the case of having created a large defect not only in rabbits, but also in a human cadaver.

As shown in the photograph of FIG. 14B, the sodium alginate solution did not run out of the affected area even if the surface of the sodium alginate solution was not gelled following injection into the defect. In addition, the sodium alginate solution remained in the defect even after the joint had been moved after surgery and observed 24 hours later following gelation of the surface of the sodium alginate solution. It was surprising to find that a composition of this form was able to remain in the defect at a site subjected to harsh conditions consisting of the application of a load and violent movement. On the basis of this finding, the composition for regenerating cartilage or treating a cartilage disease of the present invention was determined to have physical properties enabling it to be applied to a wide range of clinical applications with respect to various forms of cartilage injuries and conditions of use.

EXAMPLE 9

Technique for Forming One to Multiple Small Holes in a Cartilage Injury Lesion (1) First Example In cases in which there is cartilage remaining at a cartilage injury lesion or cartilage defect, one to multiple comparatively small-diameter full-thickness defects having a diameter of about 1.5 mm and depth of about 5 to 10 mm and extending to the subchondral bone are produced in a cartilage injury lesion or residual cartilage using a power drill according to the method of Examples 7 and 8. After slowly injecting therein a purified sodium alginate solution (no cells) having a viscosity of 3000 to 4000 mPa·s with an 18G needle, 1.0 ml of 100 mM CaCl$_2$ solution are applied to the surface of the sodium alginate solution injected into the defect to gel the surface thereof. As a result of producing the full-thickness defect(s), bleeding occurs from the patient's bone marrow enabling cartilage precursor cells in the bone marrow to migrate to the cartilage defect. Cartilage regeneration is promoted by the effects of the migrated cartilage precursor cells and the composition of the present invention, thereby making it possible to improve the function of the entire cartilage.

(2) Second Example

A partial defect not extending to the subchondral bone is produced in a cartilage injury lesion or cartilage defect in which residual cartilage is present similar to the first example described above. Purified sodium alginate solution (no cells) having a viscosity of 2000 to 3000 mPa·s and 100 mM CaCl$_2$ solution are then applied in the same manner as the first example. Since there is no bleeding into the defect from the patient's bone marrow, there is no infiltration of cartilage precursor cells in the subject's bone marrow. However, in this case as well, as a result of applying the composition to small diameter holes, the effects of the composition of the present invention are demonstrated, regeneration of cartilage is favorable, and the function of the entire cartilage can be improved. These techniques are effective in cases in which a cartilage injury lesion covers a wide area and cases in which residual damaged cartilage is present.

EXAMPLE 10

Test of Adherence of Sodium Alginate Solution

The relationship between viscosity and adherence of the composition of the present invention was examined using an aqueous sodium alginate solution (Kimica Corp.).

Method

Aqueous sodium alginate solutions (Table 2) were prepared using three types of sodium alginate solutions for which the viscosity of a 1% aqueous sodium alginate solution demonstrates a value of 110, 360 or 570 mPa·s as a result of having different molecular weights. A predetermined amount of each solution was poured into a centrifuge microtube (inner diameter: 9 mm, height: 39 mm) while preventing the entrance of air bubbles followed by promptly measuring the amount of time until each solution begins to run out of the microtube when inclined at an angle of 135°.

At this time, the viscosities of the sodium alginate solutions were measured using a B-type viscometer (Toki Sangyo Co., Ltd., Japan) at a temperature of 20° C.

TABLE 2

| | Sample | | | | | | |
|---|---|---|---|---|---|---|---|
| Aqueous sodium alginate solution | | Concentration (%) | | | | | |
| 1% viscosity | 110 mPa·s | 0.5 | 1.0 | 1.5 | 2.0 | 2.5 | 3.0 |
| | 360 mPa·s | 0.5 | 1.0 | 1.5 | 2.0 | 2.5 | 3.0 |
| | 570 mPa·s | 0.5 | 1.0 | 1.5 | 2.0 | 2.5 | 3.0 |

Results

Figure 15:
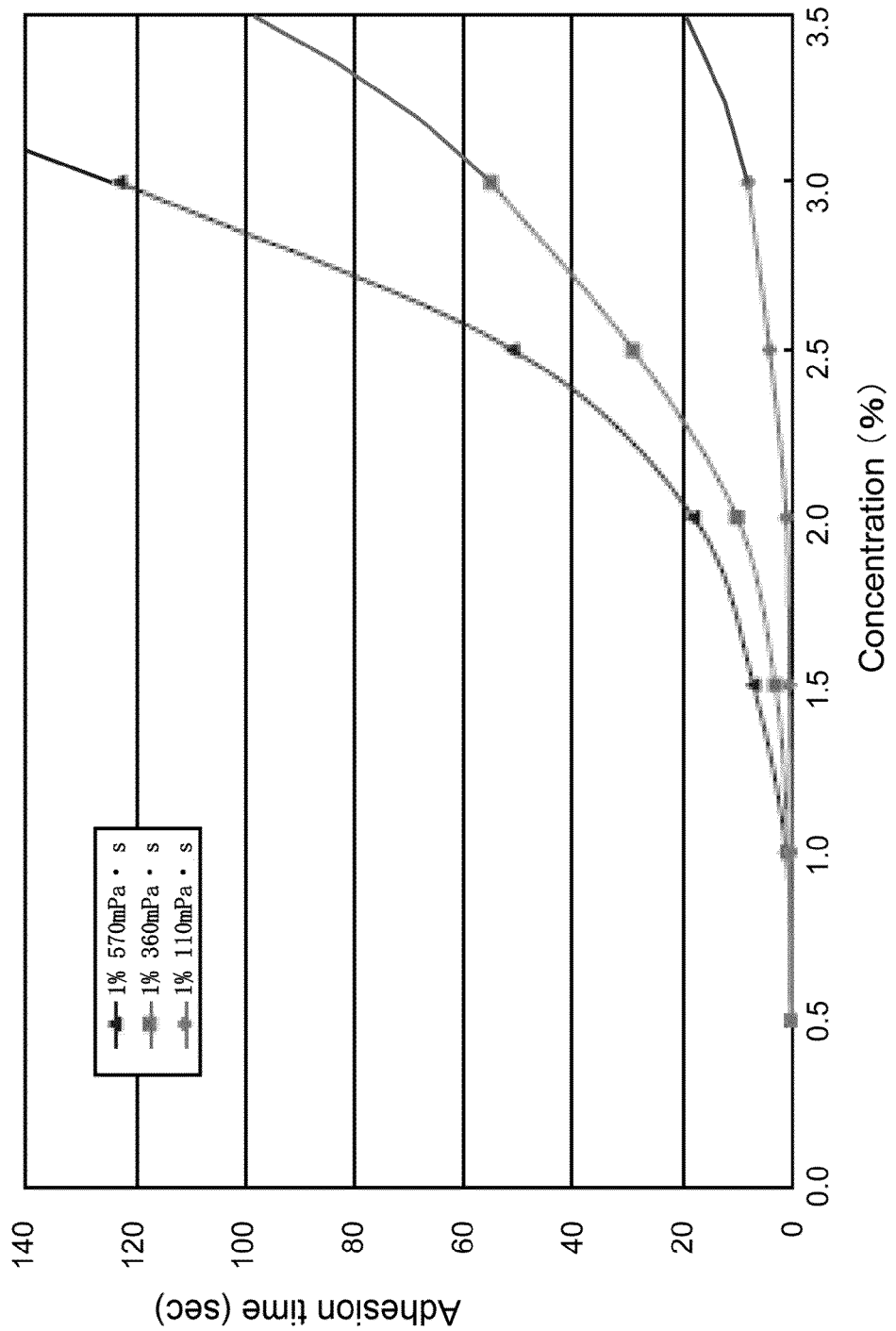
FIG. 15 is a graph showing the relationship between the concentrations (%) and adhesion times (sec) of various sodium alginate solutions.

The relationships between the concentration of each sodium alginate solution and adhesion time are shown in FIG. 15. The adhesion times of each of the three types of sodium alginate solutions increased as the concentration of the solutions became higher, and adherence was determined to increase. In addition, a comparison of the three types of sodium alginate solutions revealed that selection of a sodium alginate solution having a high viscosity at a concentration of 1% yielded high adherence and allow the obtaining of a longer adhesion time.

Figure 16:
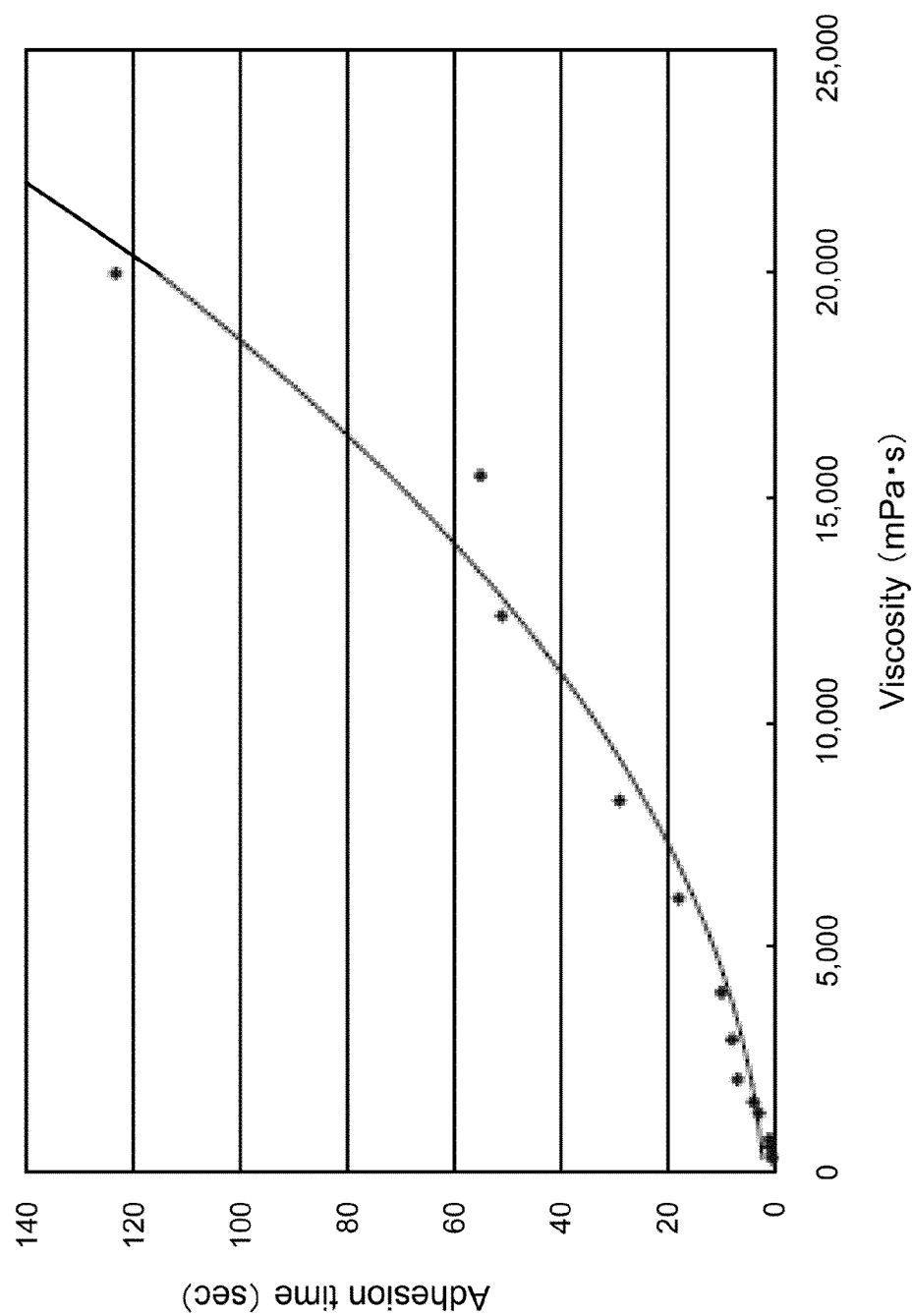
FIG. 16 is a graph showing the relationship between viscosity (mPa·s) and adhesion time (sec) of a sodium alginate solution.

The relationships between the viscosity of each type of sodium alginate solution and adhesion time are shown in FIG. 16. Adhesion time became longer and higher adherence was demonstrated as the viscosities of the sodium alginate solutions increased. Thus, a constant correlation was demonstrated to be obtained between viscosity and adherence of a composition containing a monovalent metal salt of alginic acid.

On the basis of these findings, when applying the composition of the present invention to a cartilage defect in the state of being inclined or facing downward, and when moisture, blood and the like at the affected area has been removed and the conditions of this experiment have been satisfied, the viscosity of the composition of the present invention can be adjusted on the basis of this result. For example, the viscosity of the composition of the present invention can be adjusted to about 2000 mPa·s or more to obtain an adhesion time of about 5 seconds, to a viscosity of about 3000 to 4000 mPa·s or more to obtain an adhesion time of about 10 seconds, to about 7000 to 8000 mPa·s or more to obtain an adhesion time of about 20 seconds, and to a viscosity of about 8000 to 9000 mPa·s or more to obtain an adhesion time of about 30 seconds.

However, in the case of actually applying to an affected area, the adhesion time varies according to such factors as the amount of the composition injected and the shape of the injected site. Particularly in cases in which only a small amount of the composition is injected, since factors such as surface tension also have an effect in addition to viscosity, long-term adherence is possible even at a low viscosity.

The target adhesion time can be obtained according to the type of procedure used by suitably taking into consideration other factors such as the characteristics of the viscometer used for measurement, room temperature, amount of embedded cells and state of the composition of the present invention.

EXAMPLE 11

Measurement of Molecular Weight Distribution of Purified Sodium Alginate (1) Method The molecular weight distribution of purified sodium alginate was measured by gel filtration chromatography under the conditions indicated below.

Column: TSKgel GMPWxl, 2 columns+TSKgel G2500PWxl, 1 column (Tosoh Corp.) (diameter 7.8 mm×300 mm×3 columns)
Column temperature: 40° C.
Eluate: 200 mM aqueous sodium nitrate solution
Sample concentration: 0.05%
Flow rate: 1.0 mL/min
Injection volume: 200 μL
Detector: RI (differential refractometer)
Standards: Pullulan, glucose (molecular weights: 1,600,000, 788,000, 404,000, 212,000, 112,000, 47,300, 22,800, 11,800, 5900, 180)

(2) Results

TABLE 3

| Measurement sample | Number average molecular weight (Mn) | Weight average molecular weight (Mw) | Variance ratio (Mw/Mn) | (Reference) Viscosity of a 1% aqueous solution |
|---|---|---|---|---|
| Purified sodium alginate (Kimica Corp., Mochida International Ltd., Sea Matrix ™ (sterilized), Serial No. B5Y01) | 430,000 | 1,700,000 | 4.0 | 400 to 500 mPa·s |
| Purified sodium alginate (Pronova ™ SLG20, FMC Biopolymer Inc. | 66,000 | 440,000 | 6.6 | 20 to 100 mPa·s |

(3) Discussion

The weight average molecular weight of the purified sodium alginate used in the rabbit cartilage repair model of Example 7 was 1,700,000 as measured using the method described above. As indicated in Example 7, the sodium alginate demonstrated hyaline cartilage regenerative effects in the rabbit cartilage repair model both with and without cells. On the other hand, although a similar experiment was conducted using low endotoxin alginic acid (Pronova™ LVG, currently Pronova™ UP LVG, FMC Biopolymer Inc.) as described in Reference 5, it is disclosed that fibrous cartilage is formed in the case of applying only alginic acid not containing cells to a cartilage defect. Furthermore, the sterilized version of Pronova™ LVG is designated as Pronova™ SLG20, the weight average molecular weight thereof as determined by the method described above was 440,000. Although Sea Matrix™ and Pronova™ have a common characteristic of being low endotoxin alginic acids, their alginic acids differ in terms of molecular weight, and this difference is thought to lead to differences in cartilage regenerative effects. Although viscosity can be adjusted by the concentration of alginic acid, in an experiment in which different concentrations of alginic acid gels (0.5 to 4%) were embedded with chondrocytes, transplanted beneath the skin of mice and confirmed for the generation of cartilage, the concentration of alginic acid was reported to not have an effect on cartilage generation effects (Keith T. Paige et al., "De Novo Cartilage Generation Using Calcium Alginate-Chondrocyte Constructs", Plastic and Reconstructive Surgery, Vol. 97: 1996, p. 168-178). Thus, the difference in cartilage regenerative effects between Sea Matrix™ and Pronova™ is thought to be attributable to molecular weight. Namely, although the use of low endotoxin alginic acid allows the obtaining of a composition having high bioaffinity with low levels of degeneration and inflammatory responses in surrounding cartilage, by also using alginic acid having a high molecular weight, it was found that a composition for regenerating cartilage or therapeutic composition can be obtained that has extremely superior cartilage regenerative effects allowing regeneration of cartilage even without embedding cells therein. Low endotoxin alginic acid having a weight average molecular weight of at least 500,000 or more, and preferably 650,000 or more, is useful for cartilage regeneration, which that having a weight average molecular weight of 1,000,000 to 2,000,000 was found to be more preferable, and that having a weight average molecular weight of about 1,500,000 to 2,000,000 was found to be particularly preferable.

EXAMPLE 12

Rabbit Osteoarthritis Model (Anterior Cruciate Ligament (ACL) Resection Model)

(1) Method

An OA model was created in both knee joints of female Japanese white rabbits (body weights: 2.6 to 2.9 kg) in accordance with the method of Vignon, E. et al. (Vignon, E., Bejui, J., Mathieu, P., Hartmann, J D, Ville, G., Evreux, J C, et al., Histological cartilage changes in a rabbit model of osteoarthritis, J. Rheumatol., 1987:14 (Spec No): 104-6). Three animals each (6 knees) were assigned to the following four groups.

A) Control group (physiological saline)
B) 1% sodium hyaluronate solution dose group (molecular weight: approx. 900,000, viscosity: approx. 2300 mPa·s)
C) 1% purified sodium alginate solution dose group (molecular weight: approx. 1,700,000, viscosity: approx. 500 mPa·s)
D) 2% purified sodium alginate solution dose group (molecular weight: approx. 1,700,000, viscosity: approx. 5000 mPa·s)

The solutions of B) to D) were prepared using physiological saline. The purified sodium alginate of C) and D) were the same as the purified sodium alginate used in Examples 1 and 7 (Kimica Corp., Mochida International Ltd., Sea Matrix (sterilized), Serial No. B5Y01).

Following resection of the anterior cruciate ligament, each of the solutions A) to D) above were administered into the articular cavity in weeks 4, 5, 6, 7 and 8 (total of 5 administrations given once per week). The solutions were administered using a 27G needle by penetrating the patellar tendon and injecting 0.3 mL/knee per administration. The rabbits were sacrificed in week 9 to acquire knee joint tissue specimens. Inflammation from infections, foreign body reactions and the like were not observed in any of the knees.

(2) Results (General Observations)

Figure 17:
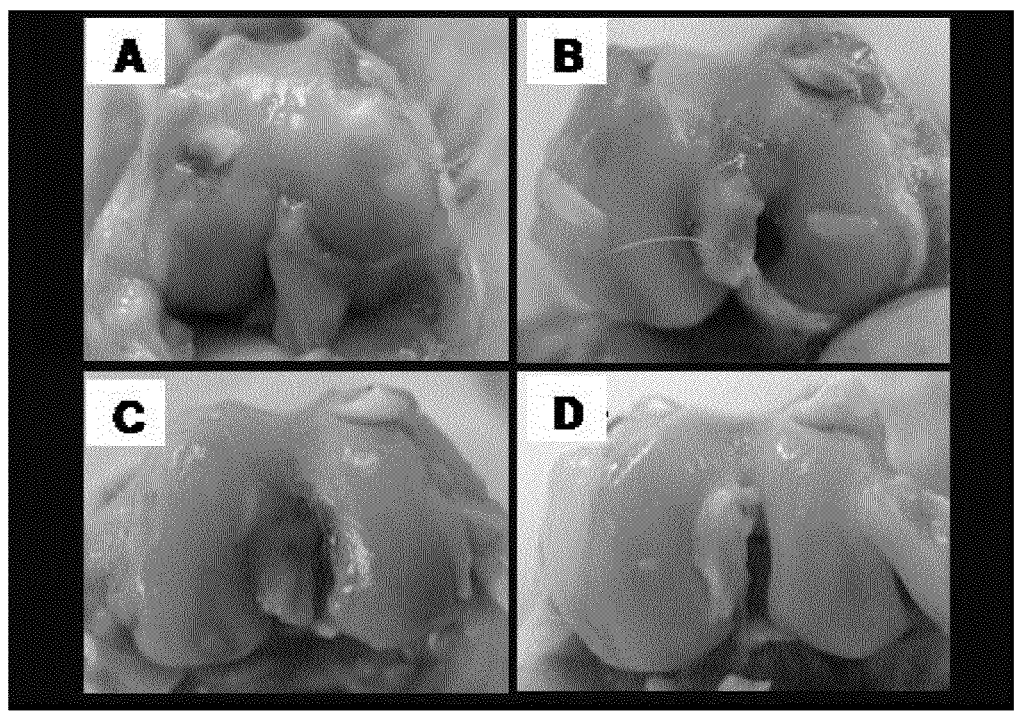
FIG. 17 shows photographs of the appearance of knee joints in a rabbit osteoarthritis model of Example 12.

The appearance of the entire knee joint (knee articular cartilage of the femur and tibia) was observed macroscopically. Those results are shown in FIG. 17. In group A (physiological saline dose group), numerous findings of osteoarthritis, including cartilage defects and osteophytes, were observed macroscopically. The degree of cartilage injury (size, depth) was milder in the other groups than in group A. Scoring of the macroscopic findings yielded similar results.

(Staining)

Figure 18:
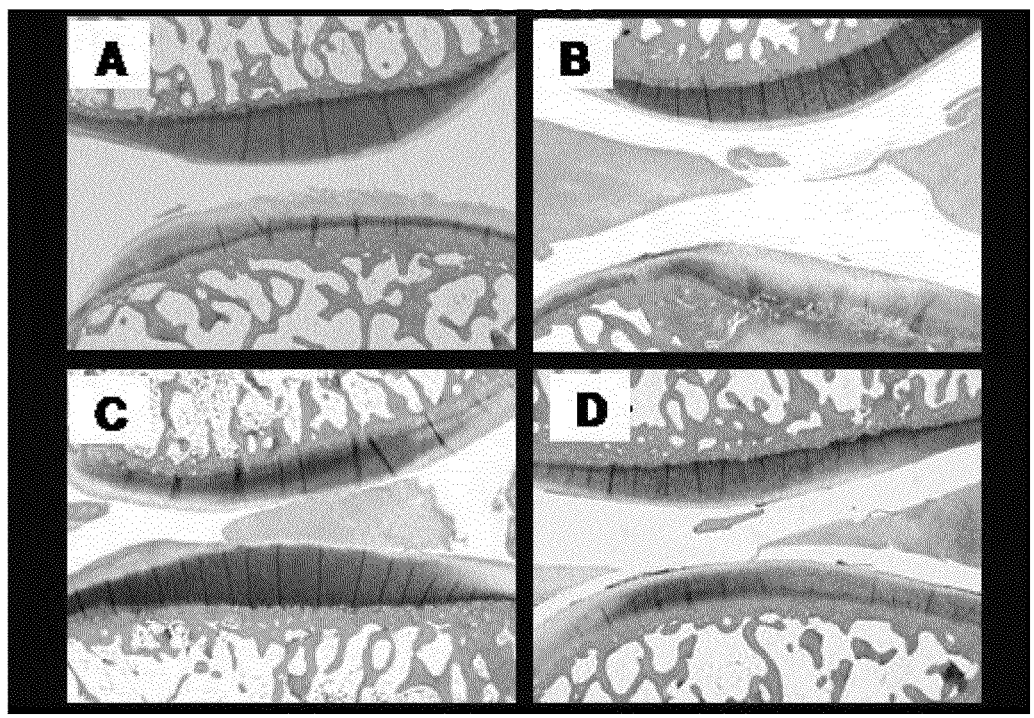
FIG. 18 shows photographs of tissue staining of knee joint tissue in a rabbit osteoarthritis model of Example 12.

The knee joint tissue specimens were fixed with paraformaldehyde, decalcified and embedded in paraffin. The specimens were evaluated histologically by safranin-O staining Those results are shown in FIG. 18. The upper portions of each figure indicate femoral cartilage, while the lower portions indicate tibial cartilage, and cartilage degenerative changes were assessed in cartilage at both locations. Decreased staining of cartilage matrix and increased coarseness of cartilage surface were observed in group A (physiological saline dose group). In group B (1% sodium hyaluronate solution dose group), although cartilage surface was smoother than in group A, decreased staining was observed. In group C (1% purified sodium alginate solution dose group) and group D (2% purified sodium alginate solution dose group), cartilage surface was smooth and decreases in staining were mild as compared with groups A and B. In addition, residual alginic acid was present on the cartilage surface.

On the basis of the above findings, intra-articular injection of sodium alginate demonstrated action that inhibited cartilage degeneration and protected cartilage in an ACL resection OA model, and effects were observed that were equal to or better than administration of 1% sodium hyaluronate solution used as a therapeutic drug for osteoarthritis. In addition, since sodium alginate was adhered to the cartilage surface, sodium alginate was confirmed to demonstrate affinity with articular cartilage as well as cover and protect cartilage surfaces.

EXAMPLE 13

Evaluation of Therapeutic Effects of Alginic Acid of Different Molecular Weights in a Rabbit Osteoarthritis Model (Anterior Cruciate Ligament (ACL) Resection Model)

(1) Method

An OA model was created in both knee joints of female Japanese white rabbits (body weights: 2.6 to 2.9 kg) in accordance with the method of Vignon, E. et al. (Vignon, E., Bejui, J., Mathieu, P., Hartmann, J D, Ville, G., Evreux, J C, et al., Histological cartilage changes in a rabbit model of osteoarthritis, J. Rheumatol., 1987:14 (Spec No): 104-6). Five animals each (10 knees) were assigned to the following five groups.
A) Control group (physiological saline)
B) 1% sodium hyaluronate solution dose group (ARTZ (registered trademark), Kaken Pharmaceutical Co., Ltd., molecular weight: approx. 900,000, viscosity: approx. 2300 mPa·s)
C) 2% purified sodium alginate solution dose group (Pronova™ SLM$_{20}$, FMC Biopolymer Inc., molecular weight: approx. 400,000)
D) 2% purified sodium alginate solution dose group (Kimica Corp., sterilized, molecular weight: approx. 1,000,000)
E) 2% purified sodium alginate solution dose group (Sea Matrix (sterilized), Kimica Corp., molecular weight: approx. 1,700,000)

The solutions of C) to E) were prepared using physiological saline.

Following resection of the anterior cruciate ligament, each of the solutions A) to E) above were administered into the articular cavity in weeks 4, 5, 6, 7 and 8 (total of 5 administrations given once per week). The solutions were administered using a 27G needle by penetrating the patellar tendon and injecting 0.3 mL/knee per administration. The rabbits were sacrificed in week 9 to acquire knee joint tissue specimens. Inflammation from infections, foreign body reactions and the like were not observed in any of the knees.

(2) Results (General Observations)

Figure 19:
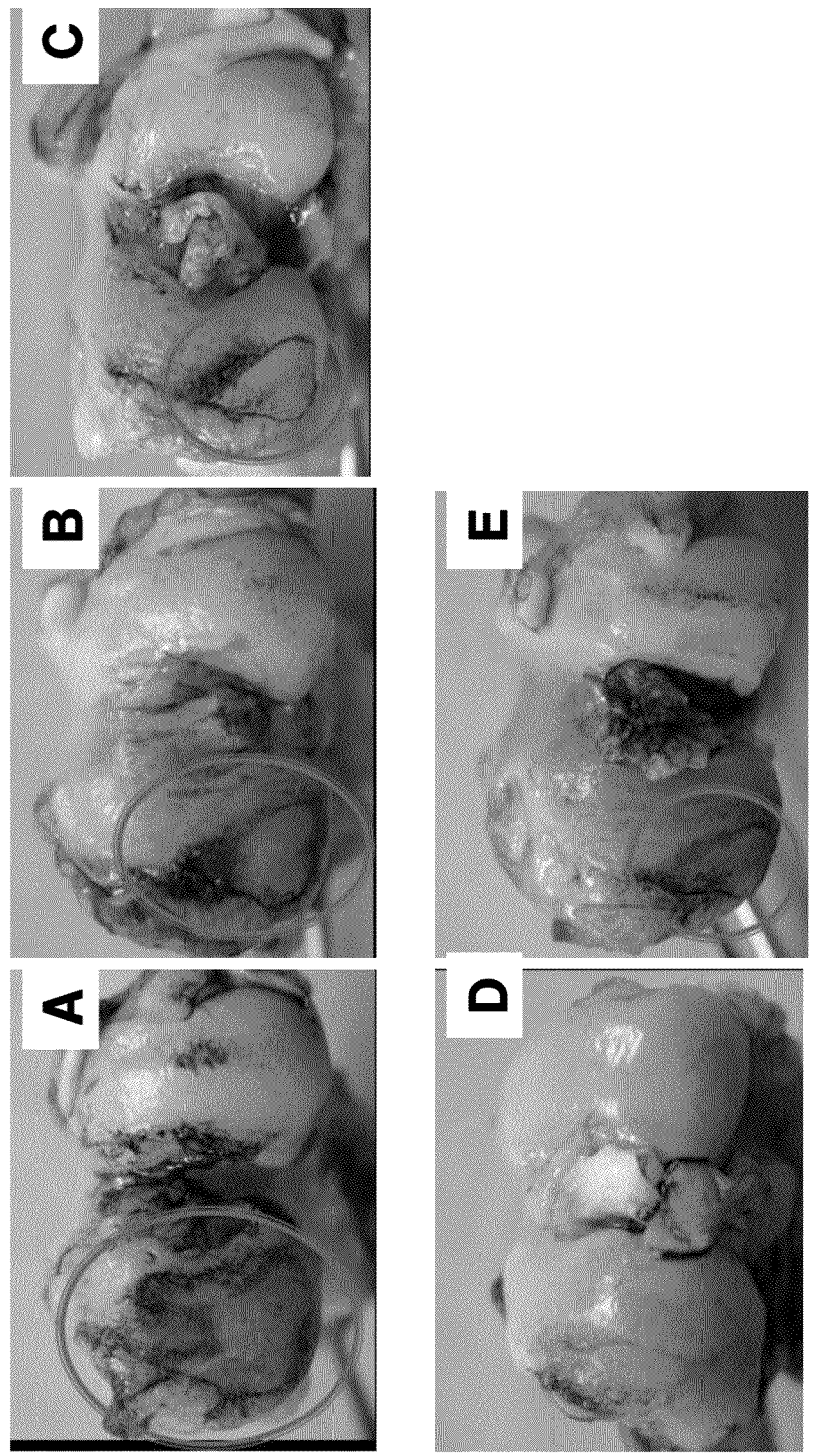
FIG. 19 shows photographs of the appearance of knee joints in a rabbit osteoarthritis model of Example 13 after staining with India ink. In the photographs, the encircled areas indicate boundaries between cartilage injury lesions stained with India ink and normal cartilage. A) Control group; B) 1% sodium hyaluronate dose group; C) 2% sodium alginate dose group (molecular weight: 400,000); D) 2% sodium alginate dose group (molecular weight: 1,000,000); E) 2% sodium alginate dose group (molecular weight: 1,700,000). Furthermore, the photographs show examples of multiple specimens.
Figure 20:
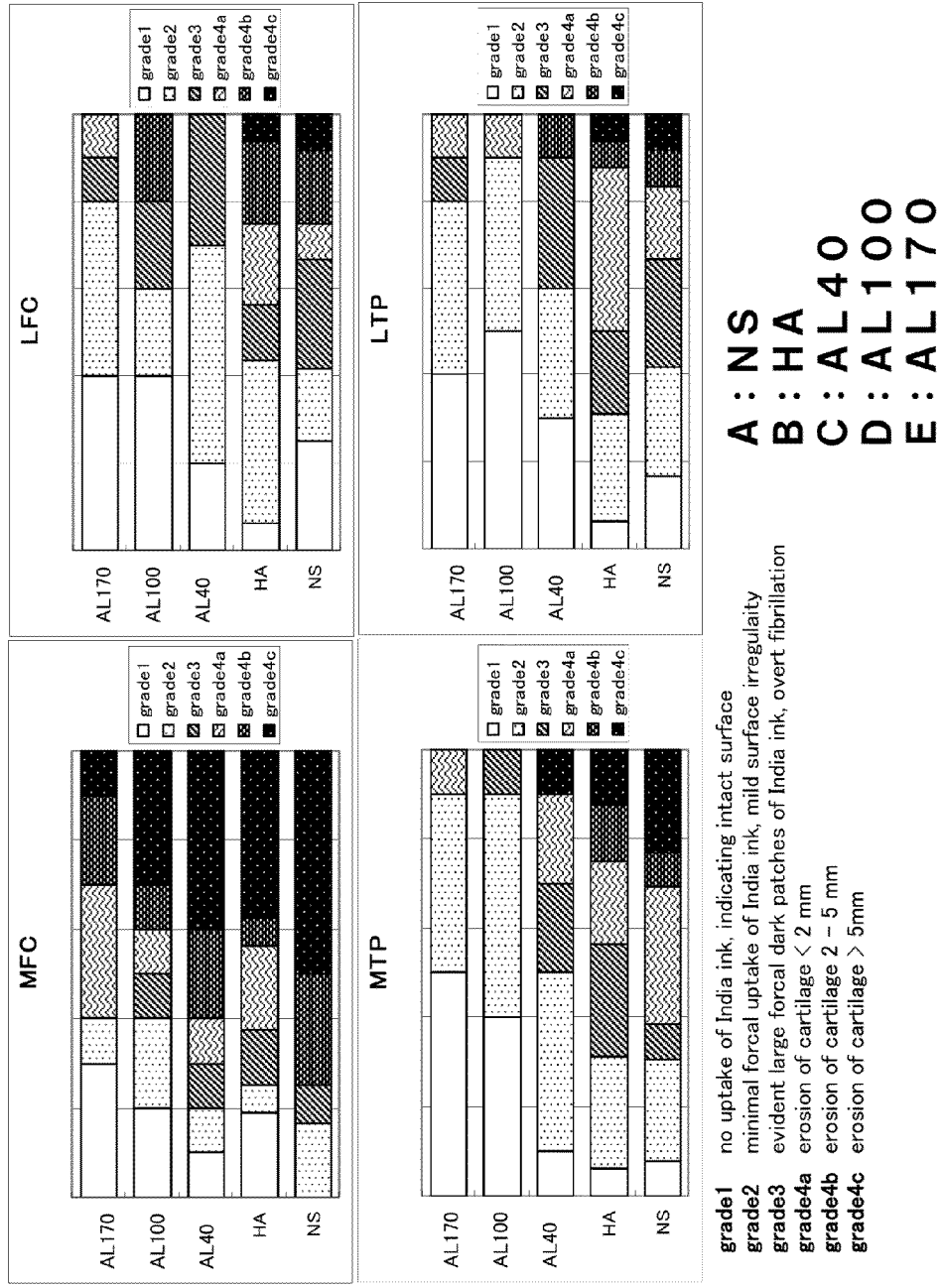
FIG. 20 shows the results of scoring macroscopic findings of knee joints stained with India ink in a rabbit osteoarthritis model of Example 13. NS, HA, AL40, AL100 and AL170 respectively correspond to A) to E) (same as FIG. 19). Grade 1 indicates an uninjured surface not stained with India ink (no uptake of India ink, indicating intact surface). Grade 2 indicates focal staining with India ink and mild injury to the surface (minimal focal uptake of India ink, mild surface irregularity). Grade 3 indicates large, well-defined staining with India ink and obvious fibrillation (evident large focal dark patches of India ink, overt fibrillation). Grade 4a indicates cartilage erosion of less than 2 mm (erosion of cartilage <2 mm). Grade 4b indicates cartilage erosion of 2 to 5 mm (erosion of cartilage 2-5 mm). Grade 4c indicates cartilage erosion of greater than 5 mm (erosion of cartilage >5 mm).

The appearance of the entire knee joint (knee articular cartilage of the femur and tibia) was observed macroscopically. In order to evaluate the degree of injury to the cartilage surface, the specimens were stained in India ink in accordance with the method of Choji Shimizu et al. and then scored (J. Rheumatol., Vol. 25, pp. 1813-1819, 1998). Macroscopic findings are shown in FIG. 19. When staining with India ink, boundaries between cartilage injury lesions and normal cartilage are colored. In group A (physiological saline dose group), numerous findings of osteoarthritis, including deep and wide-ranging cartilage defects and osteophytes, were observed macroscopically. The degree of cartilage injury (size, depth) was milder in the other groups than in group A. The results of scoring the macroscopic findings are shown in FIG. 20. The knee joints were observed at four locations consisting of the Medial Femoral Condyle (MFC), Medial Tibial Plateau (MTP), Lateral Femoral Condyle (LFC) and Lateral Tibial Plateau (LTP). The degree of cartilage injury was milder in groups B to E than in group A at all of these sites. In addition, the degree of cartilage injury tended to be milder in groups D and E than in groups B and C. Differences in cartilage degenerative change inhibitory effects, cartilage protective effects and cartilage repair effects were thought to be present due to differences in molecular weight of alginic acid.

(Proteoglycan Staining)

Figure 21:
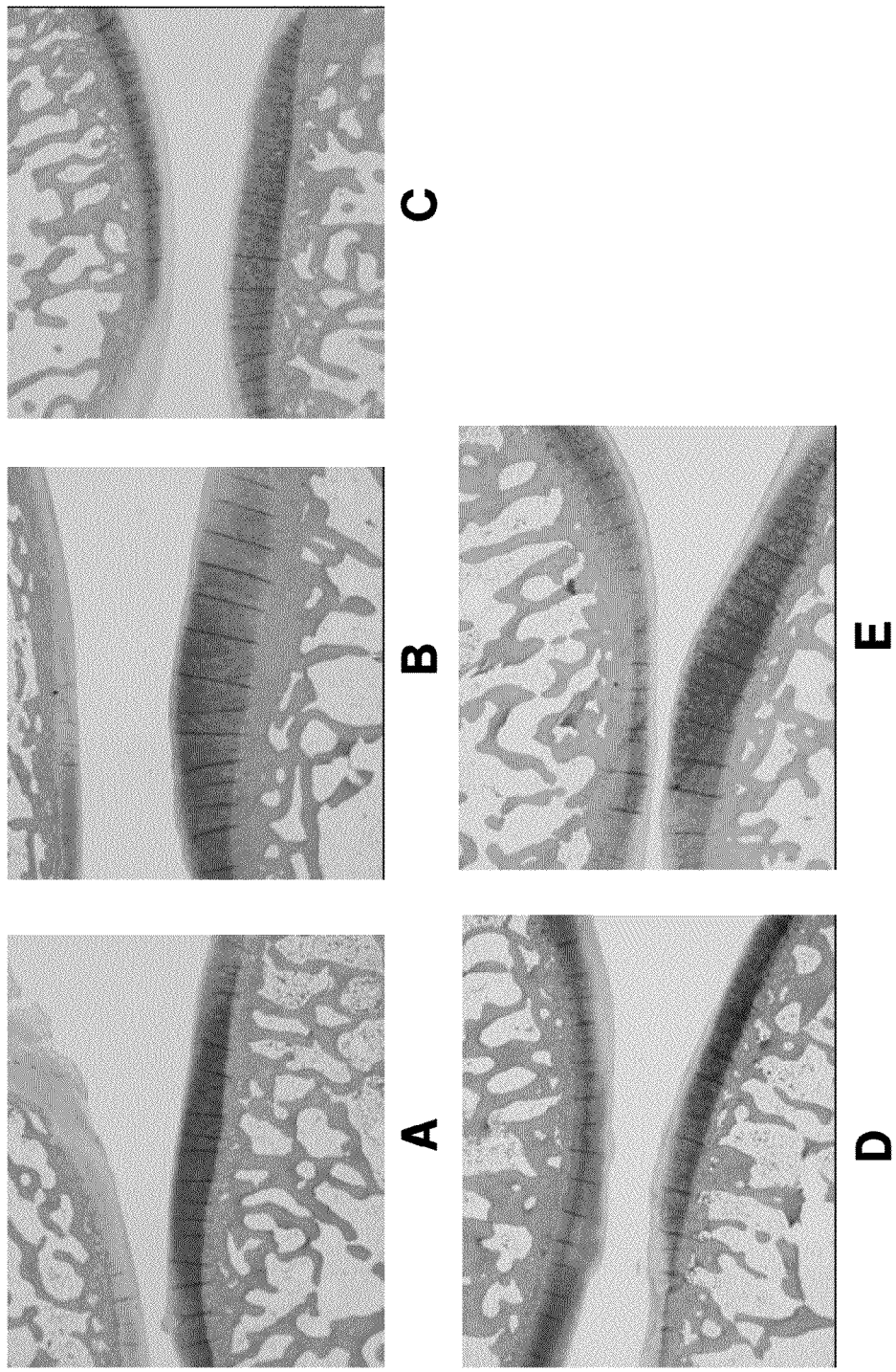
FIG. 21 shows photographs of staining of knee joint tissue with Safranin-O in a rabbit osteoarthritis model of Example 13. A) to E) are the same as in FIG. 19. Furthermore, the photographs show examples of multiple specimens.

The knee joint tissue specimens were fixed in paraformaldehyde, decalcified and embedded in paraffin. The specimens were evaluated histologically by safranin-O staining Those results are shown in FIG. 21. The upper portions of each figure indicate femoral cartilage, while the lower portions indicate tibial cartilage, and cartilage degenerative changes were assessed in cartilage at both locations. Decreased staining of cartilage matrix and increased coarseness of cartilage surface were observed in group A (physiological saline dose group). In group B (1% sodium hyaluronate solution dose group), although cartilage surface was smoother than in group A, decreased staining was observed. In the sodium alginate solution dose groups (groups C to E), cartilage surface was smooth and decreases in staining were mild as compared with groups A and B. In addition, residual alginic acid was present on the cartilage surface.

(Overall Histopathological Evaluation)

Macroscopic observations and observations by staining were comprehensively evaluated by scoring in accordance with the method of Toshiyuki Kikuchi et al. to evaluate effects of the administered drugs (Osteoarthritis and Cartilage, Vol. 4, pp. 99-110, 1996). Medial femoral condyle were evaluated to one of four levels for the 8 parameters indicated below, and the total score was used as an osteoarthritis lesion score.

(1) Loss of cartilage surface, (2) cartilage erosion, (3) fibrosis and cracking, (4) loss of stainable proteoglycan, (5) disturbances in chondrocyte arrangement, (6) loss of chondrocytes, (7) loss of subchondral bone, and (8) formation of chondrocyte clusters.

ANOVA was used to test for the presence of a significant difference between groups, and subsequent comparisons between each group were made at a level of significance of $p<0.05$ using a post hoc test.

Figure 22:
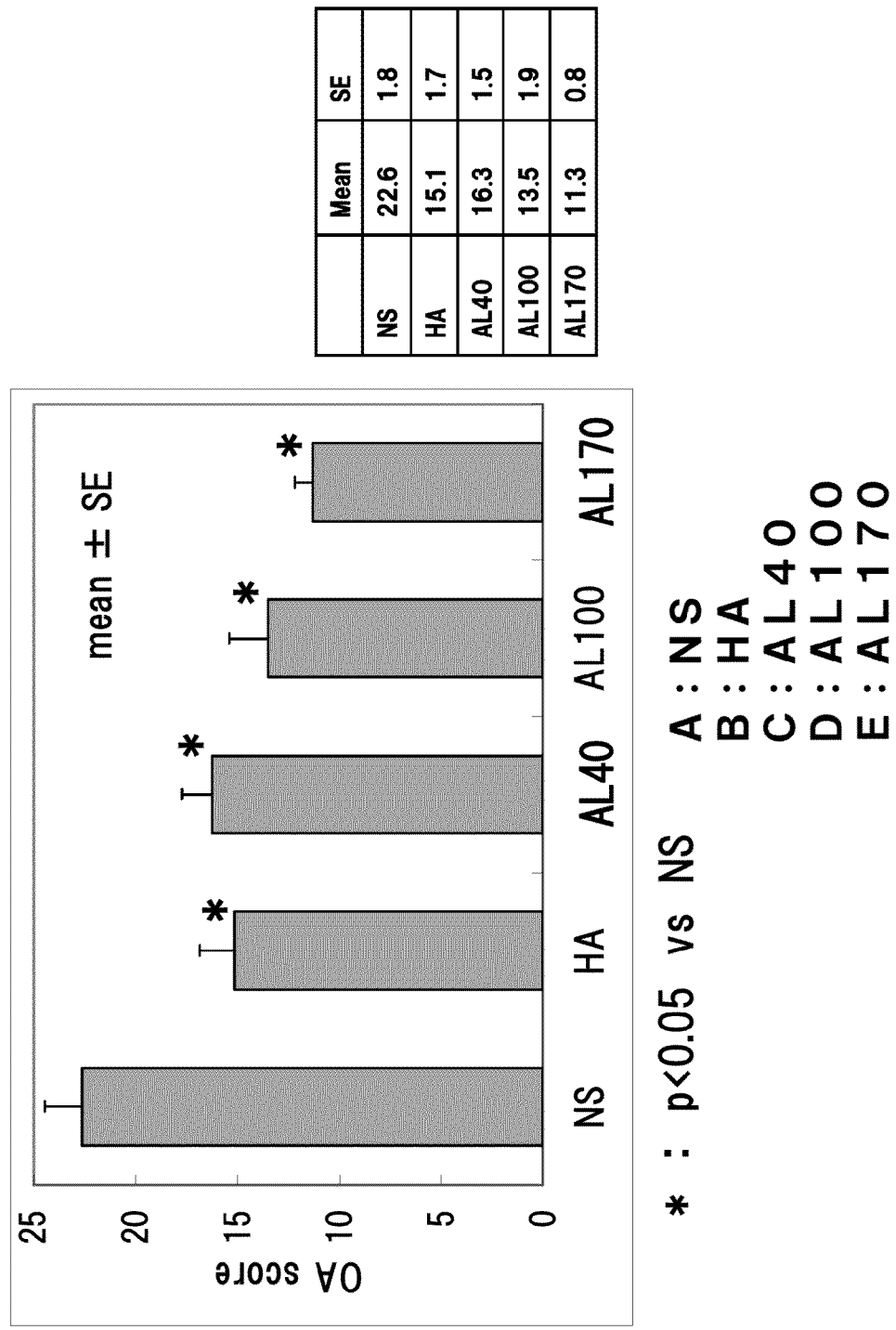
FIG. 22 shows the results of scoring general histopathological evaluations in a rabbit osteoarthritis model of Example 13. NS, HA, AL40, AL100 and AL170 respectively correspond to A) to E) (same as FIG. 19).

The results are shown in FIG. 22. Osteoarthritis lesion scores were significantly lower in groups B to E versus group A. In addition, although superior effects were observed in the high molecular weight alginic acid dose groups (groups D and E) as compared with the hyaluronic acid dose group (group B), effects of the low molecular weight alginic acid dose group (group C) were about the same as those of the hyaluronic acid dose group.

On the basis of the above findings, intra-articular injection of sodium alginate demonstrated action that inhibited cartilage degenerative changes and protected cartilage in an ACL resection OA model, and effects were observed that were equal to or better than administration of 1% sodium hyaluronate solution used as a therapeutic drug for osteoarthritis. In particular, high molecular weight alginic acid demonstrated superior therapeutic effects to hyaluronic acid. Furthermore, although the three types of alginic acid differed in terms of viscosity, since alginic acid having viscosity lower than that of hyaluronic acid is observed to demonstrated effects equal to or greater than those of hyaluronic acid, differences in therapeutic effects are thought to be attributable to differences in the substance used and molecular weight rather than differences in viscosity.

In the ACL resection OA model used in this experiment, the drugs were administered starting 4 weeks after ACL resection. Thus, decreases in osteoarthritis lesion scores observed in the drug dose groups are thought to be the combined result of effects inhibiting the progression of lesions due to inhibition of cartilage degenerative changes and protection of cartilage, as well as cartilage repair action on cartilage injuries that had already occurred. According to the paper by the above-mentioned Toshiyuki Kikuchi cited as a reference in this experiment, OA scores are reported to reach 20 to 25 in physiological saline dose groups. Since drug administration was started in week 4 after ACL resection in this experiment, there is the possibility that OA scores decreased as a result of improvement of cartilage status due to the effects of the drugs as a result of starting administration from a state in which OA scores were about 20 to 25. In addition, since the score for normal joints is 8 in the evaluation system used in this experiment, the mean OA score (11.3) in group E (alginic acid having a molecular weight of 1,700,000) can be said to approach the score for normal joints and be an extremely good score.

EXAMPLE 14

Study of Method of Measuring Molecular Weight of Alginic Acid

Different values are known to be obtained when measuring the molecular weight of high molecular weight substances derived from a natural origin depending on the measurement method. According to ASTM F2064-00 (ASTM International Publication (2006); the American Society for Testing and Materials is an organization engaged in the international standardization and establishment of specifications of industrial material standards and testing method standards), the use of SEC-MALLS (Size Exclusion Chromatography with Multiple Angle Laser Light Scattering Detection) is recommended for measurement of molecular weight. Therefore, a comparison was made between measurement of the molecular weight of the sodium alginate used in Example 13 by SEC-MALLS and by gel filtration chromatography as described in Example 11. Furthermore, SEC-MALLS combines the use of a multiple angle laser light scattering detector (MALLS) with gel filtration chromatography.
(1) Method
Measurement by gel filtration chromatography was carried out in the same manner as Example 11. Measurement by SEC-MALLS was carried out under the conditions indicated below.
Multiple angle laser light scattering detector: DAWN HELEOS, Wyatt Technology
Column: Shodex SB-806M, 2 columns (Showa Denko K.K.)
Eluate: 200 mM Aqueous sodium nitrate solution
Flow rate: 1.0 mL/min
(2) Results

TABLE 4

| | AL170 | AL100 | AL40 |
|---|---|---|---|
| Weight average molecular weight as determined by gel filtration chromatography | 1,700,000 | 1,000,000 | 410,000 |
| Weight average molecular weight as determined by SEC-MALLS | 185,000 | 149,000 | 128,000 |
| (Reference) Pharmacological effects in Example 13 | Very good | Very good | Good |

The same purified (low endotoxin) sodium alginate used in Example 13 is used for AL170, AL100 and AL40.
AL170: Kimica Corp., Mochida International Ltd., Sea Matrix (sterilized), 1% viscosity: approx. 500 mPa·s
AL100: Kimica Corp., sterilized, 1% viscosity: approx. 100 mPa·s
AL40: FMC Biopolymer Inc., Pronova ™ SLM$_{20}$, 1% viscosity: approx. 30 mPa·s (3) Discussion
As shown in Table 4, differences in the molecular weights of three types of alginates as determined by SEC-MALLS were only observed within a range that did not definitively indicate a difference between them, and those values differed considerably from measurement results obtained by gel filtration chromatography. As shown in Example 13, since there were well-defined differences in pharmacological effects between the samples used, molecular weights determined by gel filtration chromatography were found to demonstrate a higher correlation with therapeutic effects of alginates than molecular weights as determined by SEC-MALLS, and molecular weights determined by gel filtration chromatography were found to be suitable as parameters for specifying a preferable molecular weight range of alginates used in the composition for regenerating cartilage or composition for treating a cartilage disease.

EXAMPLE 15

Figure 23:
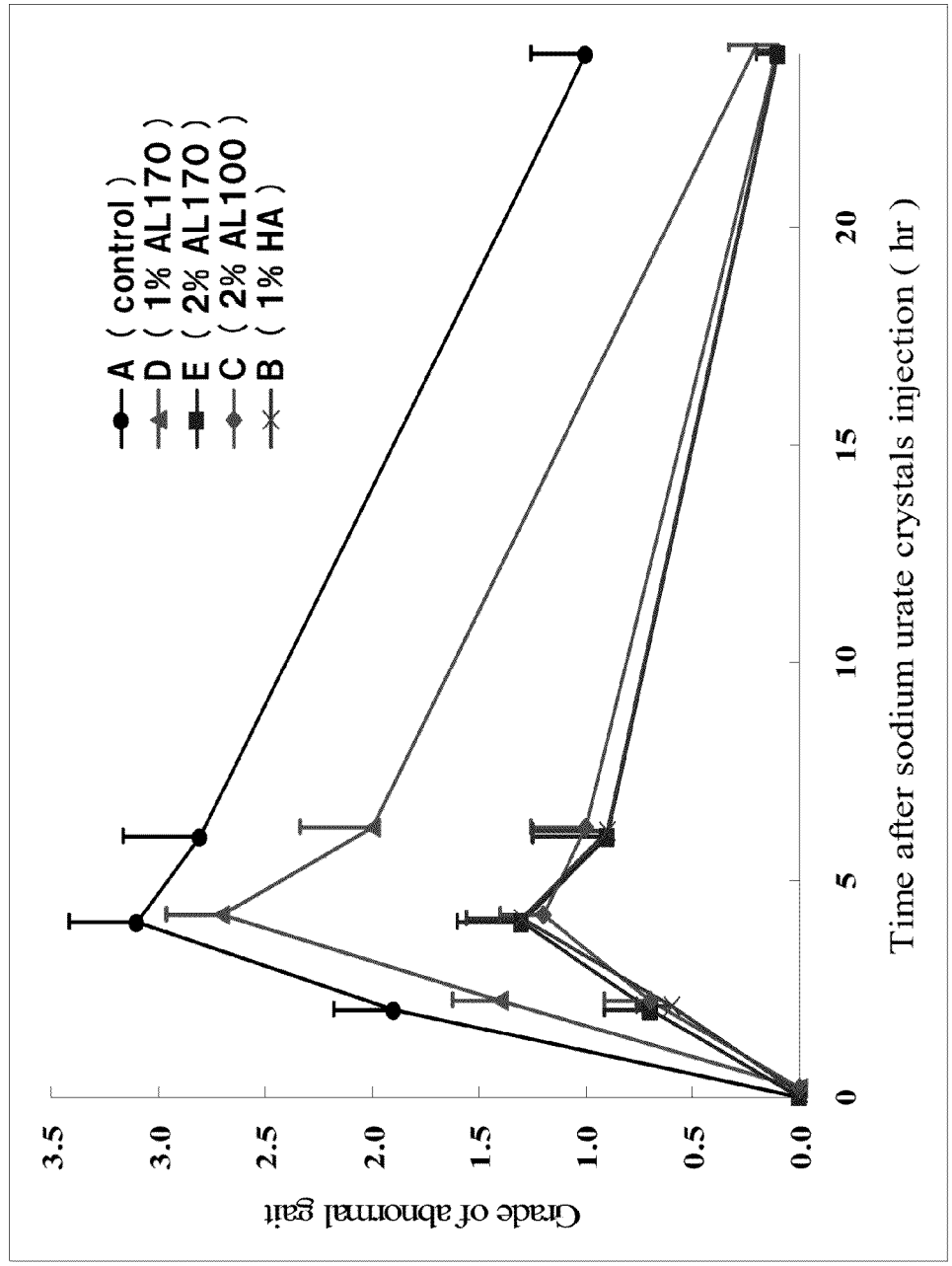
FIG. 23 shows time-based changes in gait scores in a rat experimental arthritis pain model of Example 15. A) Control group (NS); B) 1% sodium hyaluronate dose group (1% HA); C) 2% sodium alginate dose group (molecular weight: 1,000,000) (2% AL100); D) 1% sodium alginate dose group (molecular weight: 1,700,000) (1% AL170); E) 2% sodium alginate dose group (molecular weight: 1,700,000) (2% AL170). *: p<0.05 vs. NS.

Effects of Alginic Acid on Experimental Arthritis Pain in Rats (1) Method
Rats with arthritis induced by intra-articular injection of needle-shaped monosodium urate (MSU) crystals present with an abnormal gait due to pain. A experimental arthritis pain model in rats administered MSU was prepared in accordance with the method of Shizuhiko Ihara, et al. (Folia Pharmacol. Japon, Vol. 100, pp. 359-365 (1992)) to assess the effects of intra-articular administration of sodium alginate.
Male Crl:CD rats were purchased at age 5 weeks and used in the experiment following a one week acclimation period. 0.05 mL of a 5.0% physiological saline suspension of MSU were injected into the right knee joint of the rats under anesthesia followed by observation of gait at 2, 4, 6 and 24 hours after injection. Gait was evaluated by scoring to one of five grades consisting of normal gait (0 points), mild limping (1 point), moderate limping (2 points), walking on toes (3 points) and walking on three legs (4 points). Ten animals were assigned to each of the five groups indicated below.
A) Control group (physiological saline dose group)
B) 1% sodium hyaluronate solution dose group (ARTZ (registered trademark), Kaken Pharmaceutical Co., Ltd., molecular weight: approx. 900,000)
C) 2% purified sodium alginate solution dose group (Kimica Corp., sterilized, molecular weight: approx. 1,000,000)
D) 1% purified sodium alginate solution dose group (Sea Matrix (sterilized), Kimica Corp., molecular weight: approx. 1,700,000)
E) 2% purified sodium alginate solution dose group (Sea Matrix (sterilized), Kimica Corp., molecular weight: approx. 1,700,000)
50 µL of each solution were administered to the same site of the joint one hour prior to injection of MSU.
(2) Results and Discussion
Time-based changes in gait scores are shown in FIG. 23. The gait scores of the 1% sodium hyaluronate solution dose group (group B) and 2% sodium alginate solution dose groups (groups C and E) were significant lower than the control group (group A), and pain suppressive effects were observed. Dose-dependent pain suppressive effects were observed in a comparison of the 1% and 2% solutions containing sodium alginate having a molecular weight of about 1,700,00 (groups D and E). In addition, the 2% sodium alginate solutions having molecular weights of 1,000,000 and 1,700,000 demonstrated equal pain suppressive effects despite having different viscosities of about 300 mPa·s and about 5000 mPa·s, respectively.

In joints, MSU acts directly or indirectly on synovial cells and neutrophils, and is thought to cause arthritis through the production of cytokines and the like (above-mentioned publication by Shizuhiko Ihara, et al.). Namely, MSU induces pain as a result of inflammatory reaction being induced thereby. Sodium alginate solution demonstrated pain suppressive effects in this model, and effects observed were equal to those of sodium hyaluronate, which is used as a therapeutic drug for osteoarthritis and as a joint pain suppressive drug for chronic rheumatoid arthritis. A monovalent metal salt of alginic acid was confirmed to have effects that inhibit inflammation and pain, and is believed to be useful as a therapeutic drug for osteroarthritis, frozen shoulder and the like, while also being able to be applied to joint pain associated with rheumatoid arthritis.

INDUSTRIAL APPLICABILITY

Since the composition for regenerating cartilage of the present invention does not require an excessive surgical procedure and can be injected into a cartilage injury lesion, the surgical procedure is simple and cartilage regeneration, and particularly hyaline cartilage regeneration, can be effectively promoted without placing an excessive burden on the body in terms of harvesting chondrocytes, periosteum and the like.

The composition for regenerating cartilage of the present invention has gel curability as a result of being contacted with Ca ions at the affected area. The composition can be retained at the affected area by curing the surface thereof as a result of taking advantage of this property. In the case of embedding cells for cartilage tissue regeneration in the composition for regenerating cartilage of the present invention, the cells are easily dispersed in the cured gel. The composition can be used for various forms of cartilage injuries, and is able to accommodate various application conditions.

The composition for regenerating cartilage of the present invention is able to demonstrate hyaline cartilage regenerative effects even without containing cells as a result of containing a low endotoxin monovalent metal salt of alginic acid. In the case of not containing cells, the risk of infection by viruses and the like attributable to the body or the culturing process can be reduced, thereby making the procedure simpler.

The composition for treating a cartilage disease of the present invention has cartilage repair effects, effects that suppress cartilage degenerative changes, cartilage protective effects, effects that inhibit inflammation of joint tissue and/or effects that suppress pain caused by inflammation of joint tissue by being injected into a joint in a liquid state, thereby enabling it to demonstrate therapeutic effects on a cartilage disease. The composition is particularly useful for the treatment of osteoarthritis, the treatment of frozen shoulder and alleviation of joint pain associated with rheumatoid arthritis.

The invention claimed is:

1. A method for regenerating hyaline cartilage comprising: applying a composition comprising a low endotoxin monovalent metal salt of alginic acid and at least one type of cell selected from the group consisting of bone marrow mesenchymal stem cells and bone marrow mesenchymal stromal cells to a cartilage injury lesion;

and curing the surface of the composition and thereby regenerating hyaline cartilage, wherein the composition has a viscosity of 400 mPa·s to 20000 mPa·s and has fluidity, and wherein the monovalent metal salt of alginic acid is a monovalent metal salt of alginic acid having a weight average molecular weight of 500,000 or more as determined by gel filtration chromatography.

2. The method according to claim 1, wherein a crosslinking agent is applied to the surface of the composition to cure the composition.

3. The method according to claim 1, wherein cells are embedded in the composition after culturing in vitro without differentiation induction.

4. The method according to claim 1, wherein applying to the cartilage injury lesion is either a) application to a cartilage defect, or b) formation of one or more holes in the cartilage injury lesion or a cartilage defect and application to the formed holes.

5. The method according to claim 1, wherein the composition is adhered for at least 5 seconds to a cartilage injury lesion that has an opening or defect that is inclined or facing downward.

6. The method according to claim 1, wherein the composition is applied to the cartilage injury lesion with a 16G to 27G needle.

7. The method according to claim 1, wherein the monovalent metal salt of alginic acid is sodium alginate or potassium alginate.

8. The method according to claim 1, further comprising,
irrigating and drying the cartilage injury lesion before applying the composition;
applying a $CaCl_2$ solution to the surface of the applied composition to cure the composition; and
removing the $CaCl_2$ solution following curing,
wherein the applying, irrigating and removing steps are performed arthroscopically.

9. The method according to claim 2, wherein the cross linking agent is a compound selected from the group consisting of $Ca^{2+}$, $Mg^{2+}$, $Ba^{2+}$, and $Sr^{2+}$.

10. The method according to claim 1, wherein the composition does not contain a growth factor.

11. The method according to claim 1, wherein prior to applying the composition to a cartilage injury lesion, the cells are cultured in vitro in one or more states selected from the group consisting of a) a state in which the number of cells is $1\times10^6$ cells/mL or more, b) a state in which hyaline or hyaline-like cartilage tissue is detected by Safranin-O staining or H-E staining, c) a state in which type II collagen is detected by anti-collagen II antibody or genetic analysis, d) a state in which aglycan is detected by anti-aglycan antibody or genetic analysis, and e) a state in which the extracellular matrix is secreted.

12. The method according to claim 1, wherein the cells are bone marrow mesenchymal stromal cells and bone marrow mesenchymal stem cells.

13. A method for regenerating hyaline cartilage comprising:
embedding at least one type of cell selected from the group consisting of bone marrow mesenchymal stem cells and bone marrow mesenchymal stromal cells in a composition comprising a low endotoxin monovalent metal salt of alginic acid,
applying the composition to a cartilage injury lesion;
and curing the surface of the composition and thereby regenerating hyaline cartilage, wherein the composition has a viscosity of 400 mPa·s to 20000 mPa·s and has fluidity, and wherein the monovalent metal salt of alginic acid is a monovalent metal salt of alginic acid having a weight average molecular weight of 500,000 or more as determined by gel filtration chromatography.

14. The method according to claim 13, wherein a crosslinking agent is applied to the surface of the composition to cure the composition.

15. The method according to claim 13, wherein cells are embedded in the composition after culturing the cells in vitro without differentiation induction.

16. The method according to claim 13, wherein the monovalent metal salt of alginic acid is sodium alginate or potassium alginate.

17. The method according to claim 14, wherein the cross linking agent is a compound selected from the group consisting of $Ca^{2+}$, $Mg^{2+}$, $Ba^{2+}$, and $Sr^{2+}$.

18. The method according to claim 13, wherein the composition does not contain a growth factor.

19. The method according to claim 13, wherein the cells are bone marrow mesenchymal stromal cells and bone marrow mesenchymal stem cells.

\* \* \* \* \*

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial sequence
<220> FEATURE:
<223> OTHER INFORMATION: synthetic DNA

<400> SEQUENCE: 1
taagagctcc aaggccaaga                                              20

<210> SEQ ID NO 2
<211> LENGTH: 20
<212> TYPE: DNA
<213> ORGANISM: Artificial sequence
<220> FEATURE:
<223> OTHER INFORMATION: synthetic DNA

<400> SEQUENCE: 2
tgtacctact cctttgaccg                                              20

<210> SEQ ID NO 3
<211> LENGTH: 20
<212> TYPE: DNA
<213> ORGANISM: Artificial sequence
<220> FEATURE:
<223> OTHER INFORMATION: synthetic DNA

<400> SEQUENCE: 3
agagacctga actgggcaga                                              20

<210> SEQ ID NO 4
<211> LENGTH: 22
<212> TYPE: DNA
<213> ORGANISM: Artificial sequence
```

```
<220> FEATURE:
<223> OTHER INFORMATION: synthetic DNA

<400> SEQUENCE: 4
accacgatat gaggcacagt tt                                              22

<210> SEQ ID NO 5
<211> LENGTH: 20
<212> TYPE: DNA
<213> ORGANISM: Artificial sequence
<220> FEATURE:
<223> OTHER INFORMATION: synthetic DNA

<400> SEQUENCE: 5
gccaggacct ccaggactat                                                 20

<210> SEQ ID NO 6
<211> LENGTH: 19
<212> TYPE: DNA
<213> ORGANISM: Artificial sequence
<220> FEATURE:
<223> OTHER INFORMATION: synthetic DNA

<400> SEQUENCE: 6
ctttggacct gttgtccct                                                  19

<210> SEQ ID NO 7
<211> LENGTH: 20
<212> TYPE: DNA
<213> ORGANISM: Artificial sequence
<220> FEATURE:
<223> OTHER INFORMATION: synthetic DNA

<400> SEQUENCE: 7
gaggtcgtgg tgaaaggtgt                                                 20

<210> SEQ ID NO 8
<211> LENGTH: 20
<212> TYPE: DNA
<213> ORGANISM: Artificial sequence
<220> FEATURE:
<223> OTHER INFORMATION: synthetic DNA

<400> SEQUENCE: 8
tgacagtcca tggggtaggt                                                 20

<210> SEQ ID NO 9
<211> LENGTH: 20
<212> TYPE: DNA
<213> ORGANISM: Artificial sequence
<220> FEATURE:
<223> OTHER INFORMATION: synthetic DNA

<400> SEQUENCE: 9
aagggctacg actggacgct                                                 20

<210> SEQ ID NO 10
<211> LENGTH: 16
<212> TYPE: DNA
<213> ORGANISM: Artificial sequence
<220> FEATURE:
<223> OTHER INFORMATION: synthetic DNA

<400> SEQUENCE: 10
gtgcagttcg ccgggt                                                     16
```